US011951014B2

(12) United States Patent
Surma et al.

(10) Patent No.: US 11,951,014 B2
(45) Date of Patent: *Apr. 9, 2024

(54) UPPER EXTREMITY FUSION DEVICES AND METHODS

(71) Applicant: MEDARTIS AG, Basel (CH)

(72) Inventors: Gabriel Surma, Winona Lake, IN (US); Pamela C. Guzman, Fort Wayne, IN (US); Mary Pile, Knoxville, TN (US); Dale Dellacqua, Bloomington, IN (US); Andrew K. Palmer, Eastham, MA (US)

(73) Assignee: MEDARTIS AG, Basel (CH)

(*) Notice: Subject to any disclaimer, the term of this patent is extended or adjusted under 35 U.S.C. 154(b) by 644 days.

This patent is subject to a terminal disclaimer.

(21) Appl. No.: 16/822,736

(22) Filed: Mar. 18, 2020

(65) Prior Publication Data
US 2020/0261235 A1    Aug. 20, 2020

Related U.S. Application Data

(60) Continuation of application No. 15/488,903, filed on Apr. 17, 2017, now Pat. No. 10,617,529, which is a
(Continued)

(51) Int. Cl.
*A61F 2/42* (2006.01)
*A61B 17/17* (2006.01)
(Continued)

(52) U.S. Cl.
CPC ........ *A61F 2/4261* (2013.01); *A61B 17/1725* (2013.01); *A61B 17/1739* (2013.01);
(Continued)

(58) Field of Classification Search
CPC ....... A61B 17/86–17/866; A61B 17/17; A61B 17/1739; A61B 17/1725; A61B 17/17728;
(Continued)

(56) References Cited

U.S. PATENT DOCUMENTS 4,027,573 A * 6/1977 Laverty ............... F16B 25/0031
411/413
4,541,424 A * 9/1985 Grosse ............... A61B 17/1703
606/97
(Continued)

FOREIGN PATENT DOCUMENTS

WO    2007138062 A1    12/2007
WO    2010033702 A2    3/2010

OTHER PUBLICATIONS

International Preliminary Report on Patentability for PCT application No. PCT/US2012/022755, dated Aug. 8, 2013.
(Continued)

*Primary Examiner* — Zade Coley
(74) *Attorney, Agent, or Firm* — Heslin Rothenberg Farley & Mesiti P.C.; Victor A. Cardona, Esq.

(57) ABSTRACT

A fusion implant and fusion members for fusing target bones of an upper extremity. The fusion implant including internally threaded apertures of a first thread lead, and the fusion members including threading of the first thread lead and threading of a second thread lead that is less than the first thread lead. The fusion implant and a targeting instrument being configured to couple to one another in a predefined orientation. The predetermined orientation resulting in alignment of aspects of the fusion implant with aspects of the targeting instrument. A guide clamp for facilitating forming of an implant cavity in adjacent bones for implantation of the fusion implant therein. A surgical method for facilitating fusion of adjacent target bones utilizing a fusion implant, fusion members, a targeting instrument and a guide clamp to reduce space between the adjacent bones such that they at least abut one another.

16 Claims, 22 Drawing Sheets

Related U.S. Application Data division of application No. 13/982,124, filed as application No. PCT/US2012/022755 on Jan. 26, 2012, now Pat. No. 9,662,221.

(60) Provisional application No. 61/500,024, filed on Jun. 22, 2011, provisional application No. 61/436,498, filed on Jan. 26, 2011.

(51) Int. Cl.
*A61B 17/68* (2006.01)
*A61B 17/86* (2006.01)
*A61F 2/30* (2006.01)

(52) U.S. Cl.
CPC .......... *A61B 17/1782* (2016.11); *A61B 17/68* (2013.01); *A61B 17/863* (2013.01); *A61B 17/8645* (2013.01); *A61B 17/8685* (2013.01); *A61F 2/42* (2013.01); *A61F 2002/30622* (2013.01)

(58) Field of Classification Search
CPC .......... A61F 2/4261; A61F 2002/30622; A61F 2002/30803; A61F 2002/30787; A61F 2002/30784
See application file for complete search history.

(56) References Cited

U.S. PATENT DOCUMENTS

| | | | | |
|---|---|---|---|---|
| 4,622,959 A * | 11/1986 | Marcus | A61B 17/1721 | 606/98 |
| 4,776,330 A * | 10/1988 | Chapman | A61B 17/8061 | 606/64 |
| 4,848,327 A * | 7/1989 | Perdue | A61B 17/1703 | 408/91 |
| 4,911,153 A * | 3/1990 | Border | A61B 17/1725 | 606/98 |
| 5,034,013 A * | 7/1991 | Kyle | A61B 17/7266 | 606/62 |
| 5,259,398 A * | 11/1993 | Vrespa | A61C 8/0025 | 411/413 |
| 5,295,991 A * | 3/1994 | Frigg | A61B 17/1725 | 606/62 |
| 5,474,561 A * | 12/1995 | Yao | A61B 17/1725 | 606/98 |
| 6,030,162 A * | 2/2000 | Huebner | A61B 17/8863 | 411/413 |
| 6,093,192 A * | 7/2000 | Abel | A61B 17/1725 | 606/98 |
| 6,143,032 A * | 11/2000 | Schafer | A61F 2/442 | 606/907 |
| 6,306,140 B1 * | 10/2001 | Siddiqui | A61B 17/863 | 606/315 |
| 7,179,259 B1 * | 2/2007 | Gibbs | A61F 2/4603 | 606/98 |
| 7,311,710 B2 * | 12/2007 | Zander | A61B 17/1721 | 606/53 |
| 7,588,577 B2 * | 9/2009 | Fencl | A61B 17/72 | 606/62 |
| 8,034,056 B2 * | 10/2011 | Fencl | A61B 17/7266 | 606/86 R |
| 8,257,361 B2 * | 9/2012 | Ritchey | A61B 17/1725 | 606/96 |
| 8,771,283 B2 * | 7/2014 | Larsen | A61B 17/1725 | 606/98 |
| 8,986,315 B2 * | 3/2015 | Durante | A61B 17/1725 | 606/96 |
| 9,017,329 B2 * | 4/2015 | Tyber | A61B 17/8615 | 411/457 |
| 9,603,640 B2 | 3/2017 | Palmer et al. | | |
| 2005/0119753 A1 * | 6/2005 | McGahan | A61F 2/4611 | 623/17.11 |
| 2005/0283154 A1 * | 12/2005 | Orbay | A61B 17/8061 | 606/62 |
| 2006/0015123 A1 * | 1/2006 | Fencl | A61B 17/1725 | 606/104 |
| 2006/0025773 A1 * | 2/2006 | Yevmenenko | A61B 17/863 | 606/317 |
| 2006/0122600 A1 * | 6/2006 | Cole | A61B 17/164 | 606/62 |
| 2007/0123878 A1 * | 5/2007 | Shaver | A61B 17/7233 | 606/64 |
| 2008/0077132 A1 | 3/2008 | Medoff | | |
| 2009/0062797 A1 * | 3/2009 | Huebner | A61B 17/1739 | 606/151 |
| 2009/0149861 A1 * | 6/2009 | Brodsky | A61B 17/72 | 606/62 |
| 2009/0157077 A1 * | 6/2009 | Larsen | A61B 17/1725 | 606/62 |
| 2009/0292292 A1 * | 11/2009 | Fencl | A61B 17/1725 | 606/104 |
| 2011/0125153 A1 * | 5/2011 | Tyber | A61B 17/1775 | 606/62 |
| 2011/0245885 A1 * | 10/2011 | Powell | A61B 17/1725 | 606/86 R |
| 2012/0095560 A1 * | 4/2012 | Donner | A61F 2/4455 | 623/17.11 |
| 2012/0330313 A1 * | 12/2012 | Grady | A61B 17/7225 | 606/64 |
| 2013/0030446 A1 * | 1/2013 | Wayne | A61B 17/1775 | 606/104 |
| 2017/0216043 A1 | 8/2017 | Surma | | |

OTHER PUBLICATIONS

International Search Report for PCT/US2012/022755 dated Jul. 6, 2012.

* cited by examiner

UPPER EXTREMITY FUSION DEVICES AND METHODS

CROSS REFERENCE TO RELATED APPLICATIONS

This is a Continuation patent application of U.S. patent application Ser. No. 15/488,903 filed Apr. 17, 2017, which is a Divisional patent application of U.S. Ser. No. 13/982,124, entitled "UPPER EXTREMITY FUSION DEVICES AND METHODS", filed Aug. 26, 2013, which is a 371 national phase of PCT/US2012/022755 filed on Jan. 26, 2012, which claims priority to provisional application Nos. 61/436,498 and 61/500,024 filed Jan. 26, 2011 and Jun. 22, 2011 respectively, which are incorporated herein by reference.

BACKGROUND OF THE INVENTION

1. Field of the Invention

The present invention relates to the field of fixation of anatomical structures, and, in particular, to devices, methods and instrumentation for facilitating bone fusion in an upper extremity of a patient.

2. Description of the Related Art

In some instances bone fusion, or arthrodesis, of anatomy including multiple bone structures may be desirable, such as arthrodesis of the upper extremity bones of the wrist or hand. Wrist or carpus arthrodesis is an established surgical technique to join or fuse adjacent bones in the wrist by rigidly positioning them at their articular surfaces. By maintaining this placement, sometimes in the presence of a bone graft, bone cell growth or other anatomical growth may be stimulated which may cause the bones to fuse together. Once the bones are fixed to one another, all motion that existed at the corresponding joint surfaces of the bones ceases, stability is achieved and any pain caused by the irritation of corresponding nerves is significantly reduced or eliminated. For example, in certain patients with post-traumatic arthritis, rheumatoid arthritis, osteoarthritis, carpal instability, complex or localized fractures or other injury, disease or destructive or painful conditions involving the bones of the wrist, fusion of particular bones of the wrist can alleviate resulting pain, discomfort and instability. Unfortunately, effective fusion of the wrist which balances pain relief, joint stability and retention of some effective movement of the wrist is rarely achieved, no less consistently achieved.

Several surgical approaches have been developed to maximize alleviation of wrist pain and/or instability by arthrodesis. For example, total wrist arthrodesis is very effective in relieving pain, but almost all wrist motion is lost. Since the articulation afforded to the hand by the wrist is important for mobility, strength and dexterity, total wrist arthrodesis is often thought of as a last resort. As another example, limited or partial wrist arthrodesis is often desired in an effort to preserve motion of the wrist to the greatest degree possible. Partial wrist arthrodesis is fusion of a selected group of wrist bones. Variations of the procedure, such as triscaphe, radioscaphoid, radiolunate, scapholunate-capitate and four-corner fusion, attempt to alleviate pain by fusing particular articulations determined or suspected of originating pain and/or instability. Partial wrist arthrodesis is particularly advantageous in patients that desire intricate use of their hands because more residual motion of the wrist can be preserved.

Currently, in both total and partial wrist arthrodesis scenarios, it is common for plates, implants, wires, screws, staples and external fixation devices to be used as the fusion medium. These devices are used alone or in combination to attempt to achieve the desired level of fusion.

The placement and orientation of the bones of the wrist at the time of a wrist fusion is critical to obtaining a bony fusion, preserving maximal wrist motion in partial fusion, and preventing, for example, progressive arthritis of the wrist. One of the drawbacks encountered with prior art partial fusion devices, methods and instrumentation is that they fail to provide consistent and reproducible fusion, and therefore partial arthrodesis rarely results in full relief of pain. For example, when plates, implants, screws and the like are used to achieve partial wrist fusion, the exact placement of the particular plate, implant or screws from surgeon to surgeon and patient to patient are rarely consistent. As such, the predictability of the exact clinical outcome of partial wrist fusion with such prior art devices is low. As a result, there remains much room for improvement in the art for effective fusion devices, methods and instrumentation that provide reproducible alignment, orientation and configuration of the fusion medium with respect to target fixation bones in order to achieve predictable and consistent fusion of such target fixation bones.

Accordingly, it is an object of the present invention to overcome one or more of the above-described drawbacks and/or disadvantages of the prior art. For example, in view of the deficiencies of current designs of partial wrist or hand fusion devices and methods, and similar fusion devices and methods for other areas of the body where multiple bone structures exist including, but not limited to, the foot, ankle and spine, and the lack of proper associated devices, instrumentation and methods to achieve consistent post-operative results, it would be desirable to develop devices, instrumentation and methods to allow a surgeon to achieve satisfactory long term, predictable clinical outcomes for these types of fusion surgeries.

SUMMARY OF THE INVENTION

The present disclosure is directed to devices, instruments, clamps and methods for fusing, or facilitating fusion, of bones of the upper extremity.

In accordance with one aspect of the present invention, a bone fusion device for use with bones of an upper extremity is disclosed. In some embodiments, the bone fusion device may include a fusion implant configured for implantation into a cavity spanning at least two adjacent bones, and at least two longitudinally extending bone fusion members including a tip, a head and a shank extending longitudinally between the tip and the head.

In some such embodiments, the fusion implant may include a first end including an attachment mechanism configured to couple with an instrument in a predefined first orientation, a second end substantially opposing the first end, and a body extending longitudinally between the first end and the second end. In some embodiments, the body may include a substantially smooth outer surface and define a longitudinal axis.

In some such embodiments, the body may further include at least two non-threaded apertures extending laterally through the body from a first side of the body to a second side of the body and at least two internally threaded apertures including a first thread lead extending laterally through the body from a third side of the body to a fourth side of the body.

In some such embodiments, the at least two threaded apertures of the body include a first threaded aperture proximate the first end, and a second threaded aperture proximate the second end of the body. In some embodiments the second threaded aperture may be angled with respect to the longitudinal axis of the body such that the second threaded aperture defines an axis that angles away from the second end as it extends from the third side to the fourth side.

In some embodiments, the at least two bone fusion members include a first externally threaded portion adjacent the tip including the first thread lead and being otherwise configured to couple to the at least two threaded apertures of the body of the fusion implant. In some such embodiments, the at least two bone fusion members further includes a second externally threaded portion adjacent the head including a second thread lead that is less than the first thread lead and an external taper extending from the head to the tip. In some such embodiments, the at least two bone fusion members also include a non-threaded portion extending between the first and second externally threaded portions.

In some embodiments, the at least two non-threaded apertures of the body define substantially parallel axes. In some embodiments, the fusion implant is substantially cylindrical, and the first and second sides of the body are spaced about 90 degrees from the third and fourth sides of the body about the longitudinal axis.

In some embodiments, the body of the fusion implant includes a third internally threaded aperture adjacent the second internally threaded aperture. In some such embodiments, the third internally threaded aperture extends laterally through the body and defines an axis that is substantially parallel to the axis of the second internally threaded aperture. In some such embodiments, the fusion implant includes only two non-threaded apertures and the first, second and third internally threaded apertures. In some such embodiments, the first internally threaded aperture is adjacent the first end, a first non-threaded aperture is positioned between the first internally threaded aperture and the second end, the third internally threaded aperture is positioned between the first non-threaded aperture and the second end, the second internally threaded aperture is positioned between the third internally threaded aperture and the second end, and a second non-threaded aperture is positioned between the second internally threaded aperture and the second end.

In some such embodiments, the angle between the axis of the first internally threaded aperture and the longitudinal axis of the body adjacent the third side and first end of the body is within the range of about 95 degrees to about 80 degrees, and the angle between the axis of the second and third internally threaded apertures and the longitudinal axis of the body adjacent the third side and first end of the body is within the range of about 92 degrees to about 106 degrees. In some such embodiments, the first internally threaded aperture is angled with respect to the longitudinal axis of the body such that it defines an axis that angles away from the first end as it extends from the third side to the fourth side. In some such embodiments, a plane extends between the axes of the internally threaded apertures and the longitudinal axis of the body, and the axes of the non-threaded apertures are normal to the plane.

In some embodiments, the first threaded portion and the non-threaded portion of the at least two bone fusion members define a first outer diameter, and the second threaded portion of the at least two bone fusion members defines a second outer diameter adjacent the head that is greater than the first outer diameter.

In accordance with another aspect of the present invention, a surgical instrument for use in obtaining bone fusion in an upper extremity of a patient is disclosed. In some such embodiments, the instrument includes a fusion implant, a targeting member, at least one guide member and an outrigger member.

In some such embodiments, the fusion implant includes a first end, a second end and a body extending longitudinally therebetween defining a first axis. In some such embodiments, the body includes at least one aperture extending laterally therein defining a second axis.

In some such embodiments, the targeting member includes at least one arm, at least one bone fusion member aperture configured to receive a bone anchor therethrough, and at least one clamp member configured to securely couple with a bone anchor member clamp.

In some such embodiments, the at least one guide member is coupled to the at least one arm of the targeting member and includes an aperture extending through the at least one guide member defining a third axis.

In some such embodiments, the outrigger member is coupled to the at least one arm of the targeting member and securely removably coupled to the first end of the fusion implant in a first orientation of the fusion implant. In some such embodiments, the outrigger member and the at least one guide member are configured such that the second axis of the bone fusion member aperture of the fusion implant and the third axis of the aperture of the at least one guide member are substantially aligned in the first orientation of the fusion implant.

In some such embodiments, the at least one arm of the targeting member includes at least a first arm extending from the targeting member to the outrigger member, and a second arm extending from the targeting member to the at least one guide member.

In some such embodiments, the first arm and the second arm are configured to space the outrigger member and the at least one guide member from each other along the first axis of the fusion implant and along the third axis of the aperture of the at least one guide member. In some other such embodiments the outrigger member and the first end of the fusion implant are configured to be securely removably coupled to one another in only the first orientation. In some other such embodiments the outrigger member and the first end of the fusion implant are configured to provide a visual or tactile indication when they are coupled to one another in an orientation different than the first orientation. In some other such embodiments the instrument further includes at least one bone anchor clamp configured to selectively couple to the at least one clamp member and a bone anchor.

In accordance with another aspect of the present invention, a guide clamp for use in positioning a fusion implant in at least one bone to obtain a bone fusion in an upper extremity of a patient is disclosed. In some such embodiments, the guide clamp includes a first arm member and a second arm member.

In some such embodiments, the first arm member includes a longitudinally extending guide member defining a first bone abutment surface and an aperture extending linearly therethrough defining a first axis.

In some such embodiments, the second arm member includes a bone abutment member spaced from the guide member and being in a first orientation with respect to the first axis of the aperture of the guide member. In some such embodiments, the bone abutment member includes a second bone abutment surface extending towards the first bone abutment surface in the first orientation and a third bone abutment surface extending at least to the first axis of the aperture of the guide member in the first orientation In some such embodiments, the first arm and the second arm are moveably coupled to one another. In some such embodiments, the guide member and the bone abutment member are configured such that the first orientation is maintained during movement of the first arm and guide member and the second arm and bone abutment member relative to the other.

In some embodiments, the first arm and second arm are hinged at a medial location of the arms, the guide member is rotatably coupled with the first arm, and the bone abutment member is rotatably coupled to the second arm. In some such embodiments, a positioning member is coupled to the bone abutment member and the guide member in such a manner that allows the abutment member and the guide member to rotate with their respective arms in response to movement of the first arm and second arm about the hinge to maintain the first orientation.

In accordance with another aspect of the present invention, a surgical method for fusing bones is disclosed. In some embodiments, the surgical method includes the step of drilling an implant aperture extending through a first bone and at least partially through a second bone.

In some such embodiments, the surgical method further includes the step of removably coupling a first end of a fusion implant including at least one internally threaded bone fusion member aperture including a first thread lead to a surgical targeting instrument in a first predefined orientation dictated by the configuration of at least one of the first end of the fusion implant and the surgical targeting instrument.

In some such embodiments, the surgical method further includes the step of inserting the fusion implant within the implant aperture through the first bone and at least partially through the second bone such that at least one of the least one internally threaded bone fusion member aperture is positioned within the first bone.

In some such embodiments, the surgical method further includes the step of positioning a first elongated aperture defining a first axis provided on the surgical targeting instrument proximate a third bone spacedely disposed adjacent the first bone.

In some such embodiments, the surgical method further includes the step of positioning a drill bit within the first elongated aperture provided on the surgical targeting instrument, and drilling along the first axis to form a bone fusion member aperture extending through the third bone and at least partially through the first bone to at least the at least one internally threaded bone fusion member aperture.

In some such embodiments, the surgical method further includes the step of rotationally inserting a first bone fusion member including a first externally threaded portion including the first thread lead adjacent a tip of the member and a second externally threaded portion of a second thread lead that is less than the first thread lead adjacent a head of the member into the bone fusion member aperture such that the first externally threaded portion is threadably engaged with the at least one internally threaded bone fusion member aperture, the second externally threaded portion is engaged with the third bone, and the fusion implant and the first bone fusion member apply a compressive force to the joint between adjacent surfaces of the first bone and the second bone to facilitate fusion therebetween.

In some such embodiments, the step of drilling an implant aperture includes the step of applying a first bone abutment surface of a drill guide clamp to a first surface of the first bone and applying a second bone abutment surface of the drill guide clamp to a second bone surface opposing the first bone surface of the second bone. In some such embodiments, the step of drilling an implant aperture further includes the step of positing a drill bit within a first elongated aperture of the drill guide clamp defining a second axis and drilling an implant aperture extending through the first bone and at least partially through the second bone from the first surface of the first bone toward the second bone abutment surface and second bone surface along the second axis.

In some such embodiments of the surgical method, the fusion implant includes at least two internally threaded bone fusion member apertures including the first thread lead and at least one of the at least two internally threaded bone fusion member apertures is positioned within the second bone. In some such embodiments of the surgical method, the surgical targeting instrument includes a second elongated aperture defining a second axis.

In some such embodiments, the surgical method further includes the step of positioning the second elongated aperture provided on the surgical targeting instrument proximate a fourth bone spacedely disposed adjacent the second bone. In some such embodiments, the surgical method further includes the step of positioning a drill bit within the second elongated aperture provided on the surgical targeting instrument and drilling a second bone fusion member aperture along the second axis extending through at least the fourth bone and at least partially through the second bone to at least a second internally threaded bone fusion member aperture of the fusion implant. In some such embodiments, the surgical method further includes the step of rotationally inserting a second bone fusion member including a first externally threaded portion including the first thread lead adjacent a tip of the member and a second externally threaded portion of a second thread lead that is less than the first thread lead adjacent a head of the second member into the second bone fusion member aperture such that the first externally threaded portion is threadably engaged with the second internally threaded bone fusion member aperture, the second externally threaded portion is engaged with the fourth bone, and the space between the fourth bone and the second bone is substantially eliminated.

Other objects, aspects and advantages of the fusion devices and methods of the present invention, and/or of the currently preferred embodiments thereof, will become more readily apparent in view of the following detailed description of the currently preferred embodiments and the accompanying drawings.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
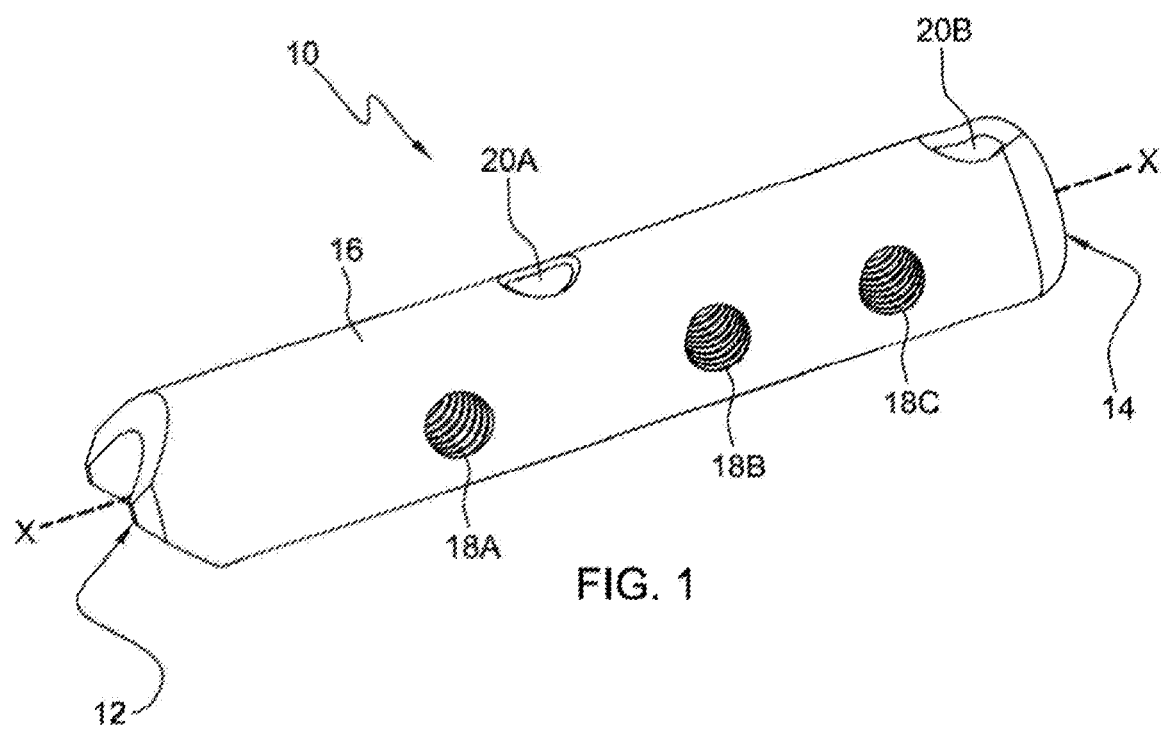
FIG. 1 is a front elevational perspective view of an exemplary embodiment of a fusion implant of the present invention.

In this application, the words proximal, distal, anterior or palmar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the hand or wrist, the term "dorsal" refers to the top of the hand or wrist and the term "palmar" refers the bottom or palm of the hand or wrist.

Similarly, positions or directions may be used herein with reference to anatomical structures or surfaces. For example, as the current devices, instrumentation and methods are described herein with reference to use with the bones of the wrist, the bones of the wrist, hand and arm may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the left wrist or hand may be mirrored so that they likewise function with the right wrist.

In FIGS. 1-8, a fusion implant embodying a first embodiment is indicated generally by the reference numeral 10. As shown in FIGS. 1-8, the fusion implant 10 may be a post-like member. The exemplary illustrated fusion implant 10 is a substantially cylindrical member having a substantially circular cross-sectional geometry of constant thickness. In alternative embodiments, the fusion implant 10 may define a non-cylindrical shape or any other geometrical shape and thicknesses (constant or varying).

Figure 2:
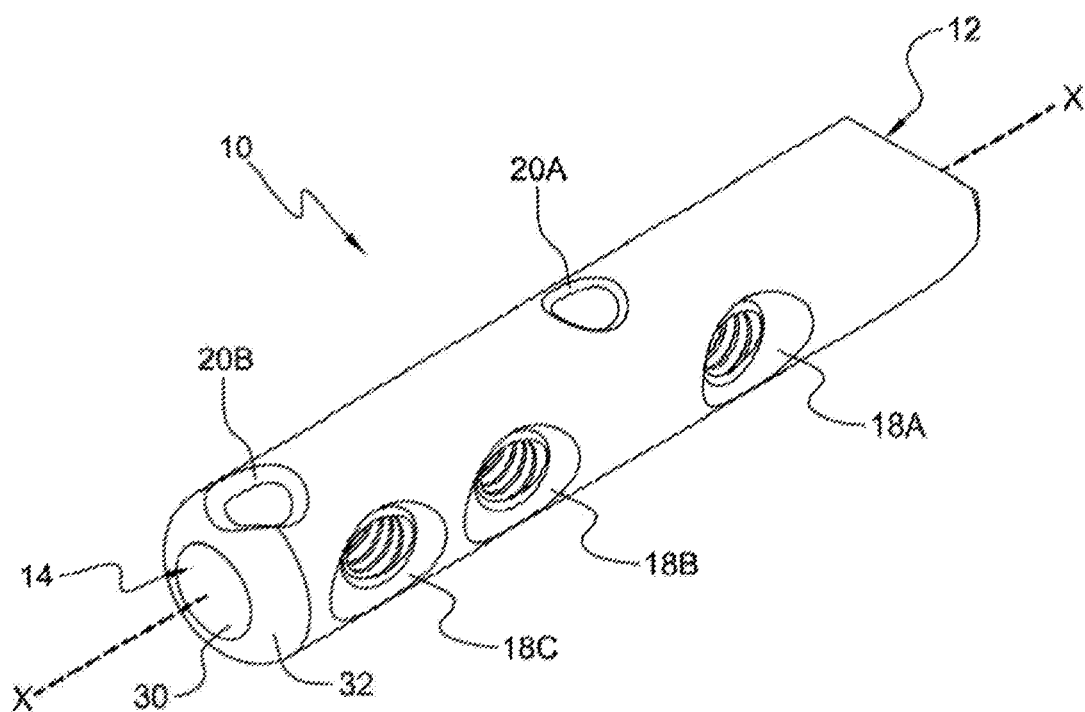
FIG. 2 is a rear elevational perspective view of the fusion implant of FIG. 1.

As shown in the perspective views of FIGS. 1 and 2, the exemplary illustrated fusion implant 10 includes an exemplary first end or tip 12 and a substantially opposing exemplary second end 14. A body 16 of the fusion implant 10 extends between the first end 12 and the second end 14 and defines an exemplary substantially smooth cylindrical shape defining the longitudinal axis X-X. The body 16 includes apertures extending therethrough and a longitudinal axis of the device 10. In the illustrated embodiments, the longitudinal axis X-X of the body 16 defines the longitudinal axis of the fusion implant 10. In alternative embodiments, the longitudinal axis X-X of the body 16 differs from the longitudinal axis of the fusion implant 10. In some embodiments, the fusion implant 10 and body 16 define a non-cylindrical shape and thickness (constant or varying). In some embodiments, the outer surface of the device includes external threads and/or at least a macro, micro or nano texture or structure.

The apertures of the body 16 may include internally threaded and non-threaded apertures extending through, or partially through, the body 16 at different locations and angles or orientations. For example, some apertures may define an axis that passes through the longitudinal axis X-X, while other apertures may define an axis that is spaced from the longitudinal axis X-X. The apertures may also define any shape or size, such as circular and non-circular apertures, and may extend linearly or non-linearly through, or partially through, the body 16. The number of the internally threaded and non-threaded apertures may also vary, such as a body 16 including at least one threaded aperture and not including any non-threaded apertures, or a body 16 including at least one threaded aperture and at least one non-threaded aperture. In some embodiments, the body 16 may include at least two threaded apertures and at least one non-threaded aperture.

In the illustrated embodiment, the exemplary body 16 includes three exemplary threaded apertures 18A-C each defining axes and two exemplary non-threaded apertures 20A, 20B each defining axes Y1-Y1, the axes of the threaded apertures 18A-C and non-threaded apertures 20A, 20B oriented substantially perpendicular to each another in at least one plane. The exemplary threaded apertures 18A-C and non-threaded apertures 20A, 20B extend substantially linearly entirely through the body 16 and pass substantially through the longitudinal axis X-X (i.e., the apertures pass through the entire thickness of the body 16). The exemplary threaded apertures 18A-C and non-threaded apertures 20A, 20B define substantially circular cross-sections, and thus are substantially cylindrical in nature. The threaded apertures 18A-C may include internal threads extending substantially along the entire length of the apertures 18A-C, or the threading may extend to only a portion of the length of the apertures 18A-C. In the illustrated embodiment, the entire length or thickness of the threaded apertures 18A-C includes the internal threading (see FIGS. 7 and 8). The inner surfaces of the non-threaded apertures 20A, 20B may define substantially straight and smooth surfaces. In some embodiments, however, the inner surfaces of the non-threaded apertures 20A, 20B do not define substantially straight and smooth surfaces.

Figure 3:
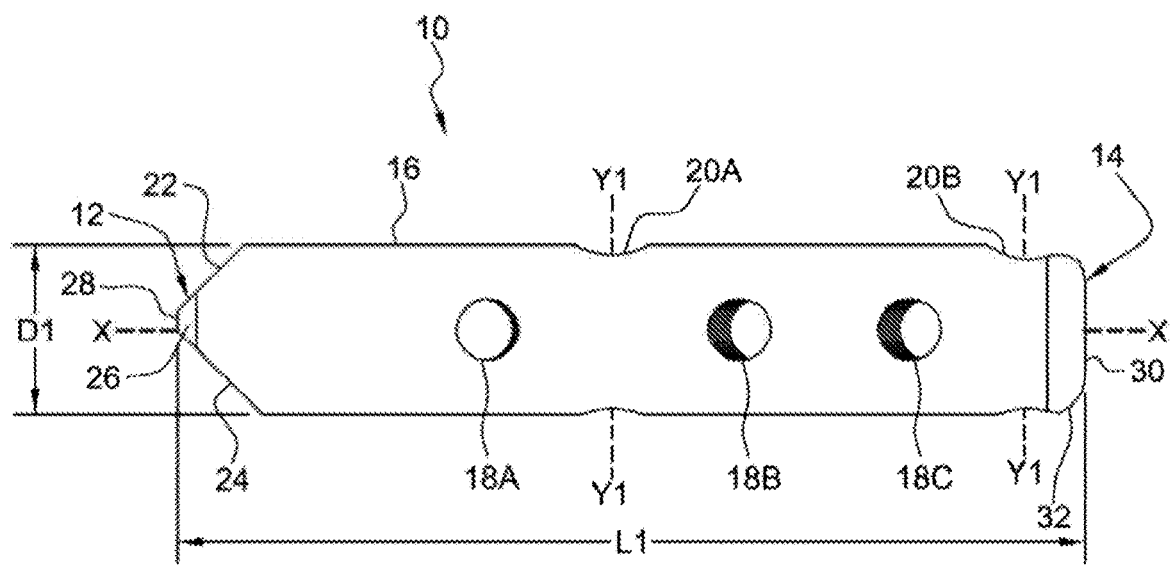
FIG. 3 is a rear side view of the fusion implant of FIG. 1.
Figure 4:
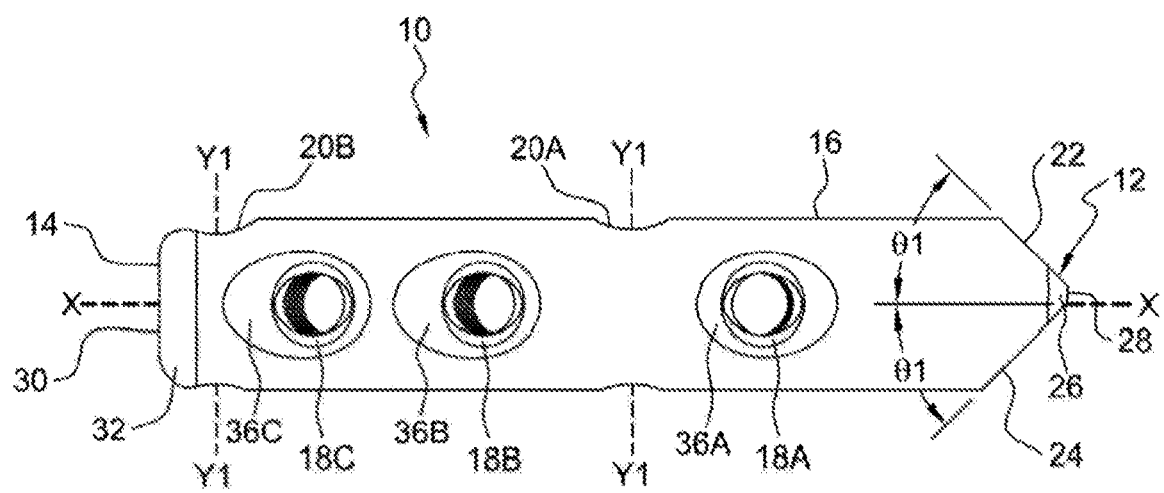
FIG. 4 is a front view of the fusion implant of FIG. 1.

As shown best in FIGS. 3 and 4, the first end 12 of the fusion implant 10 defines an exemplary tip profile with an asymmetrical shape with respect to at least one plane passing through the longitudinal axis X-X of the body 16. In the illustrated embodiment shown in FIGS. 1-8, the tip profile of the first end 12 is asymmetrical with respect to at least a plane extending parallel to the longitudinal axis X-X and substantially normal to axes Y1-Y1 of the non-threaded apertures 20A, 20B. As described in further detail below, the first end 12 is configured asymmetric with respect to at least one plane so that the fusion implant 10 properly mates or couples with an instrument in a predefined first orientation so that a specific, predefined alignment between the fusion implant 10 and the instrument is consistently achieved (as well as the orientation of the fusion implant 10 with respect to target fixation bones). For example, the first end 12 (and/or the instrument) may be configured so that it can only mate or couple with an instrument in the predefined first orientation. As another example, the first end 12 may be configured such that it is capable of mating or coupling with an instrument in multiple orientations, including the first orientation, but provides a visual, tactile or other indication when the fusion implant 10 is mated or coupled in an orientation other than the first orientation. For example, the first end 12 (and/or the instrument) may include visual or tactile markings, members, shapes or the like that provide at least one visual or tactile indication for facilitating mating or coupling the fusion implant 10 in the first orientation.

As shown in FIGS. 3-6, the exemplary first end 12 of the illustrated fusion implant 10 includes four exemplary surfaces extending from the outer surface of the body 16 at acute angles toward the longitudinal axis X-X. As best shown in FIGS. 3-6, the first end 12 includes an exemplary first planar tip surface 22 extending from a top portion of the outer surface of the body 16 and an exemplary second planar tip surface 24 extending from an opposing bottom portion of the outer surface of the body 16. As illustrated in the front and rear side views of FIGS. 3 and 4, the first and second tip surfaces 22, 24 extend from the top and bottom outer surface portions of the body 16, respectively, linearly toward the longitudinal axis X-X of the body 16 at an angle .theta.1. As the outer surface of the exemplary body 16 is cylindrical, the first and second tip surfaces 22, 24 also extend from their respective outer surface portions at the angle .theta.1. In the illustrated embodiment, the first and second tip surfaces 22, 24 are planar and extend from opposing sides of the body 16 at angle .theta.1 of about 45 degrees from the longitudinal axis X-X of the device 10 and their respective outer surface portions, and therefore extend substantially perpendicular to each other. As such, in the illustrated embodiment, the edges formed by the outer surface of body 16 and the first and second tip surfaces 22, 24 (i.e., the outer edges of the first and second tip surfaces 22, 24) are concaved towards the intermediate portion of the body 16.

The exemplary second tip surface 24 extends from a more intermediate portion of the body 16 as compared to the intermediate portion of the body 16 from which the first tip surface 22 extends. However, the first and second tip surfaces 22, 24 extend to the same longitudinal position along the longitudinal axis X-X. As such, the total length of the second tip surface 24 measured from the most intermediate point to the outer most point is greater than the corresponding length of the first tip surface 22 (whether measured along the longitudinal axis X-X or along respective planes defined by the surfaces 22, 24). As described above, and further described below, the difference in the total lengths of the first and second tip surfaces 22, 24 allows a user to accurately and consistently couple the fusion implant 10 with an instrument in the predefined first orientation.

As also illustrated in the side views of FIGS. 3 and 4, the illustrated first end 12 further includes exemplary third and fourth tip surfaces 26 extending from the portions of the outer surface of the body 16 between the first and second 22, 24 tip surfaces toward the longitudinal axis X-X of the body 16. The intermediate portions from which the exemplary third and fourth tip surfaces 26 extend are less intermediate as compared to the intermediate portions from which the first tip surface 22 and second tip surface 24 extend. The exemplary third and fourth tip surfaces 26 intersect, and extend between, the first and second tip surfaces 22, 24. The third and fourth tip surfaces 26 are radiused to form blunt convex surfaces. In the illustrated embodiment, the third and fourth tip surfaces 26 are of identical shape, size, orientation and longitudinal position along the axis X-X. Due to the configuration of the first and second tip surfaces 22, 24, as described above, the third and fourth tip surfaces 26 are not opposed from each other about the longitudinal axis X-X of the body 16, but rather are skewed towards the top portion of the body 16. As described below, this skewed or off-center configuration ensures that the fusion implant will be coupled to an instrument in a pre-defined orientation. As such, the features of the fusion implant 10 can be designed with respect the pre-defined orientation.

The third and fourth radiused tip surfaces 26 intersect with respective exemplary planar first end tip surfaces 28. Each of the first and second planar tip surfaces 22, 24 also intersect with the exemplary planar first end tip surfaces 28. Each exemplary end tip surface 28 extends substantially perpendicular to the longitudinal axis X-X of the body 16, and defines the outer most surface of the fusion implant 10 at the first end 12. Due to the configuration of the first and second tip surfaces 22, 24 and the second and third tip surfaces 26, as described above, the end tip surfaces 28 are not opposed from each other about the longitudinal axis X-X of the body 16, but rather are skewed towards the top portion of the body 16. This skewed relationship or configuration of the first end 12 limits the orientations in which the first end 12 of the fusion member can be coupled to an instrument including a reversed or mirrored configuration of the first end 12, as described further below. For example, an instrument including a reversed or mirrored configuration of the first end 12 will be capable of properly or securely coupling to the first end 12 of the fusion implant 10 in only two predefined orientations, one orientation being a "proper" orientation and the other being "improper." Further, the off-center orientation of the aspects of the first end 12 will provide a visual or tactile indication when the fusion implant 10 coupled to the instrument in the "improper" orientation. In this way, the aspects of the "proper" orientation of the fusion implant 10 can be predetermined and designed for a specific fusion application, since the first end ensures the fusion implant 10 will be orientated in the "proper" orientation.

As shown in FIG. 1, and described further below with respect to FIGS. 7 and 8, the first end 12 further includes an aperture extending from the end tip surfaces 28 towards an intermediate portion of the body 16 about the longitudinal axis X-X. The axially extending aperture thereby forms the inner edges of the end tip surfaces 28 and the first and second tip surfaces 22, 24. As a result, in the illustrated embodiment, the inner edges of the end tip surfaces 28 and the first and second tip surfaces 22, 24 are curved about the longitudinal axis X-X with the radius of curvature of the axially extending aperture. Also, the inner edges of the first and second tip surfaces 22, 24 formed by the axially extending aperture are concaved towards the intermediate portion of the body 16. As the outer edges of the first and second tip surfaces 22, 24 are also concaved, as discussed above, the profile of the first end 12 of the body 16 is concaved towards the intermediate portion of the body 16 when viewed from the top and bottom portions of the body 16.

The second end 14 of the fusion implant 10 and body 16 substantially opposes the first end 12, as shown in FIGS. 1-8. The second end may include any configuration or shape. In the illustrated embodiment, as best shown in FIGS. 2, 3 and 4, the second end 14 includes a planar second end tip surface 30 extending substantially normal to the longitudinal axis X-X of the body 16 and parallel to the axes Y1-Y1 of the non-threaded apertures 20A, 20B. The second end tip surface 30 defines the outer most surface of the fusion implant 10 at the second end 14. In alternative embodiments, the second end tip surface 30 is not planar, but radiused to form a blunt convex second end 14. In the illustrated embodiment, the second end 14 also includes a circumferential radiused edge 32 extending between the outer surface of the body 16 and the second end tip surface 30. In alternative embodiments, the second end 14 does not include the radiused edge 32, and the second end tip surface 30, whatever its configuration or shape, extends to the outer surface of the body 16.

Figure 7:
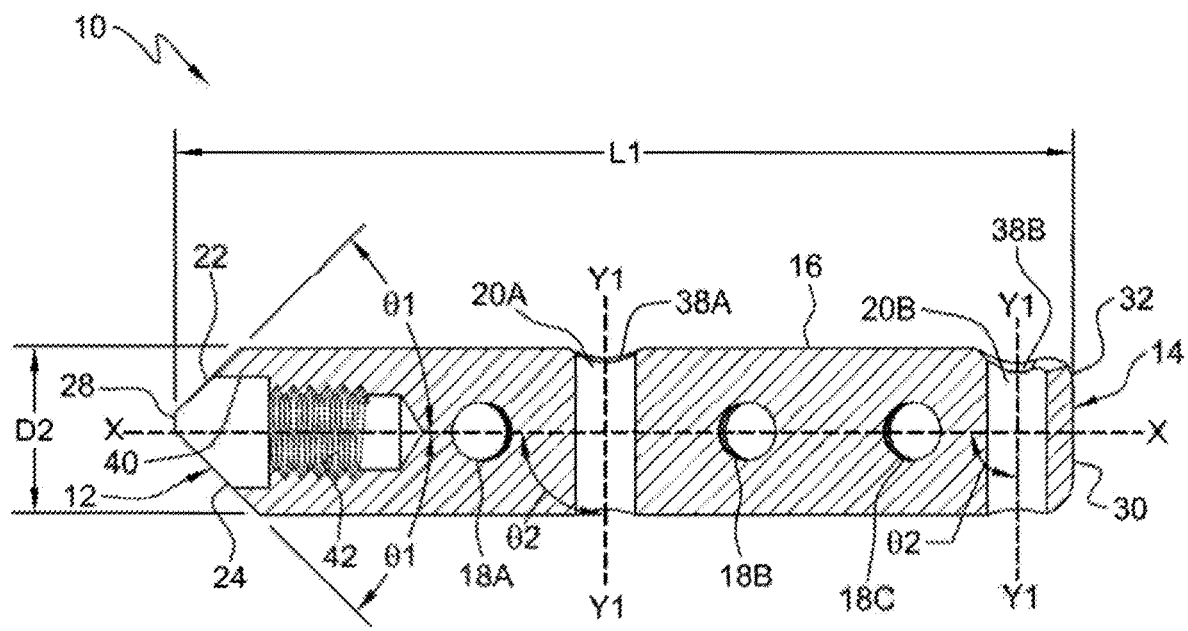
FIG. 7 is a first cross-sectional side view of the fusion implant of FIG. 1 taken along a plane defined by the longitudinal axis and the axes of the non-threaded apertures of the of the fusion implant.

As illustrated in FIGS. 3 and 7, the total axial length L1 of the fusion implant 10 along the longitudinal axis X-X can be measured from the first end surfaces 28 of the first end 12 to the second end surface 30 of the second end 14. Similarly, the diameter D1 of the body 16 (and therefore the diameter of the fusion implant 10) and can be measured from opposing sides of outer surface of the body 16. The axial length L1 and diameter D1 of the fusion implant 10 may vary and depend upon the particular target fusion bones. For example, in the illustrated embodiment the fusion implant 10 is particularly well suited for implantation into the hammate and capitate bones of the wrist for fusion of the triquetral and lunate bones, respectively, thereto, and preferably defines an axial length L1 of about 0.95 inch and a diameter D1 of about 0.18 inch. In some embodiments, such as embodiments for implantation into the bones of an upper extremity, the axial length L1 of the fusion implant 10 may preferably range from about 0.8 inch to about 1.2 inches, and more preferably from about 0.87 in to about 0.95 inches. In some embodiments the diameter D1 of the body 16 and/or the fusion implant 10 may preferably range from about 0.15 inch to about 0.2 inch, and more preferably range from about 0.15 inch to about 0.18 inch. In one embodiment, a fusion kit may include a plurality of fusion implants 10 of differing axial lengths L1, such as a kit including fusion implants 10 of axial lengths from about from 0.8 inch to about 0.95 inches in about 0.08 inch increments. In some such embodiments, the kit further includes at least one fusion member configured to couple to the fusion implants.

As shown in the front and rear side views of FIGS. 3 and 4, the threaded apertures 18A-C may be countersunk into the body 16 at the rear portion of the fusion implant 10 (FIG. 4) and flush with the outer surface of the body 16 at the front portion of the fusion implant 10 (FIG. 3). The countersink of the threaded apertures 18A-C may include respective conical or conical-like grooves 36 about each threaded aperture 18A-C extending from the outer surface of the body 16 to the threaded apertures 18A-C. The grooves 36 may be of an oblong or other non-circular shape because such grooves 36 may be formed in the body 16 on an angle with respect to the outer surface of the body 16, and thus the longitudinal axis X-X as well (i.e., the axis of the grooves 36 not being formed normal to the outer surface of the body 16). In the illustrated embodiment, the angle axis of the grooves 36 is substantially aligned with the axis of the threaded apertures 18A-C. The grooves 36 may act to guide or reposition a fusion member, such as a bone screw, that is not aligned and/or oriented with the position and orientation of the threaded apertures 18A-C into proper alignment and/or orientation therewith so the fusion member can engage the internal threads. As such, grooves 36 that define axes substantially aligned with the axes of the internally threaded apertures 18A-C may be particularly advantageous. The grooves 36 may or may not be considered part of the internally threaded apertures 18A-C.

Figure 5:
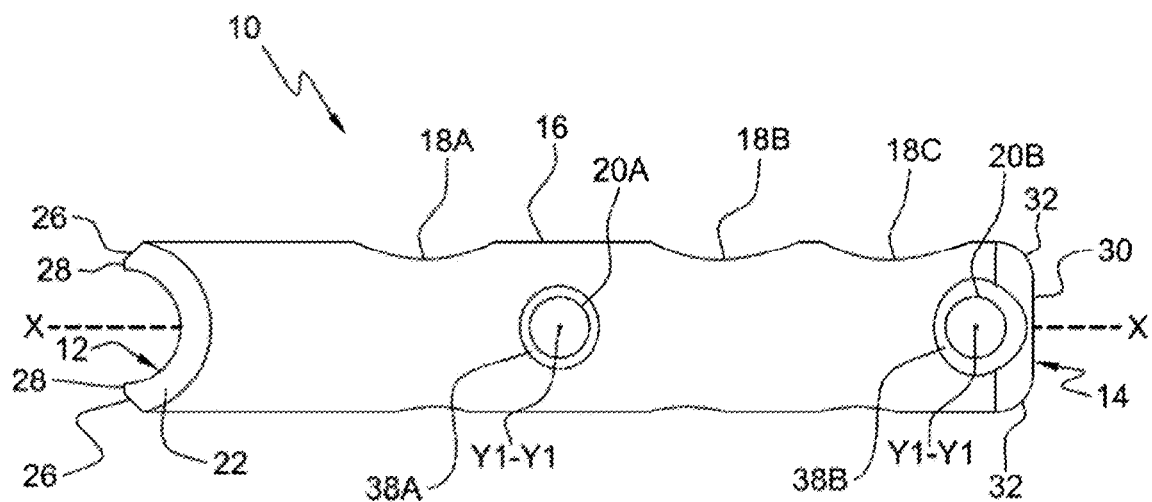
FIG. 5 is a first side view of the fusion implant of FIG. 1.
Figure 6:
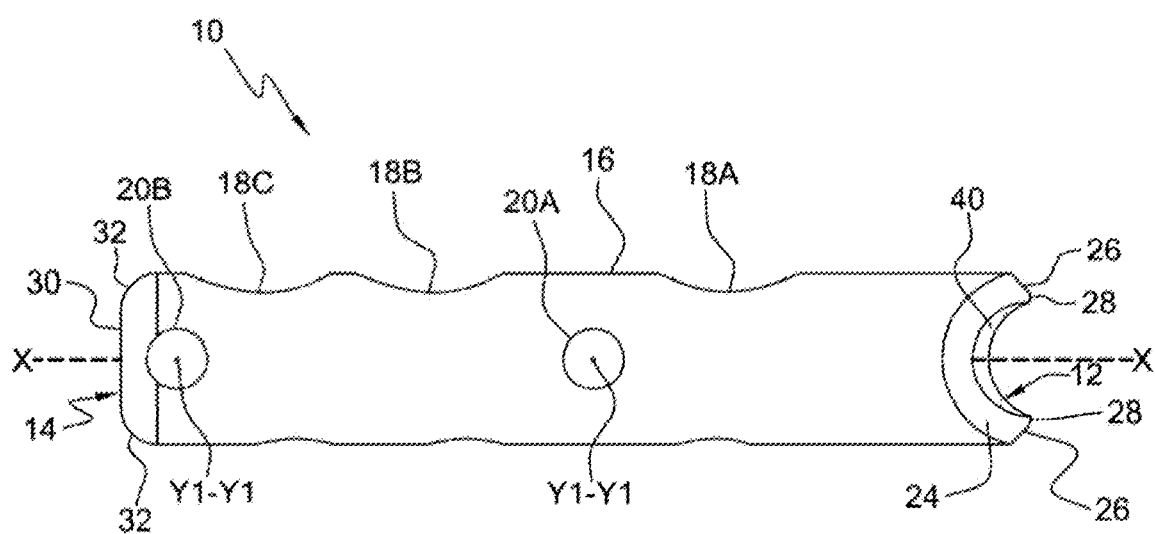
FIG. 6 is a second side view of the fusion implant of FIG. 1.

Similarly, as shown in the top and bottom side views of FIGS. 5 and 6, the non-threaded apertures 20A, 20B may also be countersunk into the outer surface body 16 at the top portion of the fusion implant 10 (FIG. 5), but flush with the outer surface of the body 16 at the bottom portion of the fusion implant 10 (FIG. 6). The countersink of the non-threaded apertures 20A, 20B may also include conical or conical-like grooves 38 about each aperture 20A, 20B extending from the outer surface of the body 16 to the non-threaded apertures 18A-C. The axis of the grooves 38 may be substantially aligned with the axes Y1-Y1 of the non-threaded apertures 20A, 20B. The grooves 38 may act to guide or reposition a temporary or permanent bone anchor, such as a k-wire, that is not completely aligned or oriented with the position and orientation of the non-threaded apertures 20A, 20B into alignment and orientation therewith so the bone anchor passes therethrough. As such, grooves 38 that define axes substantially aligned with the axes Y1-Y1 of the non-threaded apertures 20A, 20B may be particularly advantageous. The grooves 38 may or may not be considered part of the non-threaded apertures 20A, 20B.

FIG. 7 shows a front sectional view of the fusion implant 10 taken along a plane that is defined by the axes Y1-Y1 of the first and second non-threaded apertures 20A, 20B and the longitudinal axis X-X of the body 16. As shown in FIG. 7, the first and second non-threaded apertures 20A, 20B may extend linearly laterally through the body 16 such that their axes Y1-Y1 intersect with the longitudinal axis X-X of the body 16 at an angle .theta.2 (i.e., the non-threaded apertures 20A, 20B extend through the entire thickness of the body 16). In the illustrated embodiment, the non-threaded apertures 20A, 20B extend perpendicularly to the longitudinal axis X-X of the body 16, and therefore the angle .theta.2 between their axes Y1-Y1 and the longitudinal axis X-X shown is about 90 degrees. As also shown in FIG. 7, the threaded apertures 20A-C may be aligned along a plane extending normally to the axes Y1-Y1 of the non-threaded apertures and through the longitudinal axis X-X of the body 16, and therefore positioned about 90 degrees about the body 16 from the axes Y1-Y1 of the non-threaded apertures 20A, 20B. Stated differently, in the illustrated embodiment, the sides of the body 16 which the non-threaded apertures 20A, 20B extend between are spaced about 90 degrees about the longitudinal axis from the sides of the body 16 which the threaded apertures 20A-C extend between.

Figure 8:
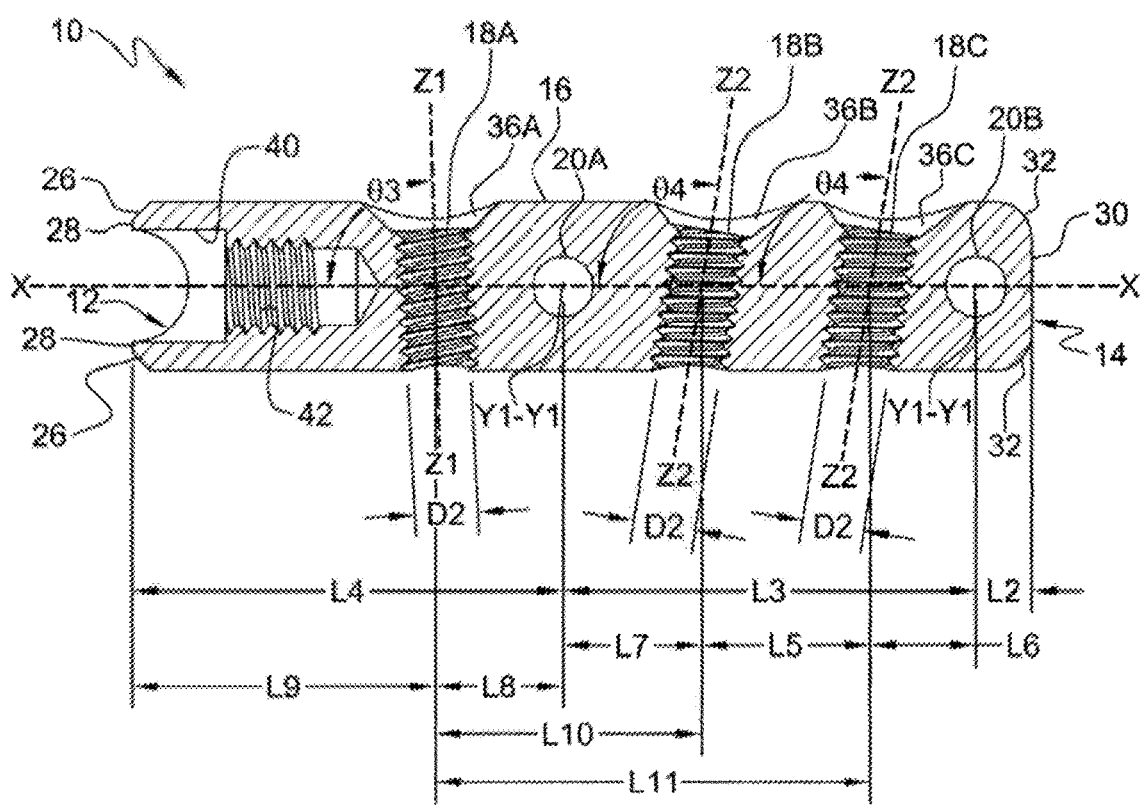
FIG. 8 is a second cross-sectional side view of the fusion implant of FIG. 1 taken along a plane defined by the longitudinal axis and the axes of the threaded-threaded apertures of the fusion implant.

FIG. 8 shows a top sectional view of the fusion implant 10 taken along a plane normal to the axes Y1-Y1 of the non-threaded apertures 20A, 20B and through the longitudinal axis X-X of the body 16. As shown in FIG. 7, the internally threaded apertures 18A-C may extend linearly laterally through the body 16 such that their respective axes Z1-Z1, Z2-Z2 and Z2-Z2 extend along a plane that passes through the longitudinal axis X-X of the body 16 (i.e., the internally threaded apertures 18A-C extend through the entire thickness of the body 16). In such a configuration, the plane defined by the axes Z1-Z1, Z2-Z2 and Z2-Z2 of the internally threaded apertures 18A-C, respectively, may be normal to the axes Y1-Y1 of the non-threaded apertures 20A, 20B, as described above. Therefore, the sides of the body 16 which the axes Z1-Z1, Z2-Z2 and Z2-Z2 of the threaded apertures 20A-C extend through are spaced about 90 degrees about the longitudinal axis from the sides of the body 16 which the axes Y1-Y1 of the non-threaded apertures 20A, 20B extend through. The axes Z1-Z1, Z2-Z2 and Z2-Z2 of the internally threaded apertures 18A-C may angularly extend through the longitudinal axis X-X of the body 16, such as extending at respective angles .theta.3, .theta.4, .theta.4 with respect to the rear surface and the first end 12 of the body 16, as illustrated in FIG. 8.

As explained further below, the threaded apertures 18A-C may be configured to engage with fusion members, such as bone screws, to fuse adjacent bones to one another. As a result, the respective angles .theta.3, .theta.4 and θ4 of the axes Z1-Z1, Z2-Z2 and Z2-Z2 of the threaded apertures 18A-C may vary and depend upon the particular target fusion bones. For example, in the illustrated embodiment the fusion implant 10 is particularly suited for insertion into the hammate and capitate bones of the wrist for fusion of the triquetral and lunate bones, respectively, thereto. As such, the axis Z1-Z1 of the first threaded aperture 18A adjacent the first end 12 is set at an angle .theta.3 of about 87 degrees with the longitudinal axis X-X of the body 16 with respect to the rear side and the first end 12 of the body 16 (i.e., the axis Z1-Z1 of the first threaded aperture 18A extends away from the first end 12 as it extends from the rear side to the front side of the body 16), and the axes Z2-Z2 of the first and second threaded apertures 18B, 18C, respectively, adjacent the second end are set at an angle .theta.4 of about 99 degrees with the longitudinal axis X-X of the body 16 with respect to the rear side and the first end 12 of the body 16 (i.e., the axes Z1-Z1 of the first and second threaded apertures 18B, 18C, respectively, extend away from the second end 14 as they extend from the rear side to the front side of the body 16).

In some embodiments, the axis Z1-Z1 of the first threaded aperture 18A adjacent the first end 12 is set along the plane shown in FIG. 7 and preferably at an angle .theta.3 with the longitudinal axis X1-X1 of the body with respect to the rear side and first end 12 of the body 16 within a range of about 80 degrees and about 95 degrees, and more preferably between a range of about 82 degrees and about 93 degrees. In some embodiments, the axes Z2-Z2 of the second and third threaded apertures 18B and 18C, respectively, adjacent the second end 14 are set along the plane shown in FIG. 7 and preferably at an angle .theta.4 with the longitudinal axis X1-X1 of the body 16 with respect to the rear side and the tip 12 of the body 16 within a range of about 92 degrees and about 106 degrees, and more preferably between a range of about 94 degrees and about 104 degrees.

Therefore, in the illustrated embodiment, the axes Y1-Y1 of the non-threaded apertures 20A, 20B are parallel to each other, and the axes Z2-Z2 of the first and second threaded apertures 18B and 18C are parallel to each. Further, the axis Z1-Z1 of the first threaded aperture 18A is planar with the axes Z2-Z2 of the first and second threaded apertures 18B and 18C, and such plane is normal axes Y1-Y1 of the non-threaded apertures 20A, 20B. Stated differently, a plane extending between the axes Y1-Y1 of the non-threaded apertures 20A, 20B (plane of FIG. 7) is perpendicular with respect to a plane extending through the axes Z1-Z1, Z2-Z2, Z2-Z2 of the threaded apertures 18A-C(plane of FIG. 8).

The internal or female threads of the threaded apertures 18A-C may be configured to interact with a fusion member, such as a bone screw, to couple the fusion member to the device 10. Thus, if the fusion implant 10 is implanted in one or more bones, and multiple fusion members are implanted into adjacent bones and into engagement with the threaded apertures 18A-C, the fusion implant 10 and threaded apertures 18A-C act in concert to fuse the adjacent bones to one another. The characteristics of the threading of the threaded apertures 18A-C, such as thread lead, may thus be dependent upon, or related to, the characteristics of the threading of fusion members. In some embodiments, the internal threading of the threaded apertures 18A-C is a two-start, right handed threading, when viewed from the grooves 36 or rear side of the body 16, that includes an about 0.08 inch nominal diameter, a thread lead of about 0.03 inches, and a thread pitch of about 0.015 inches. In the illustrated embodiment, the internal threading of the threaded apertures 18A-C is a two-start, right handed threading (when viewed from the grooves 36 or rear side of the body 16) that includes an about 2 millimeter nominal diameter, a thread lead of about 0.8 millimeters, and a thread pitch of about 0.4 millimeters. In alternative embodiments, locking mechanisms other than internal threads may be used. For example, in some embodiments the apertures 18A-C do not include internal threads, rather they are configured to mate with fusion members through alternative locking mechanisms, such as key and slot agreement, detent mechanism, friction taper and interference fit. In addition, the use of different materials (metals or biologics) between the fusion implant 10 and fusion members could facilitate the locking of the fusion devices and resultant securement.

The non-threaded apertures 20A, 20B may be configured to interact with a temporary or permanent anchor member to temporarily or permanently couple, at least in part, the fusion implant 10 to bones and/or the fusion implant 10 or target fusion bones to an instrument. For example, in the illustrated embodiment, the non-threaded apertures 20A, 20B are shaped and sized to accept a k-wire therethrough (a temporary bone anchor). In the illustrated embodiment, the diameter of the non-threaded apertures 20A, 20B is sized to receive an industry standard 1.6 millimeter k-wire therethrough, and therefore the diameter of the non-threaded apertures 20A, 20B is at least about 0.63 inches.

As shown in FIG. 8, the non-threaded apertures 20A, 20B and threaded apertures 18A-C can be spaced along the longitudinal axis X-X of the body 16 (and thus along the fusion implant 10 itself) between the first end 12 and the second end 14. The number and relative positioning of the non-threaded apertures 20A, 20B and threaded apertures 18A-C may vary and depend upon the particular bone structures which are desired to be fused. For example, in the illustrated embodiment the fusion implant 10 is particularly well suited for insertion into the hammate and capitate bones of the wrist for fusion of the triquetral and lunate bones, respectively, thereto, with the use of bone screws. As shown in FIG. 8, for such a use, the fusion implant 10 may include three internally threaded apertures 18A-C and two non-threaded apertures 20A, 20B. The non-threaded apertures 20A, 20B may be arranged such that a first non-threaded aperture 20A is located in an intermediate portion of the body 16 and a second non-threaded aperture 20B is located adjacent the second end 14 of the body 16. In the illustrated embodiment, the axis Y1-Y1 of the intermediate first non-threaded aperture 20A is axially spaced a distance L4 of about 0.45 inches from the outer most surface of the first end (e.g., first end tip surfaces 28), the axis Y1-Y1 of the second non-threaded aperture 20B adjacent the second end 14 is axially spaced from the outer most surface of the second end 14 (e.g., tip surface 30) a distance L2 of about 0.06 inches, and the axial distance L3 between the axis Y1-Y1 of the first non-threaded aperture 20A and the axis Y1-Y1 of the second non-threaded aperture 20B is about 0.43 inches.

As also shown in FIG. 8, for such a use second and third internally threaded apertures 18B, 18C may be paired together and positioned between the first and second non-threaded apertures 20A, 20B, such that the third threaded aperture 18C is adjacent the second non-threaded aperture 20B that is adjacent the first end 14, and the second threaded aperture 18B is adjacent the intermediate first non-threaded aperture 20A. In the illustrated embodiment, the axes Z2-Z2 of the pair of parallel second and third threaded apertures 18B and 18C are axially spaced from one another a distance L5 of about 0.18 inches, the axial distance L6 between the axis Z2-Z2 of the third threaded aperture 18C at the point where it intersects the longitudinal axis X-X of the body 16 and the axis Y1-Y1 of the second non-threaded aperture 20B is about 0.11 inches, and the axial distance L7 between the axis Z2-Z2 of the second threaded aperture 18B at the point where it intersects the longitudinal axis X-X of the body 16 and the axis Y1-Y1 of the first non-threaded aperture 20A is about 0.145 inches.

As also shown in FIG. 8, the first threaded aperture 18A may be posited between the intermediate first non-threaded aperture 20A and the first end 12. In the illustrated embodiment, the axial distance L8 between the axis Z1-Z1 of the first threaded aperture 18A at the point where it intersects the longitudinal axis X-X of the body 16 and the axis Y1-Y1 of the intermediate first non-threaded aperture 20A is about 0.13 inches. Also, in the illustrated embodiment the axial distance L9 between the axis Z1-Z1 of the first threaded aperture 18A at the point where it intersects the longitudinal axis X-X of the body 16 and the outer most point of the first end 12 (e.g., first end tip surfaces 28) is about 0.32 inches. Still further, in the illustrated embodiment the axial distance L10 between the axis Z1-Z1 of the first threaded aperture 18A and the axis Z2-Z2 of the second threaded aperture 18B at the point where they intersect the longitudinal axis X-X of the body 16 is about 0.28 inches, and the axial distance L11 between the axis Z1-Z1 of the first threaded aperture 18A and the axis Z2-Z2 of the third threaded aperture 18C at the point where they intersect the longitudinal axis X-X of the body 16 is about 0.46 inches.

As shown best in the cross-sectional views of FIGS. 7 and 8, the first end 12 includes a substantially cylindrical aperture 40 extending into the body 16 about longitudinal axis X-X of the body 16. The cylindrical aperture 40 may include an internally threaded portion 42 positioned at an intermediate portion of the cylindrical aperture 40. The internally threaded portion 42 may define a diameter that is less than the diameter of the outer non-threaded portion of the cylindrical aperture 40 that is adjacent the first end 12. The cylindrical aperture 40 may be used to couple the first end 12 of the fusion implant 10 to an instrument in a predefined orientation of the fusion implant 10.

Figure 9:
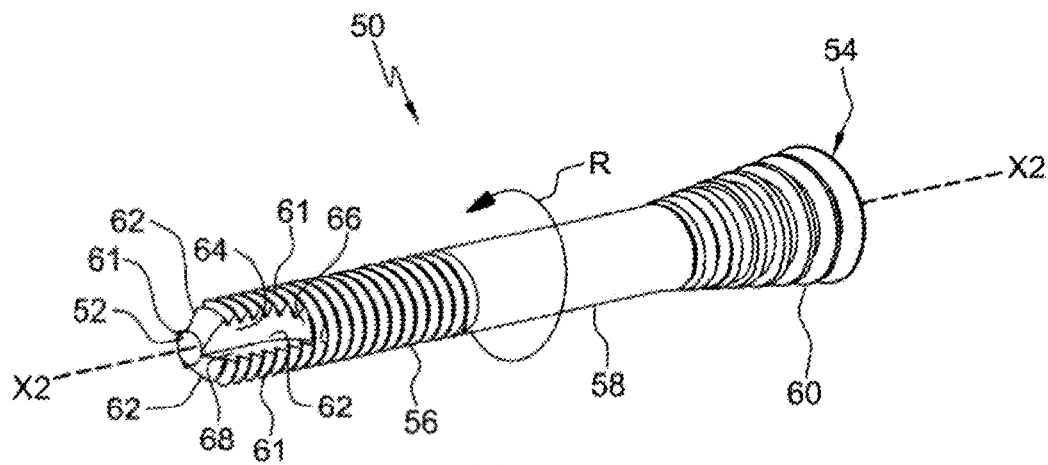
FIG. 9 is a rear elevational perspective view of a first exemplary embodiment of a fusion member of the present invention.
Figure 10:
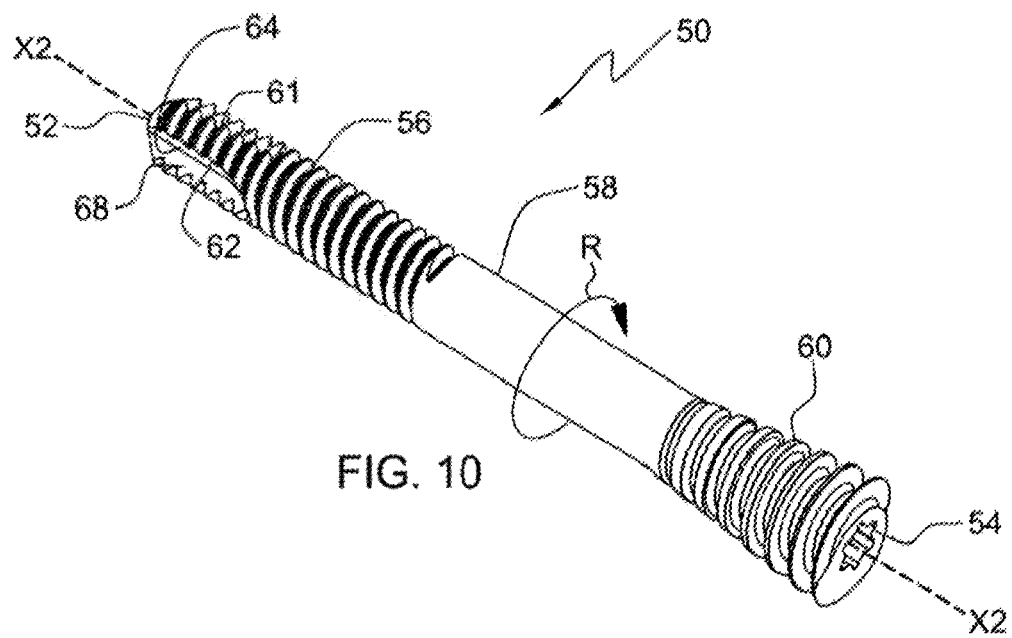
FIG. 10 is a front elevational perspective view of the fusion implant of FIG. 9.
Figure 11:
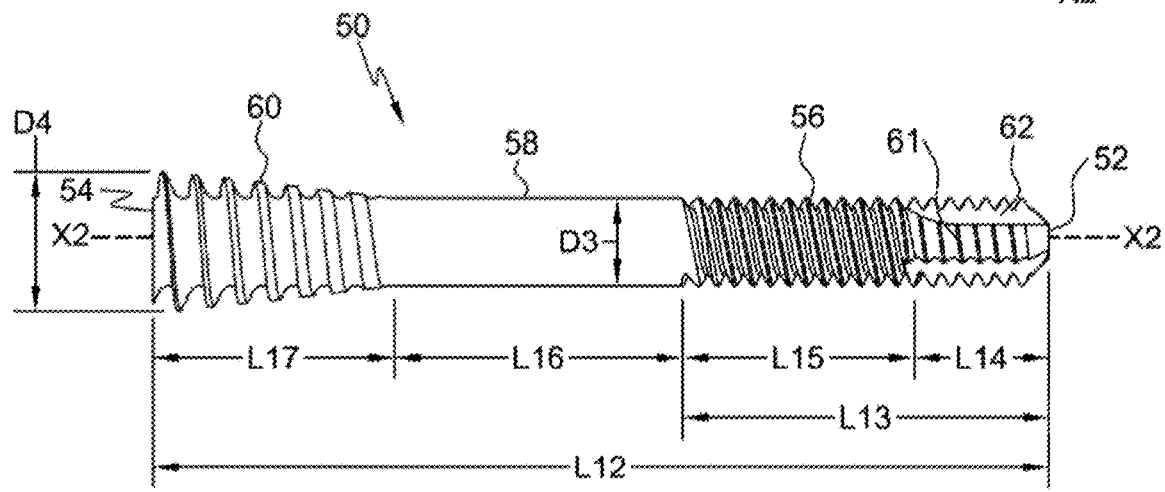
FIG. 11 is a side view of the fusion implant of FIG. 9.

As discussed above, the fusion implant 10 may be paired with fusion members, such as bone screws, to form a fusion device capable of fusing adjacent bones. An exemplary fusion member is shown in FIGS. 9-11. Exemplary fusion member 50 of FIGS. 9-11 is an externally threaded bone screw. Exemplary bone screw 50 may preferably be configured to couple to the threaded apertures 18A-C to form a fusion device (as shown in FIGS. 13-19), such as a bone fusion device. For example, the fusion implant 10 may be implanted into first and second adjacent bones, and a bone screw 50 may be implanted through each of third and fourth bones adjacent the first and second bones, respectively, and engaged with one of the threaded apertures 18A-C of the fusion implant 10 to fuse the first and second bones to the third and fourth bones, respectively.

In some embodiments, exemplary bone screw 50 is a self-tapping screw configured to cut threads and advance into bone through rotation of the screw 50, as shown in FIGS. 9-11. As shown in the illustrated bone screw 50, the bone screw 50 may include a tip 52 defining a first end of the bone screw 50 and a head 54 defining an opposing second end of the bone screw 50, and a longitudinal axis X2-X2 extending between the tip 52 and the head 54. The tip 52 may define a substantially flat circular surface, and the portion of the bone screw 50 adjacent the tip may narrow or taper to provide a tapered profile, as shown best in FIG. 9. In alternative embodiments, the tip 52 is radiused, curved or otherwise configured to provide a smooth tip surface void of sharp edges (other than the threads, for example). The head

54 may also define a substantially flat surface, but may include an aperture configured to engage a tool to apply rotational force to the bone screw 50 via the aperture. For example, in the illustrated embodiment show best in FIG. 10, the head 54 includes a flat surface with a hexagonal or hexalobe shaped aperture extending therein.

The bone screw 50 may define a cylindrical-like shank or body extending between the tip 52 and the head 54 and be substantially symmetrically disposed about the longitudinal axis X2-X2. The total axial length of the bone screw 50 measured from the tip 52 to the head 54, and the largest diameter of the screw 50, may vary depending upon the particular target fusion bones. As shown in FIG. 11, the illustrated bone screw 50 is particularly well suited for implantation into the lunate and hammate bones, and the triquetral and capitate bones, of the wrist and preferably defines a total axial length within the range of about 0.7 inch to about 1.2 inches, such as axial lengths L12 of about 0.71 inch, about 0.79 inch, about 0.87 inch, about 0.94 inch, about 1.02 inches, about 1.1 inches and about 1.18 inches. In some such embodiments the total axial length L12 of the bone screw more preferably ranges from about 18 millimeters to about 30 millimeters. In the illustrated embodiment, the total axial length L12 of the bone screw 50 is about 0.94 inch. In one embodiment, a fusion kit may include a plurality of bone screws 50 of differing axial lengths L12, such as a kit including bone screws 50 of axial lengths 12 from about from 0.7 inch to about 1.2 inches in about 0.8 inch increments. In some such embodiments the kit may further include at least one fusion implant 10 configured to couple to the bone screws 50.

As shown in FIGS. 9-11, the shank or body of the fusion member 50 may include a first threaded portion 56 adjacent the tip 52, a second threaded portion 60 adjacent the head 54, and an intermediate non-threaded portion 58 axially positioned between the first threaded portion 56 and the second threaded portion 60. The first threaded portion 56 adjacent the tip 52 may include male or exterior helical threading, and such exterior threading may include a double start or double lead thread and a self-tapping feature. As illustrated best in FIG. 9, the self-tapping feature may include at least one flute or relief 62 disposed into the periphery of the shank of the first threaded portion 56, such as three reliefs 62 symmetrically disposed about the axis X2-X2 of the fusion member 50. In such an embodiment including multiple reliefs 62, such, flutes or reliefs 62 interrupt the threaded portion 60 and the threading thereon to form interrupted threaded portions 61 therebetween.

The at least one relief 62 may axially extent partially along the axial length L13 of the first threaded portion 56 from the tip 52. For example, in the illustrated embodiment shown in FIG. 11, the axial length L13 of the first threaded portion 56 of the fusion member 50 is about 0.3 inch, and the axial length L14 of each of the three reliefs or flutes 62 is less than about 0.3 inch. In some embodiments, the axial length L13 of the first threaded portion 56 is preferably greater than about 10 percent, and less than about 90 percent, of the total axial length L12 of the fusion member 50, and more preferably greater than about 25 percent, and less than about 75 percent, of the total axial length L12 of the fusion member 50. Further, in some embodiments, the axial length L14 of each relief 62 is preferably greater than about 10 percent, and less than about 90 percent, of the axial length L13 of the first threaded portion 56, and more preferably greater than about 25 percent, and less than about 75 percent, of the axial length L13 of the first threaded portion 56. It is noted however, that the axial length L13 of the first threaded portion 56 and the axial length L14 of each relief 62 may depend upon, or at least be related to, the axial lengths of the other portions of the fusion member 50. Further, the axial length L13 of the first threaded portion 56, as well as the axial length of each relief 62, may depend upon, or at least be related to, a particular clinical need, injury, patient size and/or fusion implant, and therefore fusion members 50 including axial lengths L13 and L14 outside the ranges presented above may be desirable.

The intermediate portion of the at least one flute or relief 62 may be radiused to provide a smooth transition between the at least one relief 62 and the adjacent portion of the shank, such as a relief-free portion of the first threaded portion 56 in embodiments where the axial length of the at least one relief 62 is less than the axial length of the first threaded portion 56. For example, as shown in the illustrated embodiment in FIGS. 9-11, the trailing surface 64 of each relief 62, with respect to the direction of rotation R, may include a radiused portion 66 that transitions the junction of each relief 62 and the intermediate portion of the first threaded portion 56 that is void of the at least one relief 62. In one embodiment, the radius of the radiused portion 66 is about 0.08 inch.

The at least one relief 62 may also include a leading surface 68 that defines a leading edge extending between the leading surface 68 and the exterior of the adjacent interrupted portion 61, with respect to the direction of rotation R. In such an embodiment, the leading surface 68 may be angled with respect to the longitudinal axis X2-X2 such that an acute angle is formed between the leading surface 68 and the interrupted exterior threaded portion 61. The acute angle formed between the surfaces may facilitate the cutting of threads in bone via the leading edge when the screw 50 is applied to a bone surface and rotated in the direction of rotation R. During such a self-tapping process, the at least one flute or relief 62 may provide a cavity or channel in which bone chips, dust or other debris resulting from the self-tapping process can collect and thereby prevented from interfering with the self-tapping process.

As described above, the exterior threading of the first threaded portion 56 is provided helically along the first portion 56 with respect to a direction of rotation R about the axis X2-X2. In the illustrated embodiment, the exterior threading of the first threaded portion 56 is right-hand thread such that the threading causes the fusion member 50 to advance in a direction along the axis X2-X2 from the head 54 to the tip 52 upon clockwise rotation of the member 50 about the axis X2-X2. In an alternative embodiment, the exterior threading of the first threaded portion 56 is a left-hand thread. It is noted, however, that the particular handedness of the exterior threading of the first threaded portion 56 of the fusion member 50 is dependent only with respect to the handedness of the internal threading of the internally threaded apertures 18A-C of the fusion implant 10, as the fusion member 50 and fusion implant 10 are preferably configured to threadably coupled to one another via the internally threaded apertures 18A-C.

The exterior or male threading of the first threaded portion 56 may be a single, double or other multiple start threading and may include a constant for varying diameter, pitch and lead. For example, in one embodiment the threading of the first threaded portion 56 is a double start threading that includes an about 0.08 inch diameter, a thread lead of about 0.03 inches, and a thread pitch of about 0.015 inches. In the illustrated embodiment, the threading of the first threaded portion 56 is a two-start, right handed threading (when viewed from the head 54) that includes an about 2 millimeter nominal diameter, a thread lead of about 0.8 millimeter, and a thread pitch of about 0.4 millimeter. In some embodiments, the threading of the first threaded portion 56 is a machine type threading. It is noted, however, that the type, diameter, pitch, length, number of starts, thread profile and any other characteristic of the threading of the first threaded portion 56 may be dependent upon, or at least related to, the respective characteristic of the threading of the internally threaded apertures 18A-C of the fusion implant 10. As such, the exterior threading of the first threaded portion 56 of the bone screw 50 and the internal threading of the threaded apertures 18A-C of the fusion implant 10 of the illustrated embodiment are configured to mate with one another, and therefore both define two-start, right handed threading (when viewed from the head 54 of the fusion member 50 and from the rear side or grooves 36 of the implant 10) that includes about a 2 millimeter nominal diameter, a thread lead of about 0.8 millimeters, and a thread pitch of about 0.4 millimeters. In some such embodiments, the diameter is about 0.076 inch.

The portion of the bone screw 50 that is positioned adjacent the first threaded portion 56 may be a non-threaded portion 58, as shown in FIGS. 9-11. The non-threaded portion 58 may define a relatively smooth, uninterrupted outer surface of a diameter D2. In some embodiments, the non-threaded portion 58 may include some type of macro, micro or nano texture, structure or coating. As shown in FIG. 11, the non-threaded portion 58 may extend along the longitudinal axis X2-X2 of the bone screw for an axial length L16. In some embodiments, the axial length L16 of the non-threaded portion 58 is greater than the axial length of the first threaded portion 56. In some embodiments, the axial length L13 of the non-threaded portion 58 is preferably greater than about 10 percent, and less than about 90 percent, of the total axial length L12 of the fusion member 50, and more preferably greater than about 25 percent, and less than about 75 percent, of the total axial length L12 of the fusion member 50. It is noted however, that the axial length L16 of the non-threaded portion 58 may depend upon, or at least be related to, the axial lengths of the other portions of the fusion member 50. Further, the axial length L16 of the non-threaded portion 58 may depend upon, or at least be related to, a particular clinical need, injury, patient size and/or fusion implant, and therefore fusion members 50 including axial lengths L16 outside the ranges presented above may be desirable. As another example, in some exemplary embodiments the total axial length L12 of the bone screw ranges from about 18 millimeters to about 30 millimeters in about 2 millimeter increments, and such 2 millimeter axial length increments are provided by 2 millimeter differences in the axial length of the non-threaded portion 58 (i.e., the length L13 of the first threaded portion 56 and the length L17 of the second threaded portion 60 remain the same).

As shown in FIGS. 9-11, the fusion member 50 may include a second threaded portion 60 adjacent the head 54 and non-threaded portion 58. The second threaded portion 60 may include male or exterior helical threads. The exterior or male threading of the second threaded portion 60 may be a single, double or other multiple start threading, and may include constant or varying diameter, pitch and lead. In some embodiments, the threading is a cancellous type threading (e.g., a coarse thread threaded to only the first third of the length of the fusion member 50).

In some embodiments, the thread lead is dependent upon, or related to, the thread lead of the exterior threading of the first threaded portion and the internal threading of the internally threaded apertures 18A-C of the fusion implant 10. In some such embodiments, the thread lead of the threading of the second threaded portion 60 is less than the thread lead of the threading of the first threaded portion 56 and the internally threaded apertures 18A-C. Stated differently, in some embodiments the thread lead of the threading of the first threaded portion 56 (i.e., the threading adjacent the tip 52) and the internally threaded apertures 18A-C may be greater than the thread lead of the threading of the second threaded portion 60 (i.e., the threading adjacent the head 54). In some such embodiments where the threading of the second threaded portion 60 is a single start thread, the thread lead and pitch are less than the thread lead of the first threaded portion 56 and the internally threaded apertures 18A-C (because the thread lead and pitch are the same). For example, in one embodiment the threading of the second threaded portion 60 is a single start threading that includes an about 0.027 inch thread lead and thread pitch, and the threading of the internally threaded apertures 18A-C and second threaded portion 56 include an about 0.03 inch thread lead. In the illustrated embodiment, the threading of the second threaded portion 60 is a single-start, right handed threading (when viewed from the head 54) that includes an about 0.7 millimeter thread lead and pitch.

In some embodiments, the axial length L17 of the second threaded portion 60 is less than the axial lengths L16, L13 of the non-threaded portion 58 and the first threaded portion 56. In some embodiments, the axial length L17 of the second threaded portion 60 is preferably greater than about 10 percent, and less than about 90 percent, of the total axial length L12 of the fusion member 50, and more preferably greater than about 25 percent, and less than about 75 percent, of the total axial length L12 of the fusion member 50. It is noted however, that the axial length L17 of the second threaded portion 60 may depend upon, or at least be related to, the axial lengths of the other portions of the fusion member 50. Further, the axial length L17 of the second threaded portion 60 may depend upon, or at least be related to, a particular clinical need, injury, patient size and/or fusion implant, and therefore fusion members 50 including axial lengths L17 outside the ranges presented above may be desirable. In the illustrated embodiment shown in FIGS. 9-11, the axial length L17 of the second threaded portion 60 is about 0.2 inch.

The second threaded portion 60 may include a compression wedge or tapered profile extending from the head 54 to the non-threaded portion 58, as shown in FIGS. 9-11. In some such embodiments, the major diameters formed by the outer edges of the threads and the minor diameters formed by the gullets between the threads both taper (i.e., tapered threading). In some other such embodiments, only one of the major and minor diameters of the threading of the threaded portion 60 tapers. In the illustrated embodiment, the major diameter of the threads tapers from the head 54 to the non-threaded portion 58, but the minor diameter defined by the gullets remains constant along the axial length L17 of the second threaded portion 60. The tapering of the major diameter of the threads of the second threaded portion 58 may be formed by threads of differing thread profile with differing thread depth or percentage of thread. For example, as shown in the illustrated embodiment, the threads of the second threaded portion 60 may be machined to define progressively shorter thread depths and wider crests which are angled with respect to the longitudinal axis X2-X2 of the fusion member 50 from the head 54 to the non-threaded portion 58 to form the tapered profile. In the illustrated embodiment, the major diameter of the threads of the second threaded portion 60 taper at an angle of about 7 degrees with respect to the longitudinal axis X2-X2 of the fusion member 50. In some embodiments, the taper of the major diameter of the threads of the second threaded portion 60 preferably ranges from a minimum taper angle that will effectively provide a "wedge" characteristic that prevents the fusion member 50 from being pulled through the particular bone that the second threaded portion 60 is implanted in, to a maximum taper angle that will effectively allow the fusion member 50 to be implanted at least partially through a fusion bone 50 and rotate therein to, eventually, achieve fusion.

As shown best in FIGS. 10 and 11, the second threaded portion 60 is adjacent the head 54 of the fusion member 50. The head 54 may include a lateral surface defining the end or most axial surface of the fusion member 50 opposing the tip 52. In the illustrated embodiment, the head 54 includes a planar surface that is normal to the longitudinal axis X2-X2 of the fusion member 50. As discussed above, the head 54 may include an aperture or other mechanism capable of applying torque to the fusion member 50. The threading of the second threaded portion 60 may continue to the head surface 54 such that the major diameter of the threads decreases at is approaches the head 54. In an alternative embodiment, the head 50 may not be a lateral surface, but may be a member defined along the longitudinal axis X2-X2 and positioned adjacent the second threaded portion 50.

Fusion member 50 embodiments including such a greater thread lead of the threading adjacent the tip 52 (e.g., the first threaded portion 56) and the threading of the internally threaded apertures 18A-C of the fusion implant 10 as compared to threading adjacent the head 54 (e.g., the second threaded portion 60), may be advantageous for facilitating bone fusion because such a thread arrangement may act to pull adjacent bones into contact with each other and, depending upon the level of rotation of the fusion member, apply a compressive force or load to the joint between the bone surfaces contacting each other. For example, when a fusion implant 10 is implanted into a first bone, such a fusion member 50 can be rotatably advanced into an adjacent but spaced second bone to such a degree that the second threaded portion 60 is in engagement with the first bone and the first threaded portion 56 has partially or primarily passed through the second bone and into the first bone and engagement with an internally threaded aperture 18A-C of the fusion implant 10 implanted therein. In such a position, further clockwise rotation of the fusion member 50 results in the fusion member 50 traveling farther along its longitudinal axis X2-X2 per unit of revolution through the first bone and implant 10 than in the second bone (because the differences of thread lead of the first threaded portion 56 and second threaded portion 60). As a result, rotation of the fusion member 50 acts to pull the second bone (via the threads of the second threaded portion 60) towards the first bone to reduce the space between adjacent surfaces of the bones.

After the space between the first and second bones is eliminated and the adjacent surfaces meet (i.e., first and second bones in abutment), further rotation of the fusion member 50 will apply compressive forces to the joint between the adjacent surfaces because the second threaded portion 60 engages the inner surfaces of second bone and thereby resists being pulled through the second bone as the first threaded 56 portion advances in the first bone and fusion implant 10. The wedge or taper shape of the second threaded portion 60 may facilitate such engagement with the interior of the second bone that prevents the second threaded portion 60 from being pulled therethrough, and application of the compressive force. As a result, the thread leads and the relative lengths of the first and second bones, the first threaded portion 56, the second threaded portion 60 and the non-threaded portion 58 must be properly proportioned to utilize the fusion member 50 and implant 10 to provide a secure construct that facilitates fusion of the first and second bones. For example, the above mentioned aspects must be properly proportioned or related such that the first threaded portion 56 does not pass through the implant 10 before the space between the target fusion bones is eliminated, the space between the target fusion bones is not eliminated before the fusion member 50 engages the fusion implant 10, the first and second threaded portions 56, 60 do not substantially engage the same bone at the same time (the non-threaded portion 58 spans the joint), and the fusion member 50 does not strip out or fail to engage the first bone, second bone or fusion implant 10.

Figure 12:
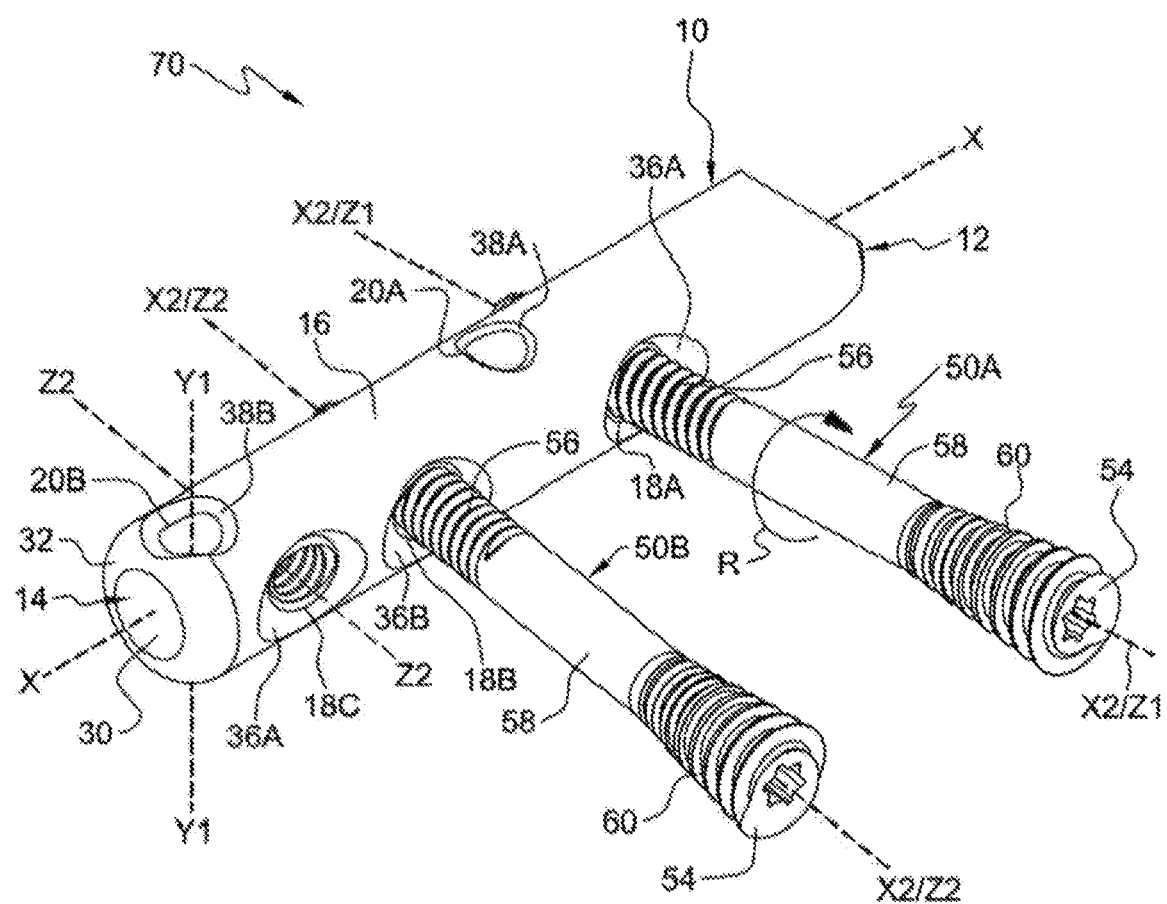
FIG. 12 is a rear elevational perspective view of an exemplary embodiment of a fusion device of the present invention.
Figure 13:
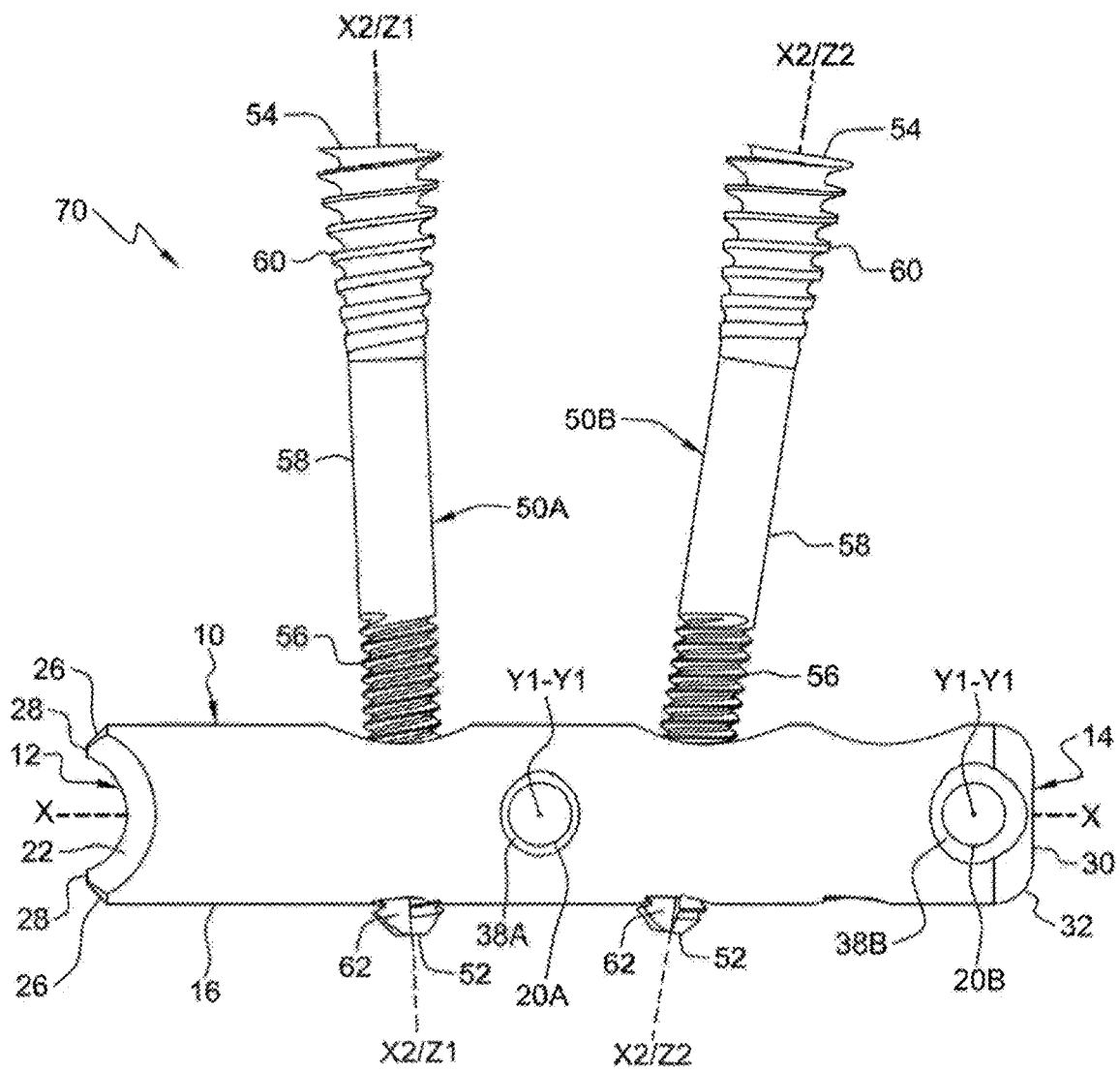
FIG. 13 is a top view of the fusion device of FIG. 12.
Figure 14:
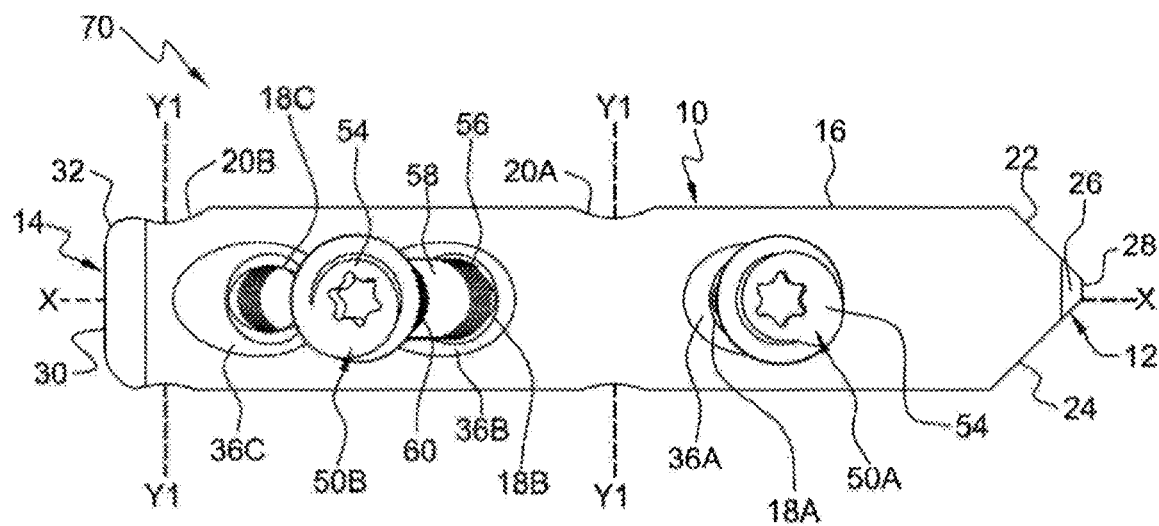
FIG. 14 a front view of the fusion device of FIG. 12.

As shown in FIGS. 12-13, an exemplary fusion device 70 may include a fusion implant and at least two fusion members, such as the illustrated exemplary fusion implant 10 and illustrated exemplary fusion member 50 described above. A first fusion member 50A may be threadably engaged with the implant 10 via the first internally threaded aperture 18A adjacent the first end or tip 12 and a second fusion member 50 may be threadably engaged with the implant 10 via the second internally threaded aperture 18B intermediately positioned in the body 16. The third internally threaded aperture 18C adjacent the second end 14 may or may not include a third fusion member 50. As illustrated best in FIGS. 11 and 13, in such an arrangement or construct the axes X2-X2 of the first and second fusion members 50A, 50B will substantially align with the axes Z1-Z1, Z2-Z2 of the first and second internally threaded apertures 18A, 18B, respectively. Therefore, in such a construct the description presented above with respect to the illustrated and described positioning, arrangements, orientations and the like of the first and second internally threaded apertures 18A, 18B and/or their respective axes Z1-Z1, Z2-Z2 equally applies to the first and second fusion members 50A, 50B and is not repeated herein with respect to the fusion members 50A, 50B for brevity purposes. Similarly, the description presented above with respect to the positioning, arrangements, orientations and the like of the first and second non-threaded apertures 20A, 20B and/or their axes Y1-Y1 with respect to each other and the first and second internally threaded apertures 18A, 18B equally applies to the first and second fusion members 50A, 50B and is not repeated herein with respect to the fusion members 50A, 50B for brevity purposes.

As shown in FIG. 13, the first and second fusion members 50A, 50B may be positioned within the first and second internally threaded apertures 18A, 18B (e.g., via rotation) such that the first threaded portions 56 thereof partially pass through the apertures 18A, 18B and body 16 of the implant 10. In such an arrangement, the first fusion member 50A may be engaged with first aperture 18A to a degree that is more, less or the same as the degree to which the second fusion member 50B is engaged with the second aperture 18B. Further, the first threaded portions 56 may be positioned on both the front and rear sides of the body 16, or may be positioned only on the rear side of the body 16 (in addition to within the internally threaded apertures 18A, 18B). In some other embodiments, the first threaded portions 56 may be positioned only on the front side of the body (in addition to within the internally threaded apertures 18A, 18B). In the illustrated embodiment, the first threaded portion 56 of the first and second fusion members 50A, 50B partially pass through the first and second internally threaded apertures 18A, 18B to the same extent as each other and to such an extent that a portion of the flutes or reliefs 62 are positioned on the front side of the body 16 and the remaining portions of the first and second fusion members 50A, 50B are positioned on the rear side of the body (besides the portions that are positioned within the first and second apertures 18A, 18B).

Figure 15:
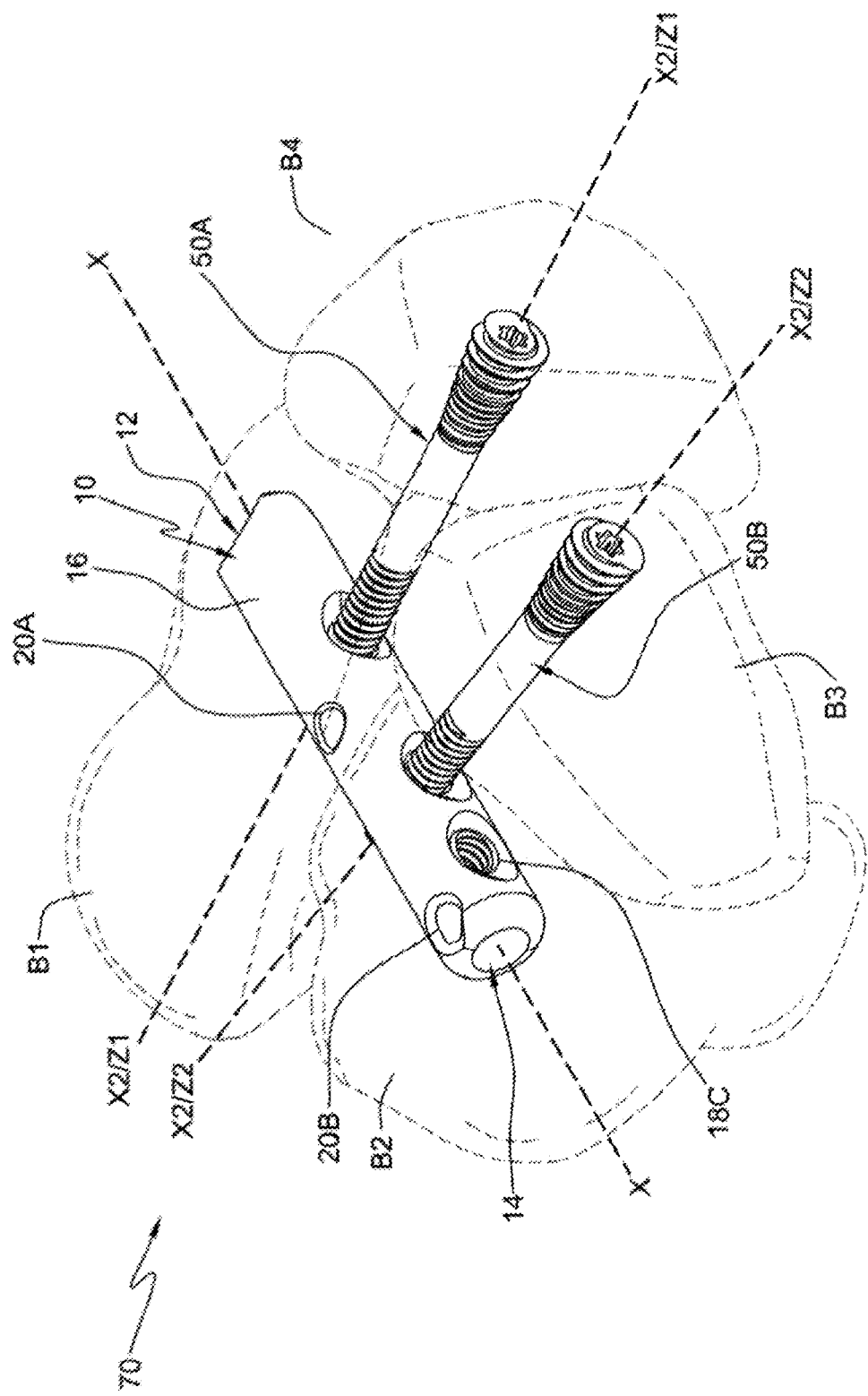
FIG. 15 is a rear elevational perspective view the fusion implant of FIG. 12 implanted in exemplary bones of an upper extremity.
Figure 16:
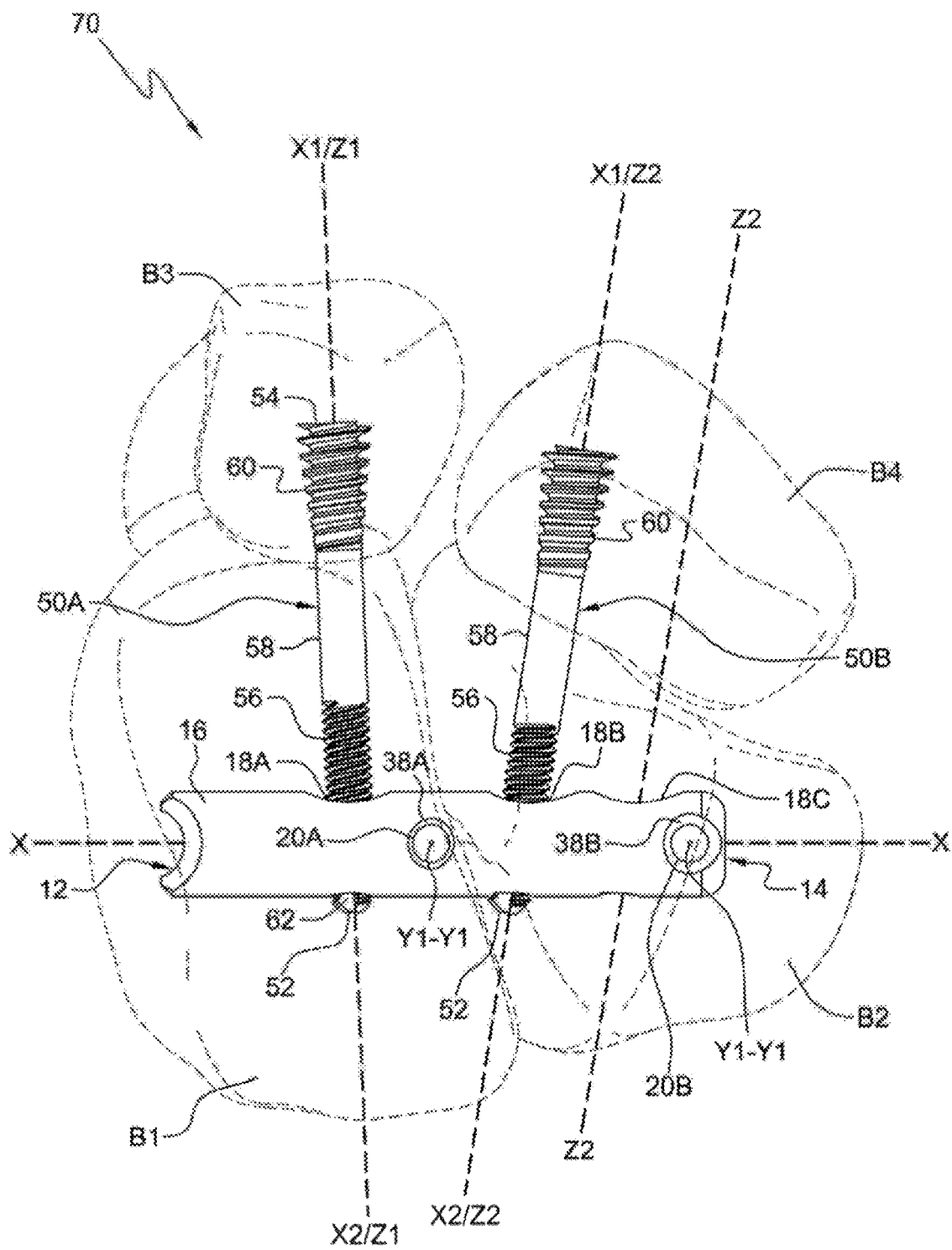
FIG. 16 is a top view the fusion implant of FIG. 12 implanted in the exemplary bones of an upper extremity of FIG. 15.

Exemplary fusion device 70 may be well suited for providing or facilitating fusion of adjacent bones, as shown in FIGS. 15 and 16. The fusion implant 10 may be particularly well suited for implantation into first B1 and second B2 adjacent bones, the first fusion member 50A may be particularly well suited for implantation into a third bone B3 adjacent the first bone B1 and into the first bone B1 (and into the first internally threaded aperture 18A), and the second fusion member 50B may be particularly well suited for implantation into a fourth bone B4 adjacent both the second bone B2 and the third bone B3 and into the second bone B2 (and into the second internally threaded aperture 18B). In such a construct, the fusion device 70 provides or facilitates fusion of at least the first bone B1 and third bone B3 (via the first fusion member 50A and implant 10), and the second bone B2 and fourth bone B4 B3 (via the second fusion member 50B and implant 10). In the illustrated embodiment, the first bone B1 is the capitate bone, the second bone B2 is the hammate bone, the third bone B3 is the lunate bone and the fourth bone B4 is the triquetral bone. In the illustrated embodiment, the device 10 provides fusion of the lunate and capitate bones, and the triquetral and hammate bones, and because the natural joint between the hammate and capitate bones is relatively stable, the device 70 effectively provides fusion of the hammate, capitate, lunate and triquetral bones.

As shown in the rear or proximal elevational (dorsal) perspective view of FIG. 15 and the top or dorsal view of FIG. 16, the fusion implant 10 can be implanted in an orientation such that the front or first side of the body 16 (the side that includes the grooves 36A-C and the axes Z1-Z1, Z2-Z2 of the internally threaded apertures 18A-C) generally faces proximally, the rear or second side of the body 16 (the side that opposes the front or first side) generally faces distally, the top or third side of the body 16 (the side that includes the grooves 38A, 38B and axes Y1-Y1 of the non-threaded apertures 20A, 20B) generally faces dorsally, and the bottom or fourth side of the body 16 (the side that opposes the top or third side) generally faces in the palmar direction. As such, the longitudinal axis X-X of the body 16 generally extends in a medial-lateral direction from the second end 14 to the first end 12, the axes Z1-Z1, Z2-Z2 of the internally threaded apertures 18A-C and the axes X2-X2 of the fusion members 50A, 50B generally extend in a proximal-distal direction from the head 54 to the tip 52, and the axes Y1-Y1 of the non-threaded apertures 20A, 20B generally extend in a dorsal-palmar direction from the third or top side including the grooves 38A, 38B about the non-threaded apertures 20A, 20B to the fourth or bottom side.

As also shown in FIGS. 15 and 16, the fusion device 70 may preferably be positioned generally intermediate in the target fusion bones in the dorsal-palmar direction. When used with the wrist, as illustrated in FIGS. 15 and 16, the device 70 may be angled in the distal-palmar direction from the first end 12 to the second end 14 and from the heads 54 of the fusion members 50A, 50B to the rear or distal surface of the body 16. The fusion implant 10 may be positioned in the medial-lateral direction such that the first internally threaded aperture 18A and the first fusion member 50A coupled thereto are positioned in the second bone B1, and at least one of the second and third internally threaded apertures 18B, 18C and at least the second fusion member 50B coupled thereto are positioned in the adjacent first bone, as shown in FIGS. 15 and 16. In such a construct, the positioning and orientation (e.g., the relative angles .theta.3, .theta.4 of the axes Z1-Z1, Z2-Z2) of the internally threaded apertures 18A-C preferably result in the fusion members 50A, 50B being positioned and oriented in intermediate positions in the medial-lateral direction of the third B3 and fourth B4 bones.

The fusion implant 10 may also be positioned intermediate in the first bone B1 and the second bone B2 in the proximal-distal direction, as shown best in FIG. 16. The proximal-distal positioning of the implant 10 and/or the lengths L13, L17 and L16 of the first threaded portion 56, second threaded portion 60 and non-threaded portion 58, respectively, of the fusion members 50A, 50B may be configured such that when the first threaded portion 56 of the fusion members 50A, 50B is threadably engaged with the internally threaded apertures 18A-C of the fusion implant 10, the first threaded portion 56 is at least primarily positioned in the first bone B1 or second bone B2 and the second threaded portion 60 is at least primarily positioned in the third bone B3 or fourth bone B4. In some embodiments, the proximal-distal positioning of the implant 10 and/or the relative lengths L13, L17 and L16 of the first and second threaded and non-threaded portions 56, 60, 58, of the fusion members 50A, 50B may be configured such that when the first threaded portion 56 of the fusion members 50A, 50B is threadably engaged with the internally threaded apertures 18A-C of the fusion implant 10, the first threaded portion 56 is only positioned in the first bone B1 or second bone B2, the second threaded portion 60 is only positioned in the third bone B3 or fourth bone B4, and the non-threaded portion spans the joint between the first and third bones B1, B3 or the second and fourth bones B2, B4.

Figure 17:
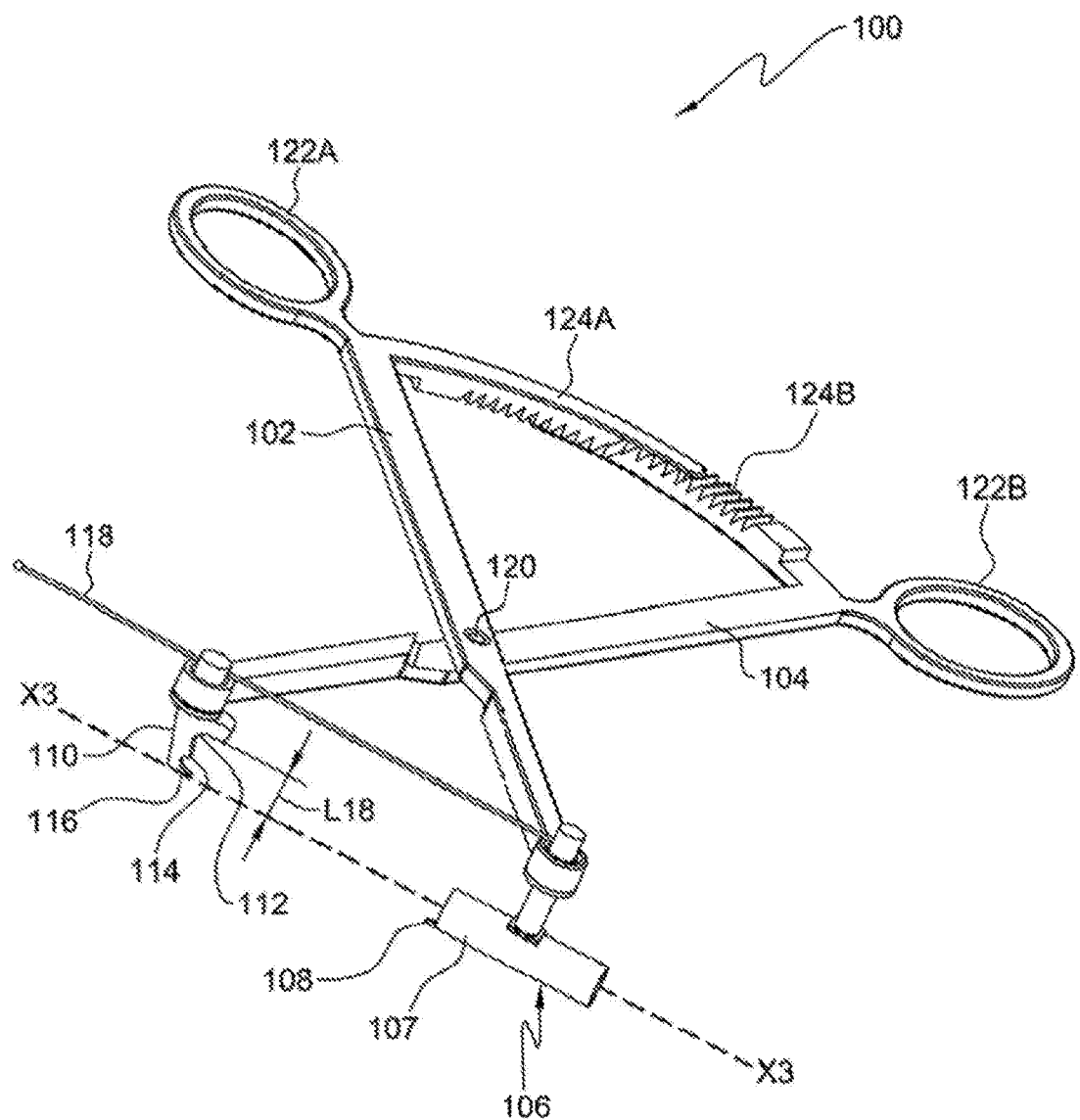
FIG. 17 is a front elevational perspective view of an exemplary embodiment of a guide clamp of the present invention.
Figure 18:
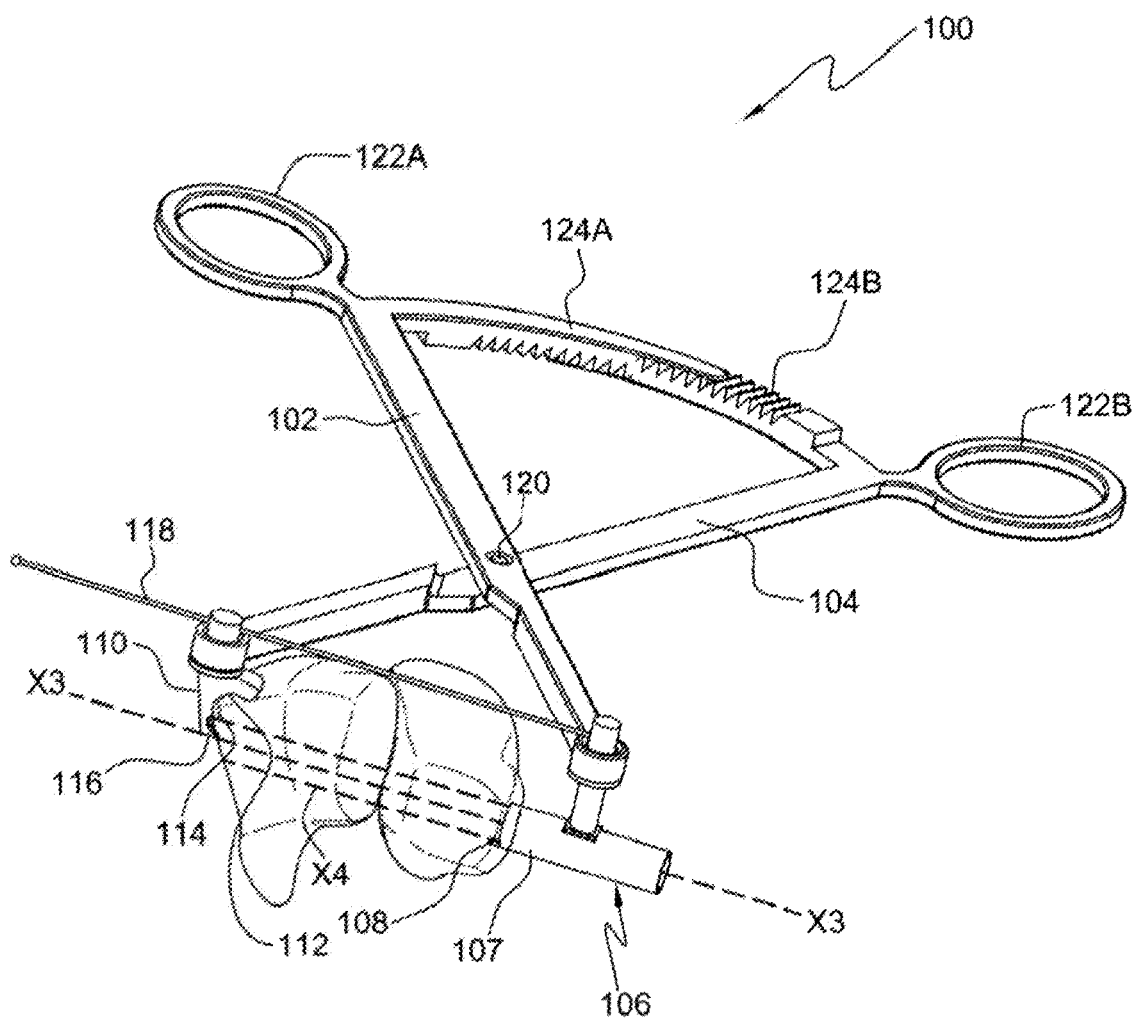
FIG. 18 is a front elevational perspective view of the guide clamp of FIG. 17 applied to exemplary bones of an upper extremity.

FIGS. 17 and 18 illustrate an exemplary instrument for use in positioning a fusion implant, such as fusion implant 10, into at least one bone to obtain a bone fusion in an upper extremity of a patient. The instrument is an exemplary guide clamp 100 that includes an exemplary first arm 102 and an exemplary second arm 104. The first and second arms 102, 104 are pivotably or rotatably coupled to each other at intermediate points thereof. In the illustrated embodiment, the coupling mechanism 120 between the first arm 102 and the second arm 104 is an exemplary hinge or pin 120. The first arm 102 may also include an exemplary first manually engageable member 122A spaced from the pivot point 120, and the second arm 104 may include an exemplary second manually engageable member 122B spaced from the pivot point 120. In the illustrated embodiment, the manually engageable members 122A, 122B are apertures sized and shape to allow a user to pass a portion on a finger therethrough.

The first arm 102 may also include a first ratcheting member 124A and the second arm 104 may include a second ratcheting member 124, and the first and second ratcheting members 124A, 124B may be engaged with each other. Engagement of the first and second ratcheting members 124A, 124B may prevent movement of the first and second arms 102, 104 in one degree of freedom allowed by the coupling mechanism 120. For example, the first and second arms 102, 104 and coupling mechanism 120 may be configured to allow two degrees of freedom between the first and second arms 102, 104 such that the manually engageable members 122A, 122B are able to move in a first direction towards each other and a second direction away from each other. In such an embodiment, the first and second ratcheting members 124A, 124B may be configured to prevent movement in the second direction. In the illustrated embodiment, the first and second ratcheting members 124A, 124B include teeth configured to mate and prevent movement in the second direction (a direction in which the manually engageable members 122A, 122B move away from one another). In such a configuration, the guide clamp 100 can be used as a scissor-like clamp.

The exemplary first arm 102 may further include an exemplary guide member 106 rotatably coupled thereto. The exemplary guide member 106 may be spaced from the first manually engageable member 122A and on an opposing side of the coupling mechanism 120 as compared to the first manually engageable member 122A. The guide member 106 may include a longitudinally extending member or barrel 107 including a first bone abutment surface 108 and an aperture extending linearly and longitudinally therethrough defining a longitudinal axis X3-X3, as shown in FIG. 17. The longitudinal axis X3-X3 of the aperture can therefore be considered the longitudinal axis of the guide member 108 and/or the member or barrel 107 of the guide member 108.

The longitudinally extending aperture of the barrel 107 of the guide member 106 may be sized and shaped to allow a drill bit therethrough. The longitudinally extending aperture may further be sized and shaped to guide a drill bit along the longitudinal axis X3-X3. In the illustrated embodiment, the longitudinally extending aperture of the barrel 107 of the guide member 106 is shaped and sized to receive a drill bit corresponding to the shape and size of the fusion implant 10 described above, and to align and guide the longitudinal axis of the drill bit with the longitudinal axis X3-X3 of the aperture of the guide member 106. As shown in FIG. 18, in such an arrangement the drill bit may create a fusion implant aperture or cavity X4 that is sized and shaped to accept the fusion implant 10 therein. As such, in the illustrated embodiment the longitudinally extending aperture of the barrel 107 of the guide member 106 is circular or cylindrical and defines a diameter of about 0.95 inch. As the guide member 106 is rotatably coupled to the first arm 102, the longitudinal axis X3-X3 of the aperture of the guide member 106 is also rotatable with the first arm 102.

The guide member 106 may also include a first bone abutment surface 108 on an outer surface of the barrel 107 configured to abut or otherwise engage a first outer surface of a first bone. In the illustrated embodiment, the exemplary first abutment surface 108 includes a projection or spike extending from the outer surface of the barrel 107 of the guide member 106. The exemplary spike of first bone abutment surface 108 extends in a direction generally along the direction of longitudinal axis X3-X3. In such an embodiment, the projection of the first abutment surface 108 may be sized and shape to penetrate or extend into the first outer surface of the first bone. In such an arrangement, the projection of the first abutment surface 108 may stabilize the location and orientation of the barrel 107, and thus the longitudinal axis X3-X3, of the guide member 106 at the first bone. Ultimately, the first abutment surface 108 may stabilize the location and orientation of a drill bit passing through the barrel 107 at the first bone. In such an arrangement, other outer surfaces of the barrel 107, instead of or in addition to the projection, may form the first abutment surface 108. For example, the illustrated projection or spike extending from the outer surface of the barrel 107 may penetrate and extend into a first outer surface of the first bone, and upon such penetration other surfaces of the barrel 107 may contact the first surface of the first bone, as illustrated in FIG. 18. As such, the outer surfaces of the barrel 107 may generally be considered the first abutment surface 108 (i.e., the projection or spike may be part of the first abutment surface 108). In some alternative embodiments, the first abutment surface 108 does not include the projection or spike. The guide member 106 may provide a visual and tactile indication of the location of the longitudinal axis X3-X3 of the aperture of the guide member 106 at the first outer surface of the first bone.

The exemplary second arm 104 may include an exemplary bone abutment member 110 rotatably coupled thereto, as shown in FIGS. 17 and 18. The bone abutment member 110 may preferably be configured to engage the outer surface of a second bone that is adjacent and spaced from the first bone, as shown in FIG. 18. The exemplary bone abutment member 110 may be spaced from the second manually engageable member 122B and on an opposing side of the coupling mechanism 120 as compared to the second manually engageable member 122B. The bone abutment member 110 may include an exemplary second bone abutment surface 112 and an exemplary third bone abutment surface 114 configured to abut or otherwise engage at least one second outer surface of a second bone. For example, the exemplary bone abutment member 110 may be positioned and oriented such that the second and third bone abutment surfaces 112, 114 abut or otherwise engage a second outer surface of a second bone that substantially opposes the first outer surface of the first bone and a top or dorsal outer surface of the second bone, as shown in FIG. 17.

As best shown in FIG. 17, the exemplary second bone abutment surface 112 of the exemplary bone abutment member 110 may be a member or surface extending longitudinally in a direction generally along the direction of the longitudinal axis X3-X3 of the guide member 106 of the first arm 102. In such an arrangement, the second bone abutment surface 112 may be configured to abut or engage a top or dorsal outer surface of the second bone, as shown in FIG. 18.

Similarly, the exemplary third bone abutment surface 114 of the exemplary bone abutment member 110 may be a member or surface. However, the third bone abutment surface 114 may extend in a lateral direction such that it intersects the longitudinal axis X3-X3 of the aperture of the guide member 106 of the first arm 102. In the illustrated embodiment, the third bone abutment surface 114 includes a projection or hook 116 that includes a point that intersect the longitudinal axis X3-X3 of the aperture of the guide member 106 of the first arm 102. In such an arrangement, the third bone abutment surface 114, including the projection 116, may thereby be configured to engage the second outer surface of the second bone that substantially opposes the first outer surface of the first bone, as shown in FIG. 18. The lateral location of the projection or hook 116 of the third bone abutment surface 114 on the second bone may thereby depend upon the lateral length L18 of the third bone abutment surface 114 from the second bone abutment surface 112 (because the second bone abutment surface 112 is configured to contact the top or dorsal surface of the second bone), as shown in FIG. 18. As the projection 116 of the third bone abutment surface 114 intersects the longitudinal axis X3-X3 of the aperture of the guide member 106 of the first arm 102, the lateral length L18 is determinative of the dorsal-palmar location or orientation of an implant cavity formed in the bones via the guide member 106.

In the illustrated embodiment, the guide clamp 100 is particularly well suited for facilitating the forming of an implant cavity in the hammate and capitate bones of the wrist, and the projection 116 of the third bone abutment surface 114 is configured to sit within a detent in the outer surface of the hammate bone, such as at the tubercle or depression located at the capitate-trapezoid articulation. In such an embodiment, the lateral length L18 between the second bone abutment surface 112 and the projection 116 of the third bone abutment surface 114 is preferably about 0.3 inch.

As the projection 116 of the third bone abutment surface 114 intersects the longitudinal axis X3-X3 of the aperture of the guide member 106 of the first arm 102, the projection 116 provides a visual and tactile indication of the location of the longitudinal axis X3-X3 of the aperture of the guide member 106 at the second outer surface of the second bone, as shown in FIG. 18. As such stated above, the guide member 106 provides a visual and tactile indication of the location of the longitudinal axis X3-X3 of the aperture of the guide member 106 at the first outer surface of the first bone. Therefore, the exemplary guide clamp 100 can be used to create an implant cavity X4 spanning spaced adjacent bone, such as the hammate and capitate bones, and the position and orientation of the implant cavity X4 can be tactilely and visually indicated by the guide clamp 100 before the implant cavity X4 is formed in the bones. Further, as the illustrated projection 16 of the abutment member 110 of the second arm is configured to couple to a particular predefined location of the outer surface of the second or hammate bone, the guide member 106 of the second arm 14 can be selectively positioned on the outer surface of the first or capitate bone in reference to the longitudinal axis X3-X3 of the barrel 107 so that the implant cavity X4 formed by way of the aperture of the barrel 107 (and the fusion implant 10 implanted therein) passes through the bones (such as the hammate and capitate bones) in a medial-lateral direction in intermediate portions in dorsal-palmar and distal-proximal directions, as shown in FIGS. 15, 16 and 18.

As discussed above, the guide member 106 may be rotatably coupled to the first arm 102, and the abutment member 110 may rotatably coupled to the second arm 104. In such an arrangement, the guide clamp 100 may be configured such that the longitudinal axis X3-X3 of the guide member 106 is aligned with the projection 116 of the abutment member 110, such as to provide the tactile and visual indication of the positioning and orientation of the implant cavity X4 formed or facilitated by the guide member 106. In embodiments particularly configured for use with the hammate and capitate bones of the wrist, the alignment of the longitudinal axis X3-X3 of the guide member 106 with the projection 116 of the abutment member 110 is particularly critical because the projection 116 is configured to couple to a predefined point of the hammate bone determined to provide an advantageous position and orientation of the implant cavity X4. Stated differently, the projection 116 can be used as a standard pre-determined reference point from which the position of the guide clamp 100 can be based. Thus, maintaining alignment of the axis X3-X3 of the guide member 106 with the abutment member 110, and therefore the axis of the implant cavity X4, is advantageous.

In the illustrated embodiment, the guide clamp 100 includes a positioning member 118 that maintains the orientation of the guide member 106 and abutment member 110 during movement of the first and second arms 102, 104 such that the longitudinal axis X3-X3 of the guide member 106 aligns with the projection 116 of the abutment member 110 during movement of the first and second arms 102, 104 relative to each other. Stated differently, the positioning member 118 maintains an aligned orientation between the guide member 106 and abutment member 110. The "aligned orientation" therefore refers to the alignment of the longitudinal axis X3-X3 of the guide member 106 with the projection 116 of the abutment member 110.

As shown in FIGS. 17 and 18, the positioning member 118 is an elongate member coupled to a post of each of the guide member 106 and the abutment member 110. The positioning member 118 is slidably coupled to at least one of the posts of the guide member 106 and the abutment member 110 and fixedly coupled to the other post of the guide member 106 and the abutment member 110. In the illustrated embodiment, the positioning member 118 is slidably coupled the abutment member 110 and fixedly coupled to the guide member 106. In such an arrangement, when the first and second arms 102, 104 are rotated about the coupling mechanism 120, the guide member 106 and the abutment member 110 move toward or away from each other, depending upon the direction of the movement, along an arc about the coupling mechanism 120. As the guide member 106 and the abutment member 110 move along their arcuate paths, the positioning member 118 slides within the post of the abutment member 110 and forces the posts of the guide member 106 and the abutment member 110 to rotate with the first and second arms 102, 104, respectively, to maintain the aligned orientation of the guide member 106 and the abutment member 110.

FIG. 18 shows the exemplary guide clamp 100 of FIGS. 17 and 18 in use with the hammate and capitate bones of the wrist. As shown in FIG. 18, the manually engageable members 122A, 122B can be engaged and the first and second arms 102, 104 pivoted with respect to one another to clamp the hammate and capitate bones between the guide member 106 and the abutment member 110. The positioning member 118 can maintain the aligned orientation of the guide member 106 and the abutment member 110 during such pivoting (i.e., the longitudinal axis X3-X3 of the guide member 106 is maintained in alignment with the projection 116 of the abutment member 110). In such a position, the teeth of the first and second ratcheting members 124A, 124B can prevent the first and second arms 102, 104 from pivoting away from each other, and therefore maintain the clamped position of the first and second arms 102, 104. As also shown in FIG. 18, the first bone abutment surface 108 may be clamped such that it abuts or engages the outer surface of the capitate, such as the projection being pushed into the capitate and the remaining portion of the abutment surface 108 being abutted against the outer surface of the capitate. Similarly, the projection 116 of the third bone abutment surface 114 of the bone abutment member 110 can be clamped such that it couples in the detent of the outer surface of the hammate bone, the remaining portion of the third bone abutment surface 114 abuts with the outer surface of the hammate, and the second bone abutment surface 112 abuts with the top or dorsal outer surface of the hammate. In such an orientation, the implant cavity X4 can be formed via the guide member 106 in intermediate portions of the hammate and capitate.

Figure 19:
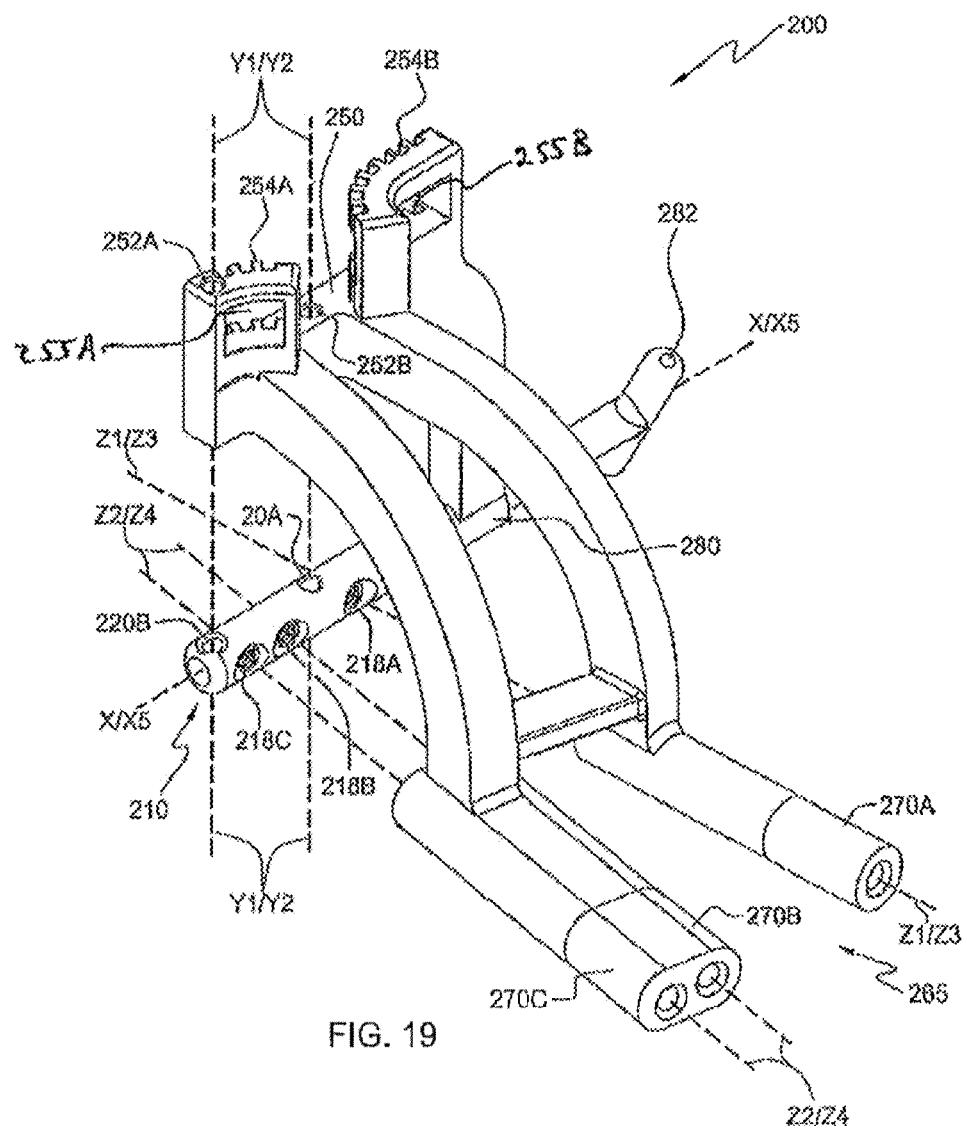
FIG. 19 is a rear elevational perspective view an exemplary embodiment of a surgical instrument of the present invention.
Figure 20:
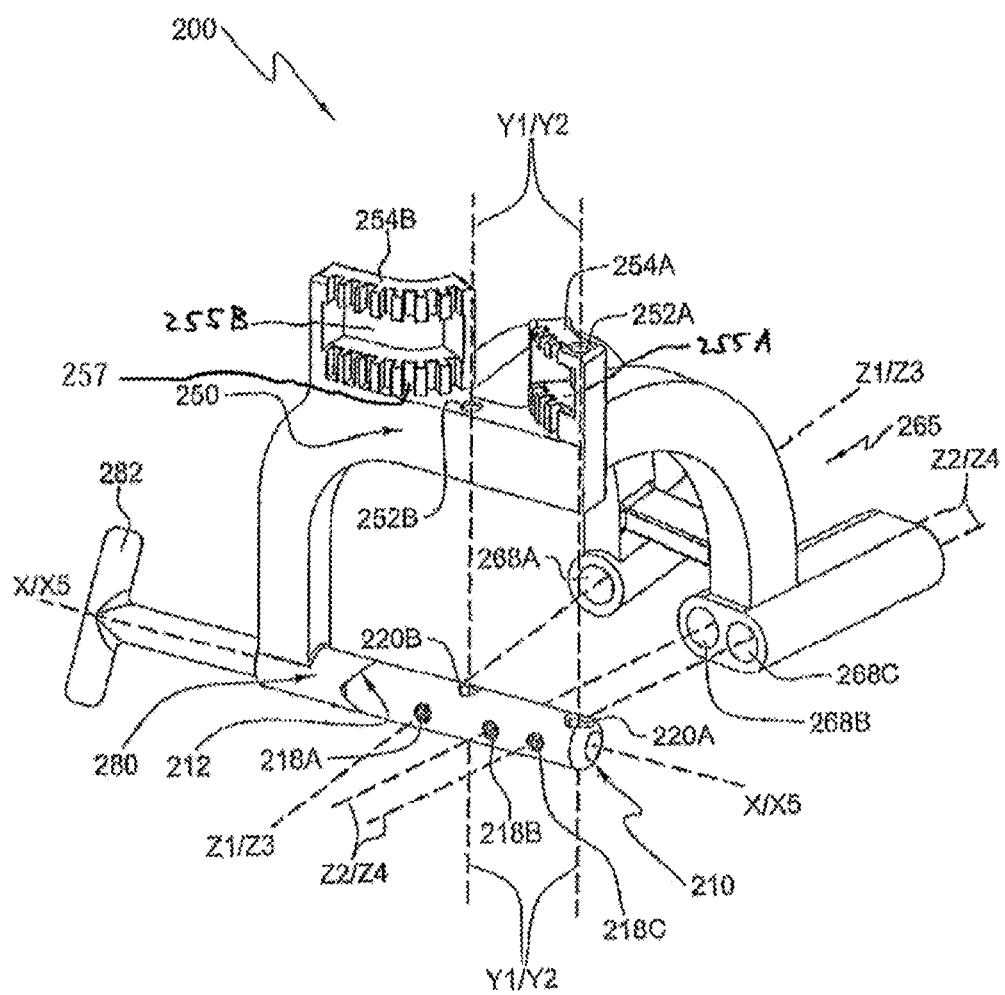
FIG. 20 is a front elevational perspective view of the surgical instrument of FIG. 19.
Figure 21:
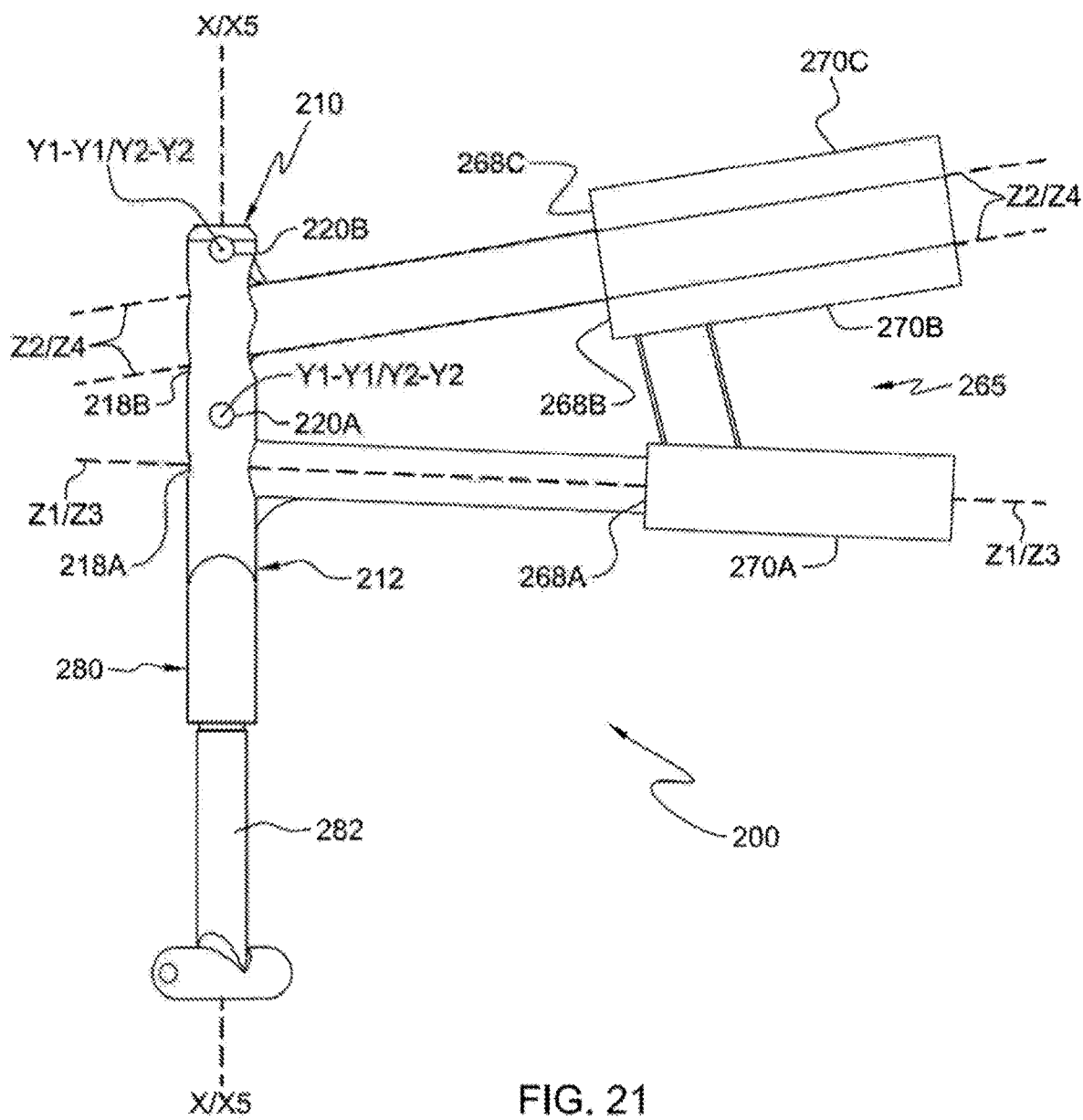
FIG. 21 is a bottom view the surgical instrument of FIG. 19.

FIGS. 19-21 illustrate an exemplary instrument for use in positioning a fusion implant and fusion members into adjacent bones to obtain bone fusion in an upper extremity of a patient. The exemplary instrument is an exemplary targeting guide 200 that includes an exemplary fusion implant 210, an exemplary targeting member 250, at least one exemplary guide member 265, and an exemplary outrigger member 280. The exemplary fusion implant 210 is substantially the same as the exemplary fusion implant 10 described above with reference to FIGS. 1-8 and 12-16, and therefore like reference numerals preceded by the numeral "2" are used to indicate like elements. The description presented above with respect to fusion implant 10 of FIGS. 1-8 and 12-16 therefore equally applies to fusion implant 210, but is not repeated here for brevity purposes.

As best shown in FIGS. 19 and 20, the exemplary targeting member 250 includes at least one arm that couples to the exemplary at least one guide member 265 and the exemplary outrigger member 280. In one embodiment, the targeting member 250, the guide members 265 and the member 280 are monolithic. The exemplary targeting member 250 may include at least one bone anchor aperture 252 extending through the targeting member 250 such that a bone anchor can pass through the targeting member 250 and into a bone. The at least one bone anchor aperture 252 thereby allows the targeting member 250, and therefore the targeting guide 200, to be coupled or fixed to a bone via a bone anchor. A bone anchor may take any form capable of acting as a bone anchor. For example, the bone anchor may be a k-wire, screw, nail, or wire. In the illustrated embodiment, the exemplary targeting member 250 includes two bone anchor apertures 252A, 252B extending therethrough defining axes Y2-Y2. The bone anchor apertures 252A, 252B are configured to accept a k-wire therethrough. As a result, the bone anchor apertures 252A, 252B are circular or cylindrical and define a diameter substantially similar to known standard k-wire sizes. For example, the first and second bone anchor apertures 252A, 252B may define a diameter of about 0.63 inches.

In the illustrated embodiment, a first bone anchor aperture 252A is positioned proximate one end of the targeting member 250, and a second bone anchor aperture 252A is spaced from the first bone anchor and positioned on an intermediate portion of the targeting member 250. The first and second bone anchor apertures 252A, 252B are preferably positioned and oriented such that they align with the first and second non-threaded apertures 220A, 220B of the fusion implant 210 when the fusion implant 210 is coupled to the outrigger member 280 in a first or "proper" orientation, as described further below. This may be accomplished through the configuration of the targeting member 250, the outrigger member 280 and the relative positioning of the first and second bone anchor apertures 252A, 252B themselves in the targeting member 250, as well as the positioning and orientation of the first and second non-threaded apertures 220A, 220B in the fusion implant 210. As shown in FIG. 19, the axes Y2-Y2 of the illustrated first and second bone anchor apertures 252A, 252B are substantially aligned with the axes Y1-Y1 of the first and second non-threaded apertures 20A, 20B, respectively of the fusion implant 210.

Therefore, in such an arrangement, when the fusion implant 210 is implanted in multiple bones such that the first non-threaded aperture 220A is positioned in a first bone and the second non-threaded aperture 220B is positioned in a second bone adjacent the first bone, a first bone anchor can be inserted through the first bone anchor aperture 252A of the targeting member 250, into the first bone, and into the first non-threaded aperture 220A of the fusion implant 220. Similarly, in such a construct, a second bone anchor can be inserted through the second bone anchor aperture 252B of the targeting member 250, into the second bone, and into the second non-threaded aperture 220B of the fusion implant 220 (see FIGS. 23 and 29). In this way, the first and second bone anchor apertures 252A, 252B can couple or fix the targeting instrument 200, fusion implant 210 and first and second bones with respect to one another via the first and second bone anchors 252A, 252B. The positioning, orientation, shape and size of the first and second bone anchors 252A, 252B is thereby dependent upon the positioning, orientation, shape and size of the first and second non-threaded apertures 220A, 220B of the fusion implant 210, or vice versa. As such, when the targeting instrument 200 includes the fusion implant 210 of FIGS. 1-8 and 12-16 coupled in the first or "proper" orientation, the above described positioning, orientation, shape and size of the first and second non-threaded apertures 220A, 220B and their axes Y1-Y1 equally applies to the first and second bone anchors 252A, 252B and their axes Y2-Y2.

The targeting member 250 may include at least one clamp member 254 configured to receive a clamp thereon to secure or couple another bone anchor to the targeting member 250, and therefore to the targeting instrument 200. In the illustrated embodiment, the targeting member 250 of the targeting instrument 200 includes two clamp members, a first clamp member 254A positioned adjacent the first bone anchor aperture 252A at a first axial side portion of the targeting member 250, and a second clamp member 254B spaced from the first clamp member 254A and the second intermediate bone anchor aperture 252B at a second axial side portion of the targeting member 250 (with respect to the axis X-X of the fusion implant 210). The first clamp member 254A is positioned such that the first bone anchor aperture 252A passes through a portion of the first clamp member 254A but does not interfere with the functioning of the first clamp member 254A. In some alternative embodiments, the first and second clamp members 254A, 254B are formed into, or are a part of, the targeting member 250 (rather than projecting from the targeting member 250 as illustrated). In some such embodiment, the first and second clamp members 254A, 254B are formed into, or are a part of, a lower (plantar) portion of the targeting member 250. In some alternative embodiments, the first and second clamp members 254A, 254B project form a lower (plantar) surface of the targeting member 250.

Each of the first and second clamp members 254A, 254B may include a ribbed or slotted surface. In the illustrated embodiment, each of the first and second clamp members 254A, 254B include a slotted surface on a distal side of the first and second clamp members 254A, 254B, and the slots extending generally in a dorsal-palmar direction. In some embodiments, the slots of the slotted surface are "V" shaped grooves in the surface. In alternative embodiments, the slots of first and second clamp members 254A, 254B extend in a direction other than generally in a dorsal-palmar direction, and are configured on any side of the clamp members 254A, 254B. Each of the first and second clamp members 254A, 254B may also include an aperture 255A, 255B extending through the slotted surface, as shown best in the illustrated embodiment in FIGS. 19 and 20. In arrangements including first and second clamp members 254A, 254B with such apertures and slotted surfaces, the first and second clamp members 254A, 254B may be configured to accept a clamp through the aperture and into the slotted surface, as described below. As also described further below, the slots of the slotted surface may prevent rotation of a clamp associated with the first and second clamp members 254A, 254B, and therefore angulation or rotation of the bone anchors and bones secured thereby.

As shown in FIGS. 19 and 20, the first and second clamp members 254A, 254B are curved or radiused such that the slotted surface is of a convex shape. Such an arrangement allows a clamp to couple to the first and second clamp members 254A, 254B via the curved slotted surface in numerous different positions and orientations depending upon the position or orientation of a particular bone anchor. As such, the clamp can be positioned and oriented in a manner that facilitates a secure coupling with a particular bone anchor, and therefore a secure coupling of the bone anchor to the targeting member 250 and targeting instrument 200, as described further below.

An outrigger member 280 may be coupled to the targeting member 250 by an arm extending from the outrigger member 280 to the targeting member 250. In such arrangements, the arm coupling the outrigger member 280 and the targeting member 250 may be considered part of the targeting member 250, part of the outrigger member 280, or the targeting member 250 and the outrigger member 280 may both include a portion of the arm. As shown best in FIGS. 20 and 21, the outrigger member 280 may couple to the first end 212 of the fusion implant 210.

As shown in FIGS. 20 and 21, the outrigger member 280 may include an end portion that is shaped and sized to receive, couple or mate with the first end 212 of the fusion implant 210. Specifically, in the illustrated embodiment, the outrigger member 280 includes the shape (cylindrical) of the fusion implant 210 and an end profile that mimics or mirrors the profile of the first end 212 of the fusion implant 210, but in reverse. In such embodiments, the above described configuration of the first end 12 of the fusion implant 10 equally applies to the configuration of the profile of the outrigger member 280, but in a reversed or mirrored configuration so that the outrigger member 280 can mate with the first end 212. As described above, the skewed or off-center profile or configuration of the first end 212 of the fusion implant 210 allows the fusion implant 210 to be coupled to such an outrigger member 280 in only two orientations—an "improper" orientation and a "proper" orientation. Further, the skewed or off-center profile or configuration of the first end 212 provides a visual or tactile indication when it is configured in an "improper" orientation with the outrigger member 280, as compared with the "proper" orientation. In the illustrated embodiment, as the profile or configuration of the first end 212 of the fusion implant 210 and the end of the outrigger member 280 take skewed or off-center "V" shapes (e.g., when viewed from the distal direction), with one leg of the "V" being longer than the other leg, the outer surfaces of the fusion implant 210 and the outrigger member 280 will be skewed or otherwise not aligned when they are coupled or mated in the "improper" orientation. As shown best in FIG. 20, the first end 212 of the fusion implant 210 and the end of the outrigger member 280 are coupled in the "proper" orientation and the outer surfaces of the fusion implant 210 and the outrigger member 280 are aligned and even.

Further, as described above the first end 212 of the fusion implant 210 includes a threaded aperture 240 (not shown) extending longitudinally about the axis X-X of the fusion implant 210 (see FIGS. 7 and 8). Similarly, the outrigger member 280 includes an aperture (not shown) that extends longitudinally through the outrigger member 280 defining an axis X5-X5. The axis X5-X5 of the aperture of the outrigger member 280 is configured to align with the axis X-X of the aperture of the first end 212 of the fusion implant 210 when the fusion implant 210 is coupled to the outrigger member 280 in the "proper" orientation. In such an orientation, as shown in FIGS. 19-21, a threaded tightening bolt 282 can be received within the longitudinally extending aperture of the outrigger member 280 and into threaded engagement with the internal threading 242 (not shown) of the longitudinally extending aperture 240 (not shown). By including a stop surface configured to contact the outer surface of the outrigger member 280 opposing the first end 212 of the fusion implant 210, the tightening bolt 282 can be rotated and the first end 12 of the fusion implant 210 pulled into engagement with the outrigger member 280. Further rotation of the tightening bolt 282 will securely selectively couple the fusion implant 210 to the outrigger member 280 in the "proper" orientation.

As described further below, by securing the fusion implant 210 in such a predefined orientation, the aspects of the targeting instrument 200 can be designed or configured to align, cooperate or engage with particular aspects of the fusion implant 210. For example, as explained above, the first and second bone anchor apertures of the 252A, 252B of the targeting member 250 preferably align with the first and second non-threaded apertures 220A, 220B of the fusion implant 210, respectively. As shown in the illustrated embodiment, the coupling of the fusion implant 210 to the outrigger member 280 in the "proper" orientation ensures that the first and second bone anchor apertures 252A, 252B align with the first and second non-threaded apertures 220A, 220B, respectively.

The off-center or skewed profile of the first end 212 of the fusion implant 210, as well as the profile of the end of the outrigger member 280, will also prevent the alignment of the longitudinally extending apertures of the outrigger member 280 and fusion implant 210 when the outrigger member 280 and the fusion implant are coupled in the "improper" orientation (they will be askew). As such, the configuration or profile of the outrigger member 280 and first end 212 of the fusion implant 210 prevents the instrument 200 and the fusion implant 210 to be selectively or removably coupled to one another in any orientation other than the "proper" orientation via the threaded tightening bolt 282.

As illustrated in FIGS. 19-21, the at least one guide member 265 may be coupled to the targeting member 250 by an arm extending from the at least one guide member 265 to the targeting member 250. In such arrangements, the arm coupling the at least one guide member 265 and the targeting member 250 may be considered part of the targeting member 250, part of the at least one guide member 265, or the targeting member 250 and the at least one guide member 265 may both include a portion of the arm. As shown best in FIG. 19, constructs including multiple guide members 265 may include multiple arms coupling the guide members 265 to the targeting member 250.

In the illustrated embodiments, the targeting instrument 200 includes two guide members 265 laterally spaced (spaced in a proximal-distal direction) from the outrigger member 280 and the fusion implant 210 coupled thereto, with respect to the longitudinal axis X-X of the fusion implant 210. The guide members 265 are also longitudinally spaced form one another with respect to the longitudinal axis X-X of the fusion implant 210. The two guide members 265 define at least one guide tube or barrel that includes elongate laterally extending guide apertures defining axes that extend laterally (in a proximal-distal direction), with respect to the longitudinal axis X-X of the fusion implant 210.

As shown in FIGS. 19-21, the guide members 265 define a first laterally extending guide aperture 268A defining an axis Z3-Z3, and second and third laterally extending guide apertures 268B, 268C defining axes Z4-Z4. The target instrument 200 is preferably configured such that, when the fusion implant is coupled in the first or "proper" orientation with the outrigger member 280, the axis Z3-Z3 of the first guide aperture 268A is aligned with the axis Z1-Z1 of the first internally threaded aperture 218A of the fusion implant 210, the axis Z4-Z4 of the second guide aperture 268B is aligned with the axis Z2-Z2 of the second internally threaded aperture 218B of the fusion implant 210, and the axis Z4-Z4 of the third guide aperture 268C is aligned with the axis Z2-Z2 of the third internally threaded aperture 218C of the fusion implant 210. In such an embodiment, at least the positioning and orientation of the first, second and third guide apertures 268A-C are thereby dependent upon the positioning and orientation of the first, second and third threaded apertures 218A-C, respectively, of the fusion implant 210, or vice versa. As such, when the targeting instrument 200 includes the fusion implant 10 of FIGS. 1-8 and 12-16 coupled in the "proper" orientation, at least the above described positioning and orientation of the threaded apertures 18A-C and their respective axes Z1-Z1 and Z2-Z2 equally applies to the guide apertures 268A-C and their respective axes Z3-Z3 and Z4-Z4, but is not repeated herein for brevity purposes.

Figure 22:
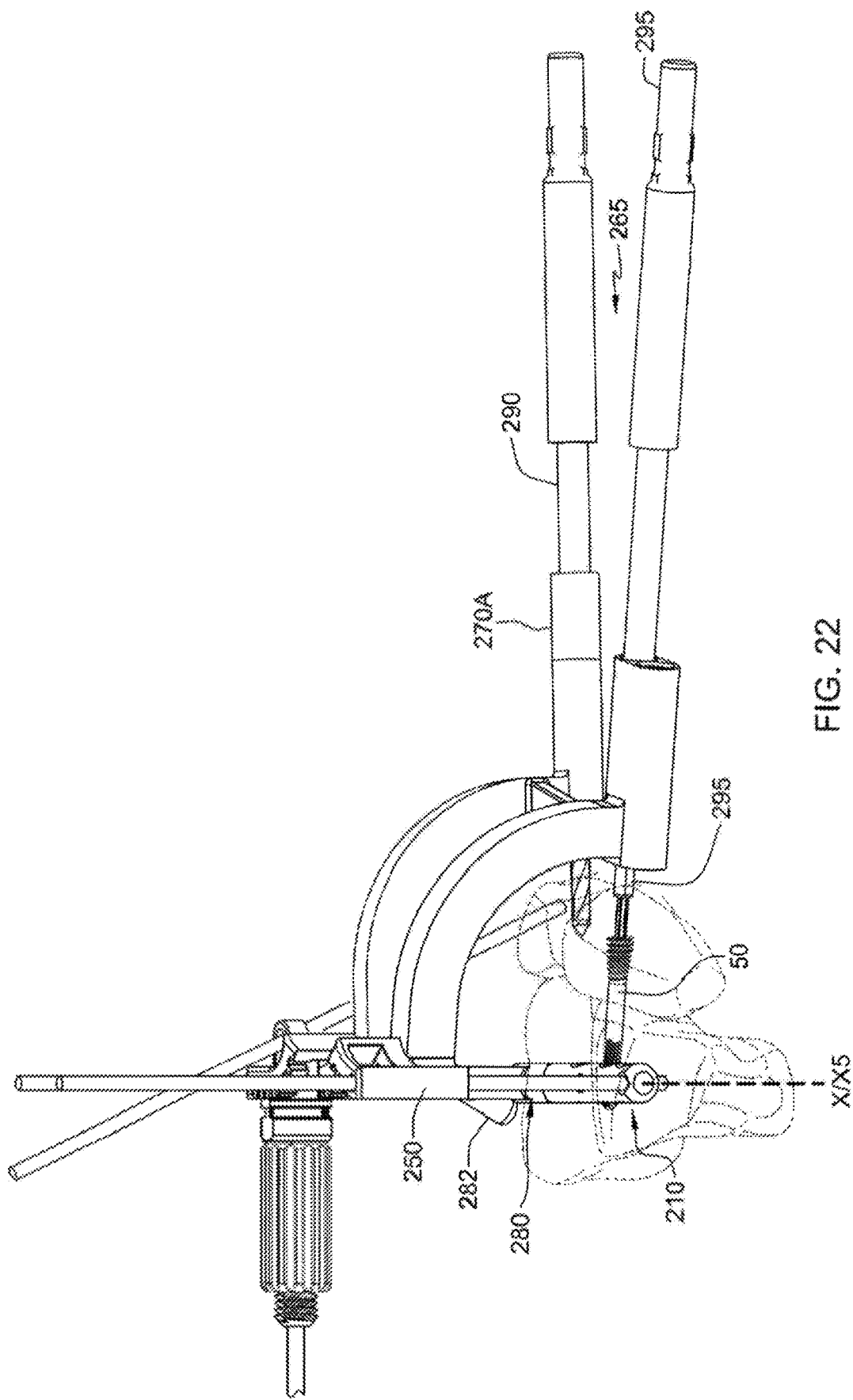
FIG. 22 is a longitudinal view of the surgical instrument of FIG. 19.
Figure 23:
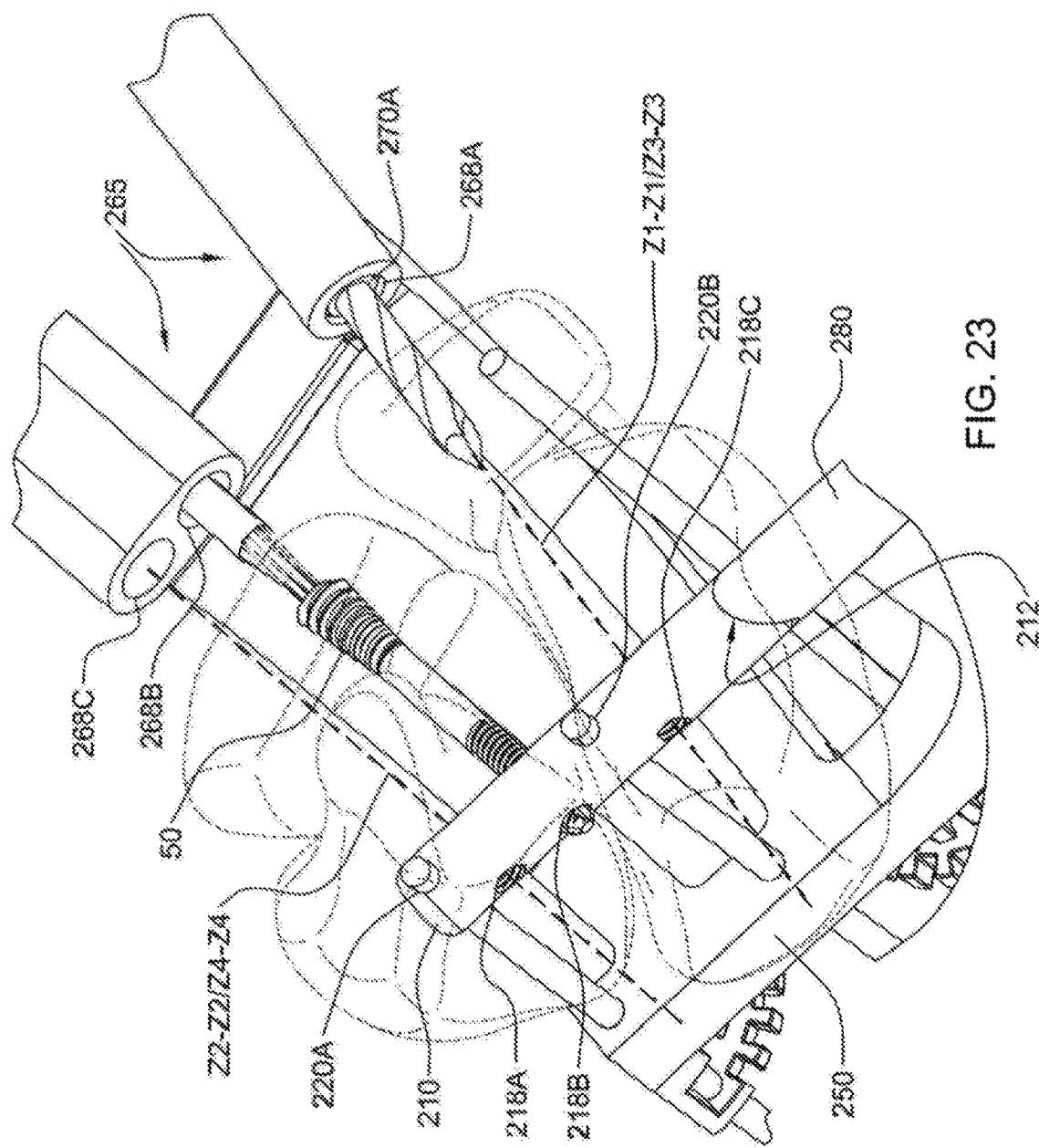
FIG. 23 is a bottom perspective view of the surgical instrument of FIG. 19.

In such an arrangement, as illustrated in FIGS. 19-21, the guide apertures 268A-C of the at least one guide member 265 can facilitate the drilling of cavities through bone or bones to the internally threaded apertures 218A-C of the fusion implant 210, as shown in FIGS. 22 and 23. For example, as show in FIGS. 19 and 20, the at least one guide member 265 is laterally spaced from the fusion implant along the axes Z1-Z1, Z2-Z2 of the internally threaded apertures 218A-C, and therefore the axes Z3-Z3 and Z4-Z4 of the guide apertures 268A-C of the at least one guide member 265. In such a spaced relationship, when the fusion implant 210 is coupled to the outrigger member 280 in the "proper" orientation and inserted into a fusion implant cavity in adjacent first and second bones, for example, the targeting instrument 200, and therefore the fusion implant 210, can be rotated about the longitudinal axis X-X of the fusion implant 210 and into an orientation such that third and fourth bones adjacent the first and second bones are positioned between the fusion implant 201 and the at least one guide member 265, as shown in FIGS. 22 and 23. The targeting instrument 200 and fusion implant 210 may then be secured to the first, second, third or forth bones utilizing the first and second clamp member 252A, 252B and the first and second bone anchor apertures 252A, 252B, as described further below and shown in FIGS. 22 and 23.

In such a configuration or orientation, first, second and third drill bushings 270A-C may be coupled to the first, second and third guide apertures 268A-C, respectively, as shown in FIGS. 19 and 21. As the second and third internally threaded apertures 218B, 218C may be substantially parallel and in close proximity, the second and third drill bushings 270A, 270B may be combined into a single bushing that includes two sub-bushing members corresponding to the second and third drill bushings 270A, 270B, as shown in the illustrated embodiment. The drill bushings 270A-C preferably define laterally extending apertures of a diameter less than the diameter of the at least one guide member 265, and apertures defining axes that are aligned with the axes Z3-Z3 and Z4-Z4 of the guide apertures 268A-C. In such an arrangement, the axes of the drill bushings 270A-C align with the axes Z1-Z1, Z2-Z2 of the internally threaded apertures 218A-C of the fusion implant 210. As such, a drill bit can be inserted into the drill bushings 270A-C, and the drill bushings 270A-C used to guide the drill bit through the first, second, third and fourth bones to the internally threaded apertures 218A-C of the fusion implant 210, as shown in FIGS. 22 and 23.

As the distance along the axes Z3-Z3 and Z4-Z4 of the guide apertures 268A-C between the internally threaded apertures 218A-C of the fusion implant 210 and the outer edges of the at least one guide member 265, for example, are constant distances, a depth gauge (not shown) can be inserted into the at least one guide member 265 before the drill bushings 270A-C are coupled thereto and used to determine the distance between such a fixed point the internally threaded apertures 218A-C of the fusion implant 210. Based on the depth reading taken from the depth gauge, particular drill bushings 270A-C providing a stop surface corresponding to the depth of the internally threaded apertures 218A-C of the fusion implant 210 being used may be inserted into the at least one guide member 265 before the drilling process. Then, during the drilling process, the drill bit 290 may be guided by the particular drill bushings 270A-C and particular drill bushings 270A-C to the stop, such that the tip of the drill bit 290 is extended to the internally threaded apertures 218A-C of the fusion implant 210, as shown in FIGS. 22 and 23. It is noted that tolerances involved in the machining and manufacturing process may result in the drill bit 290 coming very close to the internally threaded apertures 218A-C, such as about 2 millimeters away, or the drill bit 290 may enter the internally threaded apertures 218A-C slightly.

Once the drilling process is complete, the drill bushings 270A-C may be removed from the at least one guide member 265, as shown in FIGS. 22 and 23. As also shown in FIGS. 22 and 23, a fusion member, such as the exemplary bone screw 50 described above, may then be inserted into each of the guide members 265 and guided thereby into the formed fusion member cavities corresponding to the internally threaded apertures 218A-C of the fusion implant 210. A driver 295 may then be used to rotatably advance the fusion members into the corresponding bones and, eventually, into threaded engagement with the internally threaded apertures 218A-C of the fusion implant 210, as shown in FIGS. 22 and 23.

Figure 24:
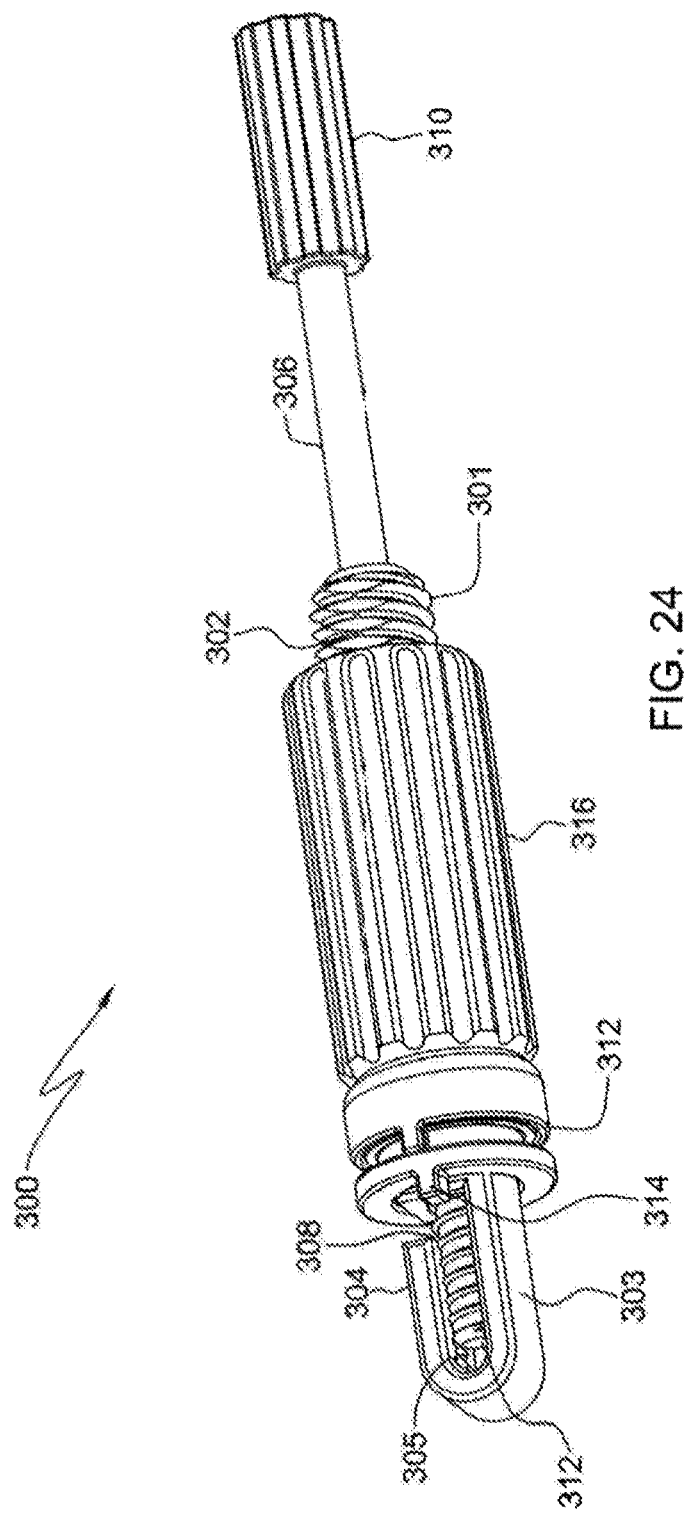
FIG. 24 is a side perspective view of an exemplary embodiment of a clamp according to the present invention.
Figure 25:
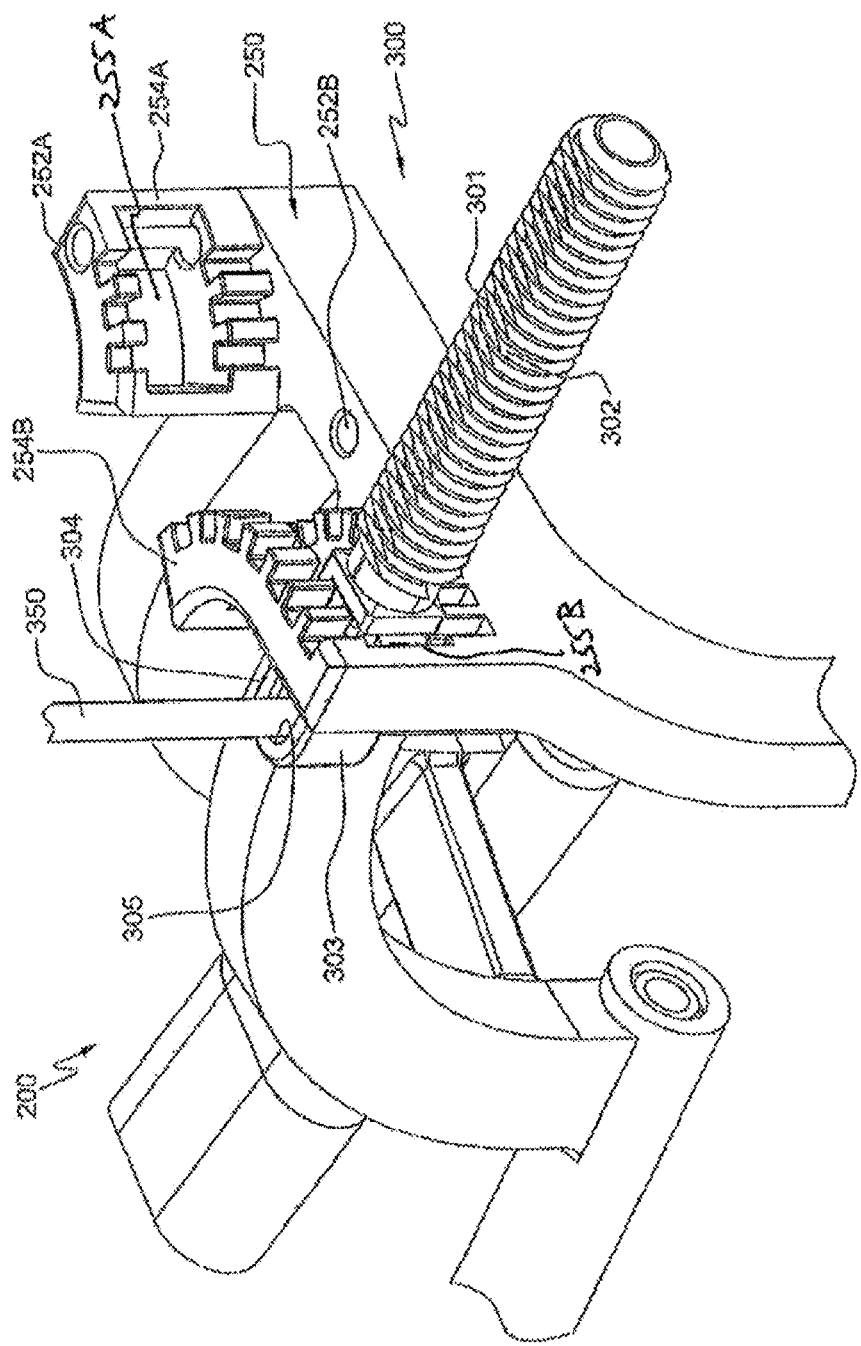
FIG. 25 is a front elevational perspective view of a first portion of the clamp of FIG. 24 applied to the surgical instrument of FIG. 19.

As described above, the targeting instrument 200 and fusion implant 210 may be secured to the first, second, third and/or fourth bones utilizing at least one clamp before the drilling process is completed. An exemplary embodiment of a clamp for use with the first and second clamp members 254A, 254B of the targeting member 250 is illustrated in FIGS. 24-28. As shown best in FIGS. 24 and 25, the exemplary illustrated clamp 300 includes a hook member 301. The hook member 301 is configured to pass at least partially through the apertures 255A, 255B of the first and second clamp members 254A, 254B of the targeting member 250. The hook member 301 is an elongate "J" shaped member including an elongate shaft-like member 302 and a head portion 303 at one end of the shaft 302. The shaft 302 may include exterior threading and an interior aperture extending through the shaft 302 to the head portion 303. In the illustrated embodiment, the interior aperture includes internal threads. The head member 303 may be a "U" shaped member defining an interior arcuate channel 305 and an access member 304 that extends from the arcuate channel 305 towards the shaft 302. The access member 304 may not extend fully back to the shaft 302, thereby creating a pathway into the interior of the head member 303 and the arcuate channel 305. The internally threaded aperture of the shaft 302 extends to the interior of the head member 303 such that the axis defined by the internally threaded aperture intersects the arcuate channel 305. In use, the head member 303 may pass through the apertures 255A, 255B of the first and second clamp members 254A, 254B. For example, as shown in FIG. 25, the head member 303 may pass through the aperture 255B of the second clamp member 254B such that the interior arcuate channel 305, access member 304, and pathway defined by the access member 304 are located on the side of the second clamp member 254B that is void of slots or grooves, and the shaft 302 extends on the opposing side of the of the second clamp member 254B that includes the slots or grooves.

As shown in FIG. 25, in such an arrangement a bone anchor 350 may be implanted into a bone and then moved through the pathway formed by the head portion 303 and access member 304 and into the interior of the head portion 303 and within the arcuate channel 305. In some embodiments, the bone anchor 350 is manipulated into the interior of the head portion 303, and in other embodiments the hook member 301 is manipulated such that the bone anchor 350 is passed into the interior of the head portion 303. The pathway formed by the access member 304 and the other portions of the head portion 303 therefore is preferably sized and shaped to allow the bone anchor 350 therethrough. In the illustrated embodiment, the bone anchor 350 is a 1.6 millimeter k-wire, and therefore the pathway is at least about 0.63 inch wide.

Figure 26:
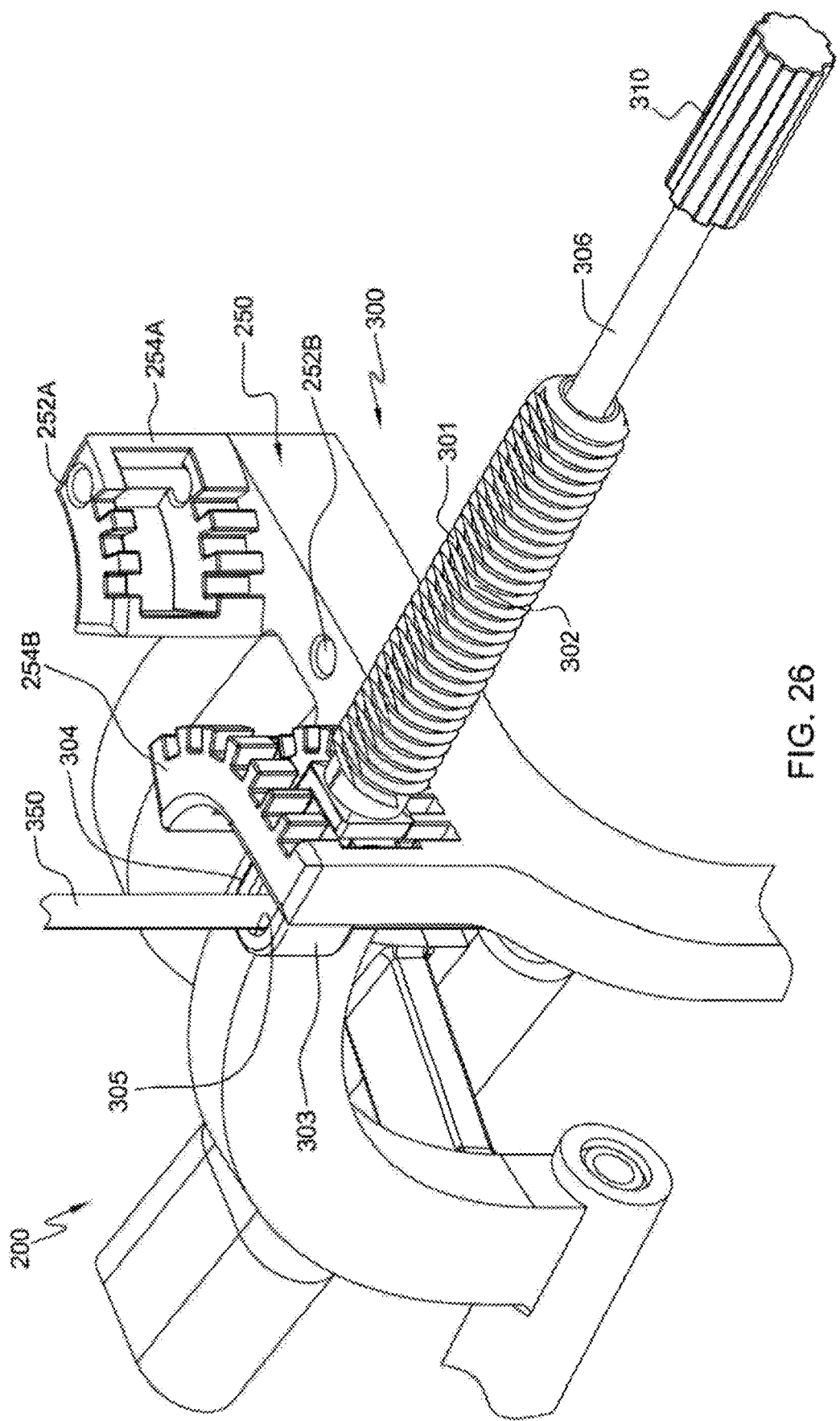
FIG. 26 is a front elevational perspective view of a first portion of the clamp of FIG. 24 applied to the surgical instrument of FIG. 19.
Figure 28:
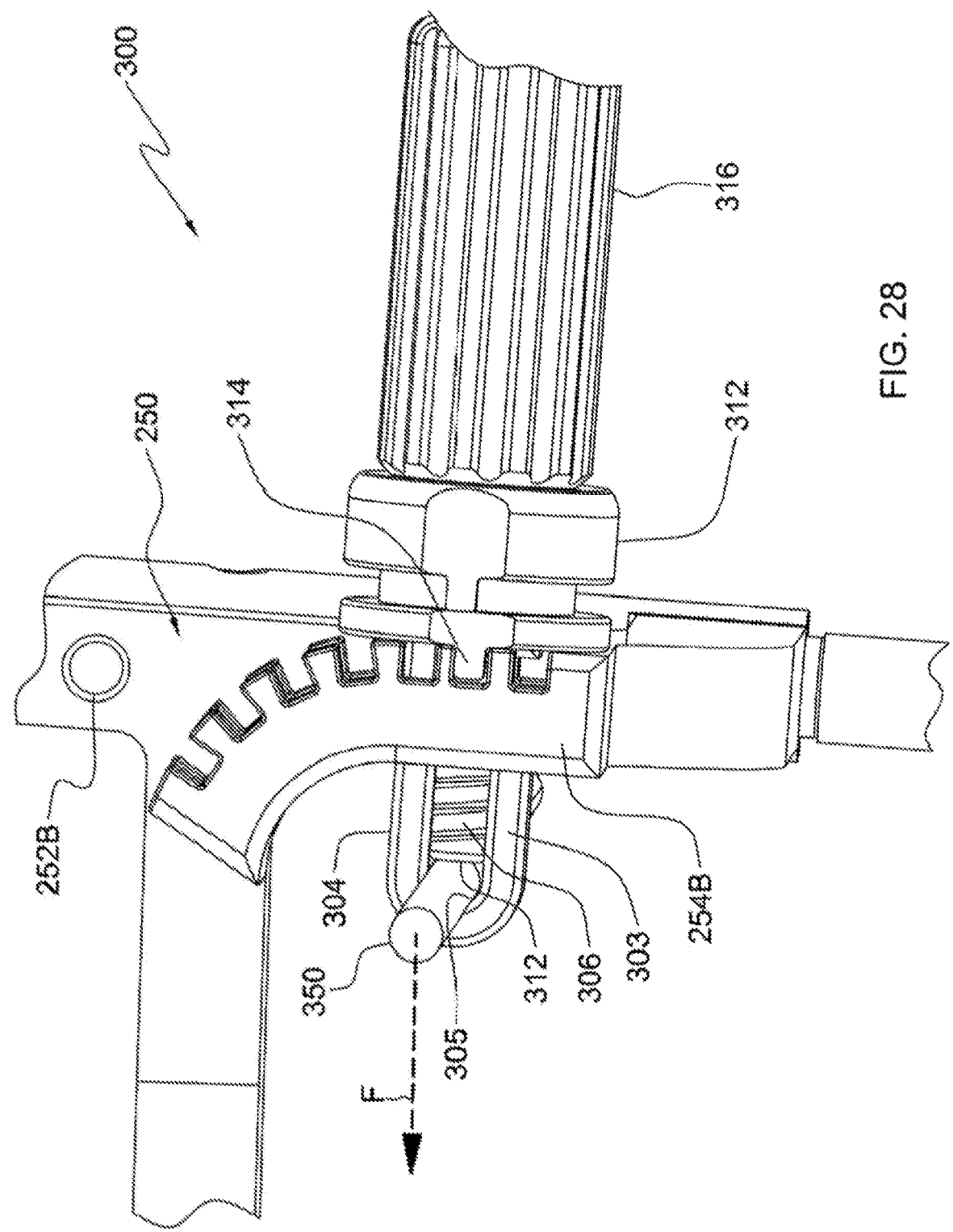
FIG. 28 is a front elevational perspective view of a first portion of the clamp of FIG. 24 applied to the surgical instrument of FIG. 19.

As shown in FIG. 26, once the bone anchor 350 is positioned in the interior of the head portion 303, an elongate compression member 306 may be coupled to the internally threaded aperture of the shaft 302 of the hook member 301. As such, the compression member 306 is preferably shaped and sized to engage the internal threads of the interior aperture of the shaft 302 of the hook member 301. As shown in FIG. 26, the compression member 306 may also include a manually engageable member 310 for manual rotation of the compression member 306 within the shaft 302. The compression member 306 is also preferably sized such that the end 312 of the compression member 306 is capable of threading through the shaft 302, into the interior of the head portion 303 and at least adjacent to the arcuate channel 305, as best shown in FIGS. 24 and 28. In such a configuration, as shown in FIG. 26, the compression member 306 may be rotationally advanced within the shaft 302 of the hook member 301 such that the end 312 of the compression member 306 engages the bone anchor 350 and compresses the bone anchor 350 against the arcuate channel 305. As such, the compression member 306 may be effective in securing the bone anchor 350 to the hook member 301 (as the bone anchor 350 is compressed between the end 312 of the compression member 306 and the arcuate channel 305, and the compression member 306 is carried within the hook member 301). As such, the bone anchor 350 can be inserted into a bone, and used as a joystick to reorient or reposition the bone. Once a satisfactory orientation and position of the bone is achieved, the orientation and position can be "locked" by securing the bone anchor 350 to the hook member 301, and further securing the hook member 301 to the clamp members 254A, 254B as discussed below.

Figure 27:
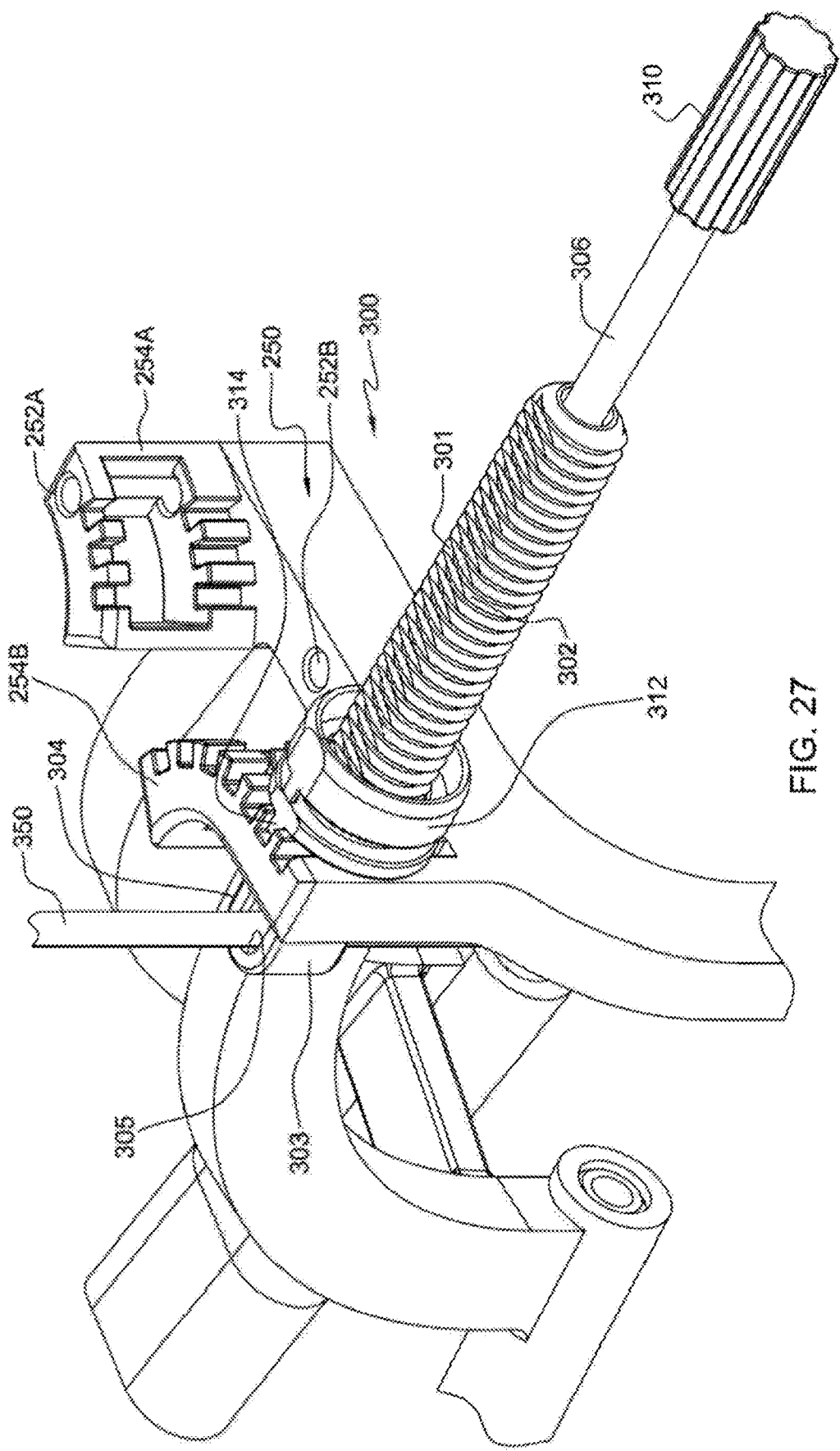
FIG. 27 is a front elevational perspective view of a first portion of the clamp of FIG. 24 applied to the surgical instrument of FIG. 19.
Figure 29:
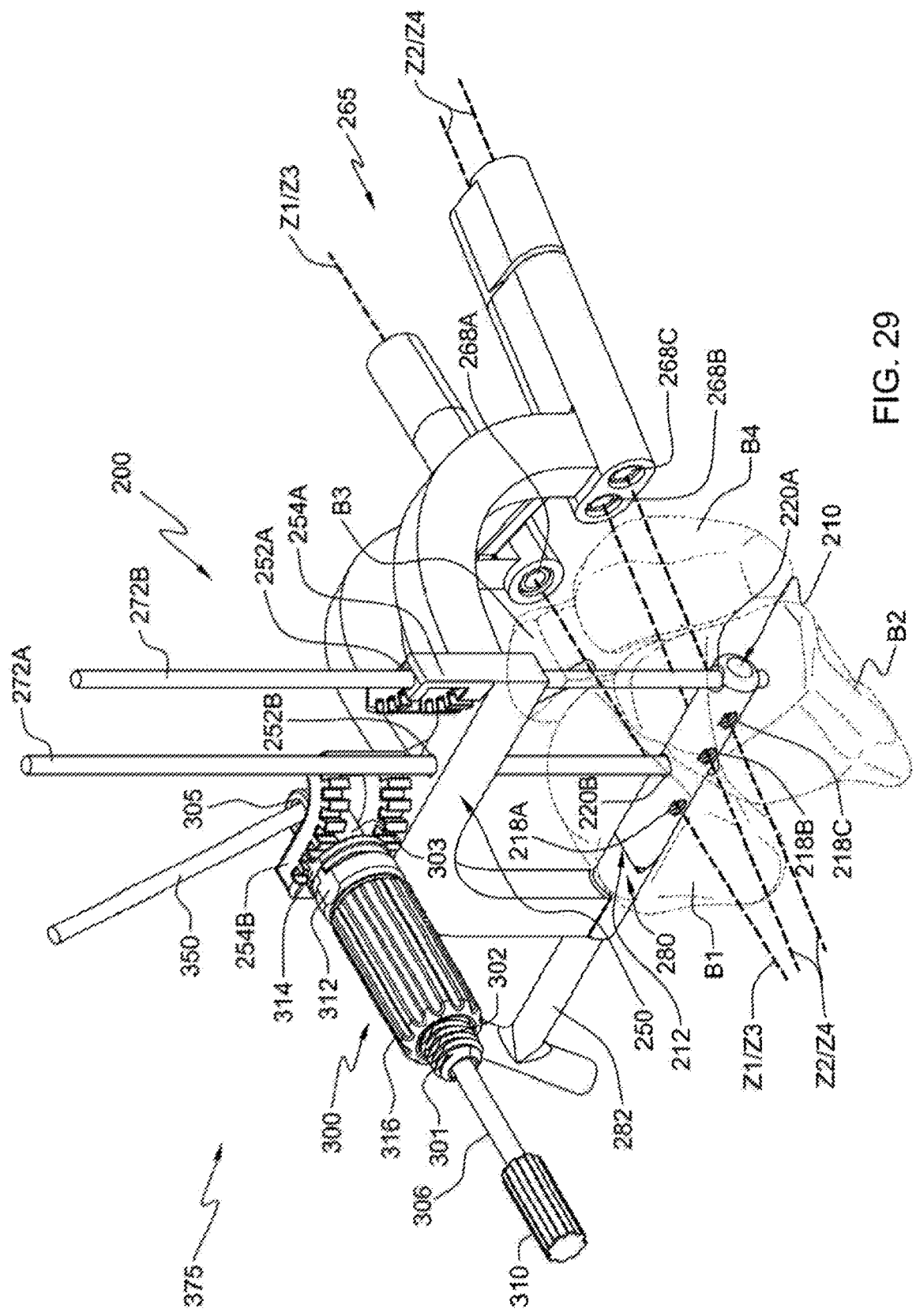
FIG. 29 is a rear elevational perspective view of the clamp of FIG. 24 applied to the surgical instrument of FIG. 19 partially implanted in exemplary bones of an upper extremity.

Movement of the bone anchor 350, the hook member 301 and compression member 306, may be restricted through the use of a washer member 312, as shown in FIGS. 27-29. The washer member 312 may include an aperture therethrough and at least one rib 314 extending from a bearing surface. The washer member 312 may preferably be configured to pass over the compression member 306 and shaft 302 of the hook member 301 via the aperture. As shown in FIGS. 27-29, in such a configuration the at least one rib 314 of the washer member 312 may engage the channels or grooves of the ribbed or slotted surface of the second clamp member 254B. In some embodiments, the at least one rib 314 is a "V" shaped rib 314 configured to mate with "V" shaped grooves on the ribbed or slotted surface of the second clamp member 254B. The washer member 312 may also engage the head portion 303 and/or the shaft 302 of the hook member 301.

As show in FIG. 28, once the at least one rib 314 of the washer member 312 is engaged with a channel or groove of the ribbed or slotted surface of the second clamp member 254B, a nut 316 may threadably engaged with the outer threading of the shaft 302 of the hook member 301. In such embodiments, the nut 316 may preferably include an internally threaded aperture configured to threadably engage the outer threading of the shaft 302 of the hook member 301. The nut 316 can be rotationally advanced along the shaft 302 of the hook member 301 and into abutment with the washer member 312. The nut 316 may therefore lock the washer member 312, and the at least one rib 314, against the ribbed or slotted surface of the second clamp member 254B. As the washer member 312 and nut 316 are larger than the aperture of the ribbed or slotted surface of the second clamp member 254B, the construct including the hook member 301, compression member 306 and bone anchor 350 is prevented from movement in a direction from the head portion 303 to the shaft 302 of the hook member 301. Further, the construct may be secured to the second clamp member 254B and the bone anchor 350 such that movement of the bone anchor, and the bone coupled thereto, is substantially prevented in the dorsal-palmar direction.

In some embodiments, the nut 316 may be rotated to such a degree that the nut 316 compresses the washer member 312 against the ribbed or slotted surface of the second clamp member 254B. In some such embodiments, the washer member 312 may be configured to apply a compressive force to the shaft 302 of the hook member 301 when it is compressed, thereby further locking the construct, such as locking rotation of the construct. Still further, in some embodiments the head portion 303 is non-circular and partially passes through the aperture 255B of the second clamp member 254B. In some such embodiments, the washer member 312 engages the non-circular profile of the head portion, and via the at least one rib 214 prevents rotation of the hook member 301, and therefore the bone anchor 350 captured in the arcuate channel 305.

As described above and shown in FIG. 28, the particular orientation and position of the clamp 300 is determined by which particular channel or groove of the ribbed or slotted surface of the second clamp member 254B is engaged by the at least one rib 314 of the washer member 312. The particular orientation and position of the clamp 300 may therefore depend upon the particular position and orientation of the bone anchor 350.

In some embodiments, as indicated in FIG. 28, the bone anchor 350 may include a force F that biases the bone anchor 350 in a direction away from the second clamp member 254B. Such a force may result from the use of the bone anchor 350 as a manipulation tool for the bone to coupled thereto (i.e., use of the bone anchor 350 as a joystick). In such a scenario, the clamp 300 may primarily prevent the bone member 350 from movement resulting from the bias force F, as shown in FIG. 28. For example, the clamp 300 may not prevent movement of the clamp 300 in a direction towards the second clamp member 254B, and therefore the clamp 300 may not prevent the bone anchor 350 from movement in a direction towards the second clamp member 254B.

FIG. 29 shows an exemplary construct 375 including the exemplary targeting guide 200, the exemplary clamp 300 and exemplary bone anchors applied to target fusion bones. In particular, the complete construct 375 is applied to the capitate B1, hammate B2, lunate B3 and triquetral B4 bones of the wrist. As shown in FIG. 29, the exemplary fusion implant 210 is implanted in a cavity that spans the capitate bone B1 and the hammate bone B2. The exemplary fusion implant 210 is positioned such that the first internally threaded aperture 218A and the first non-threaded aperture 220A is positioned within the capitate bone B1, and the second and third internally threaded apertures 218B, 218C and the second non-threaded aperture 220B are positioned within the hammate bone B2. Also, because the fusion implant 210 is coupled to the outrigger member 280, the fusion implant 210 is in the first or "proper" predetermined orientation with respect to the targeting instrument 200.

As the fusion implant 210 is in the "proper" orientation with respect to the targeting instrument 200, a first bone anchor 272A has been passed through the first bone anchor aperture 252A, into the capitate bone B1, and finally through the first non-threaded aperture 220A. Similarly, a second bone anchor 272B has been passed through the second bone anchor aperture 252B, into the hammate bone B2, and finally through the second non-threaded aperture 220B. In such a configuration, the capitate bone B1, hammate bone B2 and the construct 375 (fusion implant 210 and targeting instrument 200) are fixed or locked with respect to one another.

The lunate bone B3 is also locked or fixed to the construct 375, and therefore the capitate B1 and hammate B2 bones, through the clamp 300 and joystick bone anchor 350. As shown in FIG. 29, the joystick bone anchor 350 is implanted into the lunate bone B3 and used to reposition the lunate, such as to an anatomical position. For example, the joystick bone anchor 350 may have been used to position the center of the lunate bone B3 about 11 degrees radial to the capitate-hammate articulation longitudinal line. Once the lunate bone B3 has been repositioned or reoriented, the clamp 300 was used to lock the position and orientation of the lunate bone B3 with respect to the targeting instrument 375, and thus the capitate bone B1, hammate bone B2 and fusion implant 210 as well. In such a configuration, the construct 375 can be used to drill apertures via the at least one guide member 265 through the capitate B1, hammate B2, lunate B3 and triquetral B4 bones to the internally threaded apertures 218A-C of the fusion implant 210. As the construct 375 is fixed with the capitate bone B1, hammate bone B2 and lunate bone B3 via the bone anchors 272A, 272B, 350, the position and orientation of the cavities formed by the drilling process can be assured. One the cavities to the to the internally threaded apertures 218A-C have been formed, the fusion members 50 described above can be used to draw the capitate B1 and lunate B3 bones together, and the hammate B1 and triquetral B4 bones together such that they abut each another. Further, depending upon the level of rotation of the fusion members 50, the fusion members 50 may apply a compressive force to the joint between the capitate B1 and lunate B3 bones, and the hammate B1 and triquetral B4 bones.

A surgical method for fusing target fusion bones will now be described. The method utilizes some of the devices, instruments, features, aspects, components and the like described above, and therefor reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bones or other tissue not specifically discussed herein without departing from the spirit and scope of the surgical method.

Assuming four adjacent, but spaced, bones were targeted for fusion, a fusion implant, such as fusion implant 10, and fusion members, such as fusion member 50, may be used to fuse the bones to one another. For example, in reference to the bones of the wrist, the hammate, capitate, lunate ad triquetral bones may be fused to one another. In order to implant the fusion implant 10 into the bones, an implant cavity will first be formed into two of the adjacent bones. For example, in some embodiments the hammate and capitate bones are dilled out to form the cavity. The method of forming the cavity may include usage of the above described guide clamp 100.

In some embodiments, a dorsal midline incision is made in the wrist through the third compartment, retracting the EPL tendon. In some embodiments, the capsule may then be incised in a longitudinal direction and elevated both radially and ulnarly. In some such embodiments, the scaphoid is excised with a ronguer. The distal aspect of the lunate and triquetral bones and the proximal aspect of the capitate and hammate bones may then be decorticated.

At such a junction, the longitudinally extending second bone abutment surface 112 of the bone abutment member 110 of the second arm 104 of the guide clamp 100 may then be placed on the dorsal side of the hammate bone, and the projection 116 of the laterally extending third bone abutment surface 11 may be placed in the detent commonly found on the medial side of the hammate bone (e.g., the tubercle/depression located at the capitate/trapezoid articulation) that opposes the capitate bone, as shown in FIG. 18. In some such embodiments, the guide member 106 of the first arm 102 is positioned adjacent the lateral side of the capitate bone that opposes the hammate bone, as shown in FIG. 18. The position of the guide member 106 may then be adjusted such that the guide member 106 is located in an intermediate position in the dorsal-palmar direction, or slightly a more palmar position, such that the longitudinal axis X3-X3 of the guide member extending to the projection 116 is located in a intermediate position through the hammate and capitate bones in the dorsal-palmar and distal-proximate direction to ensure the longitudinal axis X3-X3 passes through a significant portion of both the hammate and capitate bones, as shown in FIG. 18. For example, the longitudinal axis X3-X3 of the guide member 106 may have about 10 degrees to about 15 degrees of tilt an ulnar proximal palmar direction.

Once a particular location of the guide member 106 is determined, a user may squeeze the manually engageable members 122A, 122B of the first and second arms 102, 104 to translate the guide member 106 towards the projection 116 of the third bone abutment surface 11. In some embodiments, such translation may force a spike of the first bone abutment surface 108 of the guide member 106 into the capitate bone, as shown in FIG. 18. In some embodiments, such translation may force the first bone abutment surface 108 into abutment with the capitate bone, as shown in FIG. 18. Once the first bone abutment surface 108 is positioned into and/or in abutment with the capitate bone, the first and second ratcheting members 124A, 124B of the arms 102, 104 may lock the position of the first bone abutment surface 108 with respect to the capitate bone, as shown in FIG. 18.

In some embodiments, a drill including a drill bit sized and shaped to be received within the aperture or tube of the guide member 106 is inserted in the guide member 106 and the drill is plunged into the capitate and hammate bones. In some such embodiments, the guide member 106 is sized and shaped to orient and position the drill such that the drill creates an implant cavity in the capitate and hammate bones that is aligned along the longitudinal axis X3-X3 of the guide member 106. The cavity may be formed such that the cavity extends through the capitate and at least partially through the hammate bones. After the cavity is formed, the first and second ratcheting members 124A, 124B of the arms 102, 104 may be disengaged and the guide clamp 100 removed from the capitate and hammate bones.

Once the implant cavity in the capitate and hammate bones is formed, a fusion implant 10, 210 may be prepared for insertion into the cavity. The method for preparing the cavity may include the step of coupling the fusion implant 10, 210 to an instrument, such as the targeting instrument 200, in a predefined first or "proper" orientation, as shown n FIGS. 19-21. The predefined orientation may result from the profile of the second end 14, 214 of the fusion implant 10, 210 and/or the profile of the end of the outrigger member 280. In some embodiments, coupling the fusion implant 10, 210 to the targeting instrument 200 includes the step of orienting the fusion implant 10, 210 and the outrigger member 280 of the targeting instrument 200 with respect to each other such that the first end 12, 212 of the fusion implant 10, 210 is properly mated with the end of the outrigger member 280 of the targeting instrument 200. In some such embodiments, such a step may include orienting the fusion implant 10, 210 with respect to the outrigger member 280 such that the first end 14, 214 of the fusion implant 10, 210 and the end profile of the outrigger member 280 mate and a visual or tactile indication indicating a incorrect orientation is not present. In some embodiments, such an orienting step may include orienting the fusion implant 10, 210 with respect to the outrigger member 280 such that longitudinally extending apertures in the first end 14, 214 of the fusion implant 10, 210 and the outrigger member 280 are aligned.

In some embodiments, once the fusion implant 10, 210 and the outrigger member 280 are mated in the first or "proper" predefined orientation, the fusion implant 10, 210 and the outrigger member 280 are selectively coupled to each other in the orientation. Coupling the fusion implant 10, 210 and the outrigger member 280 in the predefined orientation may include the step of inserting a threaded tightening bolt 282 into the outrigger member 280 aperture and the aperture 40, 240 of the fusion implant 10, 210. The threaded tightening bolt 282 may be rotatably inserted into the aperture 40, 240 of the fusion implant 10, 210, and the further rotated to pull the first end 14, 214 of the fusion implant 10, 210 into the end of the outrigger member 280 to selectively couple the fusion implant 10, 210 and the outrigger member 280.

Coupling the fusion implant 10, 210 and the outrigger member 280 to one another in the first orientation may include the step of aligning the internally threaded apertures 18A-C, 218A-C of the fusion implant 10, 210 with apertures 268A-C of the guide members 265 of the targeting instrument 200, such as aligning the axes Z1-Z1, Z2-Z2 of the internally threaded apertures 18A-C, 218A-C of the fusion implant 10, 210 with the axes Z3-Z3, Z4-Z4 of the apertures 268A-C of the guide members 265 of the targeting instrument 200, as shown n FIGS. 19-21. The coupling step may also include aligning the non-threaded apertures 20A, 220A, 20B, 220B, with the first and second bone anchor apertures 252A, 252B of the targeting member 250 of the targeting instrument 200, such as aligning the axes Y1-Y1 of non-threaded apertures 20A, 220A, 20B, 220B, with the axes Y2-Y2 of the first and second bone anchor apertures 252A, 252B of the targeting member 250 of the targeting instrument 200, as shown n FIGS. 19-21.

Once the fusion implant 10, 210 and the outrigger member 280 are coupled to one another, the fusion implant 10, 210 may be inserted into the implant cavity formed in the hammate and capitate bones, as shown in FIGS. 22, 23 and 29. In some embodiments, the fusion implant 10, 210 is positioned in the implant cavity such that the first internally threaded aperture 18A, 218A and the first non-threaded aperture 20A, 220A are positioned within the capitate bone, and the second and third internally threaded apertures 18B, 218B, 18C, 218C and the second non-threaded aperture 20B, 220B are positioned within the hammate bone. The position of the fusion implant 10, 210 in the implant cavity in the hammate and capitate bones may be checked via fluoroscopic visualization.

With the fusion implant 10, 210 properly positioned within the implant cavity in the hammate and capitate bones, the targeting instrument 200, and therefore the fusion implant 10, 210, can be rotated about the longitudinal axis X-X of the fusion implant 10, 210 and into an orientation such that lunate and triquetral bones are positioned between the fusion implant 10, 210 and the at least one guide member 265, as shown in FIGS. 22 and 23. More specifically, the targeting instrument 200 may be positioned such that the axes Z3-Z3, Z4-Z4 of the guide apertures 268A-C of the guide member 265 pass through intermediate portions of the lunate and triquetral bones in the dorsal-palmar direction. In some embodiments, the targeting instrument 200 may be positioned such that the outrigger member 280 is perpendicular to the longitudinal axis of the carpus, or flexed no more than about 5 degrees.

Once the targeting instrument 200 is properly positioned with respect to the hammate, capitate, lunate and triquetral bones, the positioning and/or orientation of the targeting instrument 200 may be fixed to at least one of the hammate, capitate, lunate and triquetral bones. For example, in one embodiment once the targeting instrument 200 is properly positioned a first bone anchor, such as a k-wire, is inserted through the first bone anchor aperture 252A of the targeting member 250, into the hammate bone, and into the first non-threaded aperture 20A, 220A of the fusion implant 10, 210. Similarly, a second bone anchor, such as a k-wire, may be inserted through the second bone anchor aperture 252B of the targeting member 250, into the capitate bone, and into the second non-threaded aperture 20B, 220B of the fusion implant 10, 210. In this way, the first and second bone anchors can couple or fix the targeting instrument 200, fusion implant 210, hammate bone and capitate bone with respect to one another.

The lunate bone may also be fixed to the targeting guide 200. In some embodiments, a third bone anchor 350 may be implanted into the lunate bone, and then used as a joystick to reposition the lunate. In some embodiments, the joystick bone anchor may be used to position the lunate bone in an anatomical position. For example, the third bone anchor 350 may be used to position the center of the lunate bone about 11 degrees radial to the capitate-hammate articulation longitudinal line. In some embodiments, the third bone anchor 350 is used to reposition the lunate bone in the dorsal-palmar direction. Once the lunate bone has been repositioned, it may be fixed to the targeting instrument 200 to maintain its new position.

In some embodiments, the third bone anchor 350 is secured to the targeting instrument 200 after it is used to reposition the lunate by a clamp 300. In some such embodiments, the third bone anchor 350 is positioned within an inner portion of a hook member 301 of the clamp 300, and a compression member 306 is rotatably coupled hook member 301 and advanced through the hook member 301 to compress the third bone anchor 350 between the compression member 306 and an arcuate channel 305 of the hook member 301. In some such embodiments, the hook member 301 is coupled to a second clamp member 254B of the targeting member 250 of the targeting instrument 200. The hook member 301 may be coupled to the second clamp member 254B by a washer 312 including a rib 214 configured to engage the second clamp member 254B, and a nut that compresses the washer 312 against the second clamp member 254B.

In some embodiments, a fourth bone anchor is inserted in the triquetral bone, and the triquetral bone is repositioned using the fourth bone anchor as a joystick. After repositioning the triquetral bone with the joystick fourth bone anchor, the fourth bone anchor may be fixed to the targeting guide 200 to maintain the new position. The fourth bone anchor may be fixed to the targeting guide 200 in a substantially similar way as compared to fixation of the third bone anchor 350 to the targeting guide 200. The primary difference between the fixations being the use of the first clamp member 254A, as opposed to the second clamp member 254B.

Once the targeting instrument 200 is fixed to at least the hammate, capitate and lunate bones via the bone anchors, fusion member cavities may be formed in the bones to the internally threaded apertures 18A-C, 218A-C of the fusion implant 10, 210. Before the fusion member cavities are formed, a depth gauge may be inserted into the at least one guide member 265 to determine the depth of the internally threaded apertures 18A-C, 218A-C of the fusion implant 10, 210, and therefore the proper length that the cavities should be drilled to and how far the fusion members should be advanced into the cavities. In some embodiments, after the depth gauges are used to determine the proper lengths of the fusion member cavities, particular drill bushings 270A-C configured to stop the drill drilling process at the correct depths are inserted into the guide apertures 268A-C of the guide members 265. In some embodiments, a drill and drill bit are guided by the drill bushings 270A-C to created fusion member apertures in the hammate, capitate, lunate and triquetral bones to the internally threaded apertures 18A-C, 218A-C. In some such embodiments, the fusion member apertures may be spaced about 2 millimeters or less from the internally threaded apertures 18A-C, 218A-C.

In some embodiments, once the fusion member apertures are formed, the fusion members 50 are inserted and driven into the cavities. In some embodiments, the fusion members 50 are rotatably inserted into the cavities such that the first externally threaded portion 56 including the first thread lead is threadably coupled to the internally threaded apertures 18A-C, 218A-C of the fusion implant 10, 210. In some such embodiments, the second externally threaded portion is engaged with either the capitate or triquetral bones, depending upon which cavity is used. In some embodiments, the non-threaded portion spans the joint between the lunate and capitate bones, or the hammate and triquetral bones, depending upon which cavity is used.

In some embodiments, insertion of a fusion member 50 into the first internally threaded aperture 18A, 218A substantially eliminates the space between the adjacent surfaces of the capitate and lunate bones. In some such embodiments, the fusion member 50 applies a compressive force to the joint between the adjacent surfaces of the capitate and lunate bones. In some embodiments, insertion of a fusion member 50 into the second or third internally threaded apertures 18B, 218B, 18C, 218C substantially eliminates the space between the adjacent surfaces of the hammate and triquetral bones. In some such embodiments, the fusion member 50 applies a compressive force to the joint between the adjacent surfaces of the hammate and triquetral bones.

One advantage of the embodiments discussed herein of the present invention is that the fusion implants and associated fusion members draw adjacent spaced bones together. Another advantage of the fusion implants and associated fusion members of the embodiments discussed herein is that they apply a compressive force to the joint of abutting bones. Another advantage of the fusion implant, instruments and methods discussed herein is that they provide consistent, repeatable alignment between the fusion member, target fusion bones and fusion processes, such as securement and drilling processes. Another advantage of the fusion implant, instruments and methods discussed herein is that the target fusion bones are secured such that a predetermined orientation or positioning of the fusion implant and associated fusion members is consistently achieved.

The fusion implants, fusion members, fusion devices, constructs, instruments, clamps and methods disclosed herein may include one or more features of the fusion implants, fusion members, fusion devices, constructs, instruments, clamps and methods disclosed and/or claimed in the following patent application that is assigned to the assignee of the present invention and is hereby expressly incorporated by reference in its entirety as part of the present disclosure: U.S. patent application Ser. No. 13/982,152 filed on even date herewith, and entitled "Lower Extremity Fusion Devices and Methods".

As may be recognized by those of ordinary skill in the pertinent art based on the teachings herein, numerous changes and modifications may be made to the above-described and other embodiments of the present invention without departing from the spirit of the invention as defined in the claims. For example, the particular devices, instruments, constructs and methods discussed herein with respect to particular bones may be used with other bones or tissue to achieve advantageous fusion. As another example, particular aspects or features described or illustrated herein as integral may be made from individual separate components. Similarly, particular aspects or features described or illustrated herein as individual separate components may be combined into an integral unit. As another example, the threading described herein may take any thread form known in the art that differs from the described or illustrated threading. As another example, any aspect of the devices discussed herein that may be temporarily or permanently implanted into the body of a patient may include a texture, coating, surface finish or the like to facilitate coupling of the aspect with the patient. As another example, the fusion members may include at least one aperture configured to facilitate other fusion members from attaching or coupling thereto. Therefore, the implants, fusion devices or constructs disclosed herein may include at least one fusion member coupled to at least one other fusion member. As yet another example, the fusion implants, fusion members, fusion devices, constructs, instruments and methods discussed herein may be configured to facilitate fusion of more than two bones, whether naturally adjacent or not. For example, the implants may be configured for implantation, at least partially into two or more bones. Similarly, for example, the fusion members may be configured to pass through, at least partially, two or more bones. As another example, fusion devices, constructs, instruments and methods discussed herein may be configured for use with one fusion member, or more than one fusion members, such as more than three fusion members. As such, the number of internally threaded apertures disclosed herein may differ. Further, the fusion devices, constructs, instruments and methods discussed herein may be configured with implants with non-threaded apertures for coupling bone anchors through at least one bone and through the non-threaded aperture to stabilize the implant with the at least one bone. As another example, the targeting instrument disclosed herein may be configured to interact with, and include, a bone anchor clamp.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone fusion device for use with bones of an upper extremity, the bone fusion device comprising:
   a fusion implant configured for implantation into a cavity spanning at least two adjacent bones, the fusion implant including:
   a body having a first end, and
      a second end substantially opposing the first end;
      the first end including an attachment mechanism comprising a first tip surface and a second tip surface at a longitudinal end of the first end, the first tip surface and the second tip surface connected to a body surface of the body angled relative to an axis of the implant such that the first tip surface and the second tip surface have different longitudinal dimensions to allow a user to couple the implant with an instrument in a predefined first orientation different from a second undesired orientation;
      the body having a substantially smooth outer surface and defining a longitudinal axis, the body including at least two non-threaded apertures extending laterally through the body from a first side of the body to a second side of the body and at least two internally threaded apertures including a first thread lead extending laterally through the body from a third side of the body to a fourth side of the body, the at least two threaded apertures including a first threaded aperture proximate the first end, and a second threaded aperture proximate the second end and angled with respect to the longitudinal axis of the body such that the second threaded aperture defines an axis that angles away from the second end as it extends from the third side to the fourth side.

2. The bone fusion device of claim 1, wherein the at least two non-threaded apertures of the body define substantially parallel axes.

3. The bone fusion device of claim 1, wherein the fusion implant is substantially cylindrical, and the first and second sides of the body are spaced about 90 degrees from the third and fourth sides of the body about the longitudinal axis.

4. The bone fusion device of claim 1, wherein the body of the fusion implant includes a third internally threaded aperture adjacent the second internally threaded aperture, the third internally threaded aperture extending laterally through the body and defining an axis that is substantially parallel to the axis of the second internally threaded aperture.

5. The bone fusion device of claim 4, wherein the fusion implant includes only two non-threaded apertures and the first, second and third internally threaded apertures, and wherein the first internally threaded aperture is adjacent the first end, a first non-threaded aperture is positioned between the first internally threaded aperture and the second end, the third internally threaded aperture is positioned between the first non-threaded aperture and the second end, the second internally threaded aperture is positioned between the third internally threaded aperture and the second end, and a second non-threaded aperture is positioned between the second internally threaded aperture and the second end.

6. The bone fusion device of claim 5, wherein the angle between the axis of the first internally threaded aperture and the longitudinal axis of the body adjacent the third side and first end of the body is within the range of about 95 degrees to about 80 degrees, and the angle between the axis of the second and third internally threaded apertures and the longitudinal axis of the body adjacent the third side and first end of the body is within the range of about 92 degrees to about 106 degrees.

7. The bone fusion device of claim 6, wherein the first internally threaded aperture is angled with respect to the longitudinal axis of the body such that it defines an axis that angles away from the first end as it extends from the third side to the fourth side.

8. The bone fusion device of claim 7, wherein a plane extends between the axes of the internally threaded apertures and the longitudinal axis of the body, and the axes of the non-threaded apertures are normal to the plane.

9. The bone fusion device of claim 1, wherein the body further comprises a third end tip surface on the third side of the body extending between the first tip surface and the second tip surface, and
   a fourth end tip surface on the fourth side of the body extending between the first tip surface and the second tip surface.

10. The bond fursion device of claim 9, wherein the third tip surface and the fourth tip surface are radiused to form blunt convex surfaces.

11. The bone fusion device of claim 10, wherein the third tip surface and the fourth tip surface are opposite each other with respect to a second axis which is lateral to the longitudinal axis.

12. The bone fursion device of claim 11, wherein the third tip surface and the fourth tip surface are beveled inwardly substantially towards the longitudinal axis or the second axis.

13. The bone fusion device of claim 1, the body further comprising a threaded cavity having an opening at the longitudinal end of the first end between the first tip surface and the second tip surface and extending within the body along the longitudinal axis.

14. The bond fusion device of claim 13, wherein the threaded cavity further comprises a non-threaded cavity portion bounding a first space which is adjacent to and in fluid communication with the opening, and a threaded cavity portion bounding a second space which is adjacent to the first space and in fluid communication wit the first space and the opening.

15. The bone fusion device of claim 14, wherein the threaded cavity is configured to rotatably received a tightening member.

16. The bond fusion device of claim 14, wherein the diameter of the threaded cavity portion is less than the diameter of the non-threaded cavity portion.

* * * * *